United States Patent
Bourg, Jr. et al.

(10) Patent No.: US 7,068,817 B2
(45) Date of Patent: Jun. 27, 2006

(54) METHOD FOR ON-LINE MACHINE VISION MEASUREMENT, MONITORING AND CONTROL OF PRODUCT FEATURES DURING ON-LINE MANUFACTURING PROCESSES

(75) Inventors: Wilfred M. Bourg, Jr., Melissa, TX (US); Steven A. Bresnahan, Plano, TX (US); Gabe Jan Haarsma, Houston, TX (US); John F. MacGregor, Dundas (CA); Paul Allan Martin, Celina, TX (US); Honglu Yu, Hamilton (CA)

(73) Assignee: McMaster University, Hamilton ( * ) Notice: Subject to any disclaimer, the term of this patent is extended or adjusted under 35 U.S.C. 154(b) by 401 days.

(21) Appl. No.: 10/289,592

(22) Filed: Nov. 7, 2002

(65) Prior Publication Data

US 2004/0091135 A1 May 13, 2004

(51) Int. Cl.
*G06K 9/00* (2006.01)
(52) U.S. Cl. .................. 382/110; 382/170; 382/190
(58) Field of Classification Search ............... 382/110, 382/170, 190–208
See application file for complete search history.

(56) References Cited

U.S. PATENT DOCUMENTS

| 4,790,022 | A | * | 12/1988 | Dennis | 382/110 |
|---|---|---|---|---|---|
| 4,979,225 | A | * | 12/1990 | Tsujiuchi et al. | 382/165 |
| 5,206,918 | A | * | 4/1993 | Levene | 382/110 |
| 5,318,173 | A | * | 6/1994 | Datari | 209/580 |
| 5,335,293 | A | * | 8/1994 | Vannelli et al. | 382/110 |
| 5,818,953 | A | * | 10/1998 | Queisser et al. | 382/110 |
| 5,842,150 | A | * | 11/1998 | Renberg et al. | 702/23 |
| 5,887,073 | A | * | 3/1999 | Fazzari et al. | 382/110 |
| 5,956,413 | A | * | 9/1999 | Oste et al. | 382/110 |
| 6,574,363 | B1 | * | 6/2003 | Classen et al. | 382/165 |
| 6,681,032 | B1 | * | 1/2004 | Bortolussi et al. | 382/118 |
| 6,751,354 | B1 | * | 6/2004 | Foote et al. | 382/224 |
| 6,847,447 | B1 | * | 1/2005 | Ozanich | 356/326 |
| 2003/0128877 | A1 | * | 7/2003 | Nicponski | 382/224 |
| 2003/0215141 | A1 | * | 11/2003 | Zakrzewski et al. | 382/190 |

OTHER PUBLICATIONS

Davidson et al., "Fuzzy Models to Predict Consumer Ratings for Biscuits Based on Digital Image Features", Feb. 2001, IEEE Transaction on Fuzzy Systems, vol. 9, Issue 1, pp. 62-67.*

Yeh et al., "Colour Bake Inspection System Using Hybrid Artificial Neural Networks", Dec. 1995, IEEE Conference on Neural Networks, vol. 1, pp. 37-42.*

(Continued)

*Primary Examiner*—Bhavesh M. Mehta
*Assistant Examiner*—Aaron Carter
(74) *Attorney, Agent, or Firm*—Scott L. Harper; Colin P. Cahoon; Carstens & Cahoon, LLP

(57) ABSTRACT

A method for extracting feature information from product images using multivariate image analysis based on Principal Component Analysis (PCA) which is used to develop predictive models for feature content and distribution on the imaged product. The imaging system is used to monitor product quality variables in an on-line manufacturing environment. It may also be integrated into a closed-loop feedback control system in automated systems.

43 Claims, 51 Drawing Sheets

OTHER PUBLICATIONS

Sanchez et al. "Automatic Vision Inspection Sytem for the Analysis and Detection of Breakages and Defects of Satsuma Slices", Oct. 1994, IEEE Conference on Systems, Man, and Cybernetics, vol. 1, pp. 853-858.*

* cited by examiner

| Product | Sample images | | | Comments |
|---|---|---|---|---|
| | Non-seasoned | Low-seasoned | High-seasoned | |
| A | 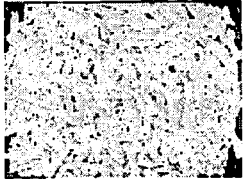 |  | 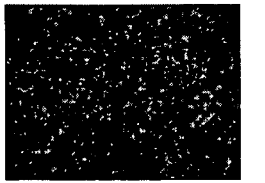 | Off-line; 83 samples; 40 for training and 43 for test |
| B |  | 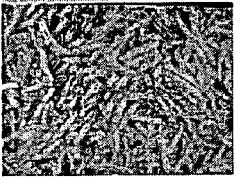 | 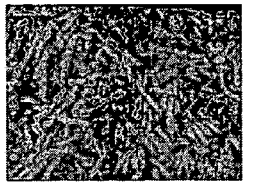 | On-line; 180 samples; 90 for training and 90 for test |
| C |  | 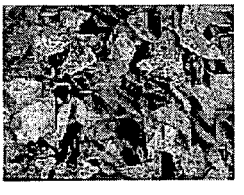 |  | On-line; 110 samples; 55 for training and 55 for test |
Figure 1-a + Channel Red   × Channel Green   ○ Channel Blue
(a) Average color   (b) 1st PC loading vector (a) Non-seasoned product　　(b) Low-seasoned product　　(c) High-seasoned product

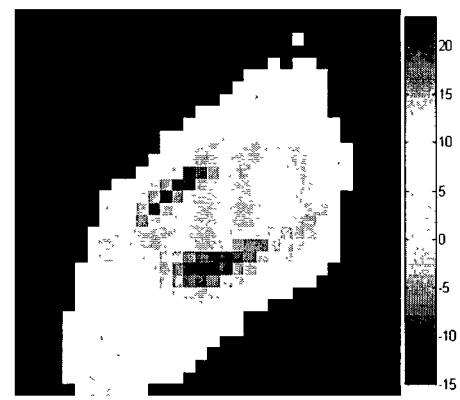
(a) Method 3
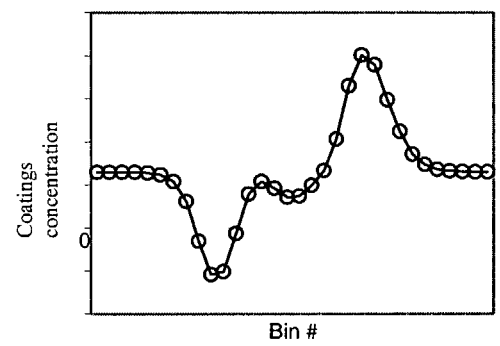
(b) Method 4
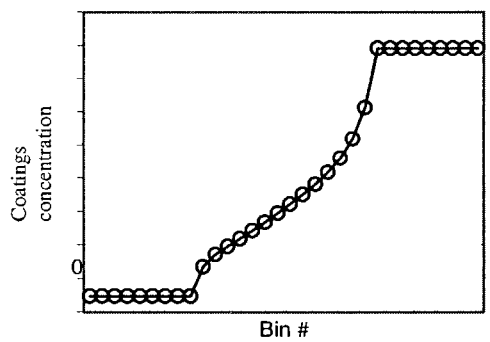
(c) Method 5
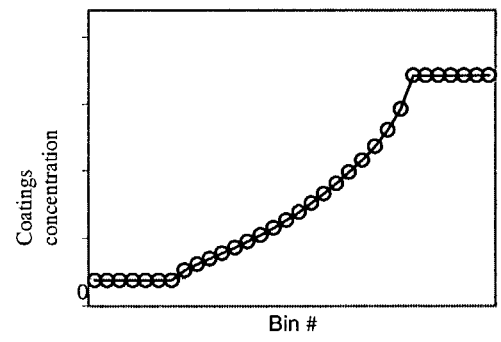
(d) Method 6
FIGURE 16

(a) Color-coded summation of absolute covariance plots (cold color represents small value, warm color represents large value)

(b) Red pixels show the location of belt image; Purple polygon is the product mask. Pixels falling outside the mask are background (a) re-sampled and smoothed cumulative distribution  (b) coatings distribution plot
—◇— Non-seasoned image —△— Low-seasoned image —□— High-seasoned image

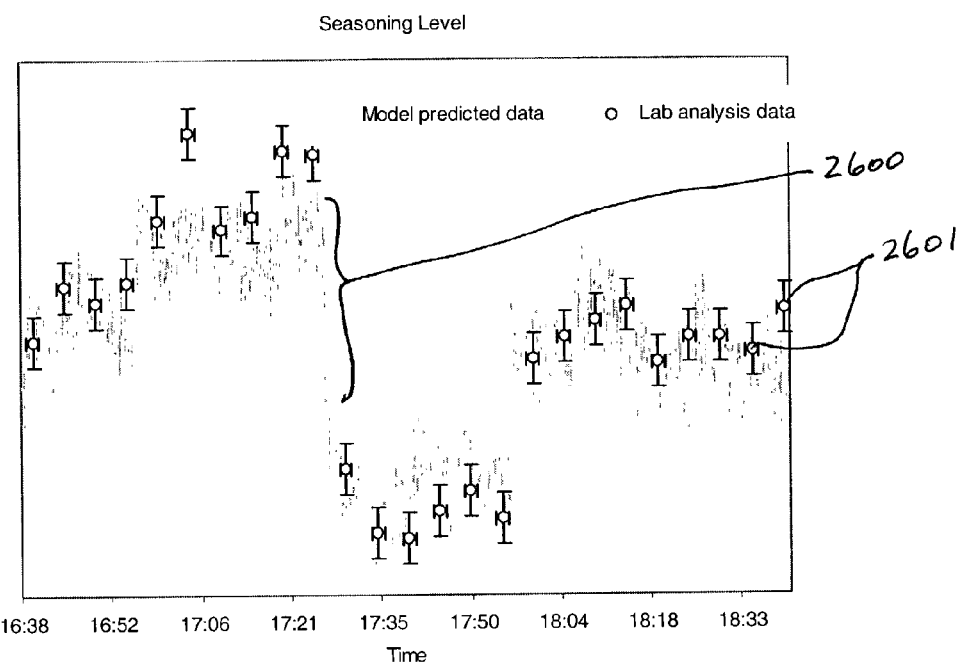
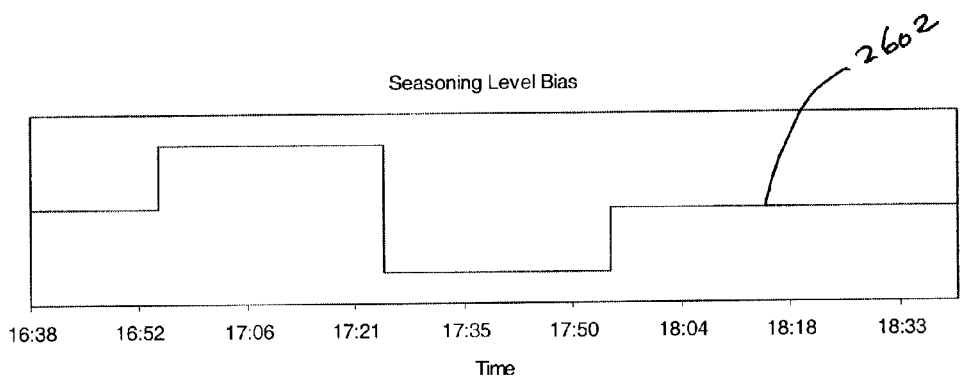
FIGURES 26-a, 26-b

Time
—— Predicted coatings level ------ Unseasoned product weight
—— Coatings slurry rate – – – – Predicted coatings distribution variance ——— Predicted coatings level    Coatings level set point
——— Unseasoned product weight    Coatings feeder speed ——— Coatings level bias

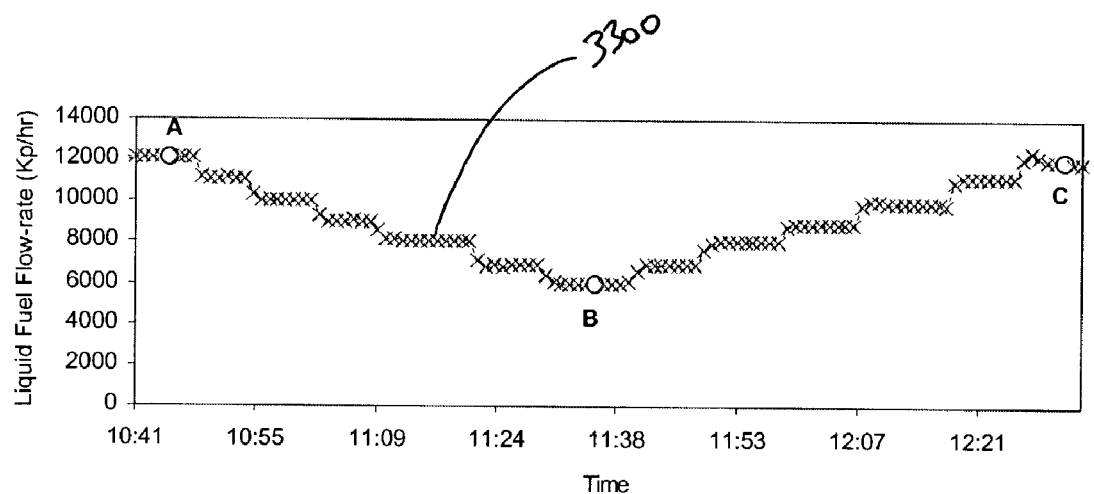
(a) Flow rate of liquid fuel (A)
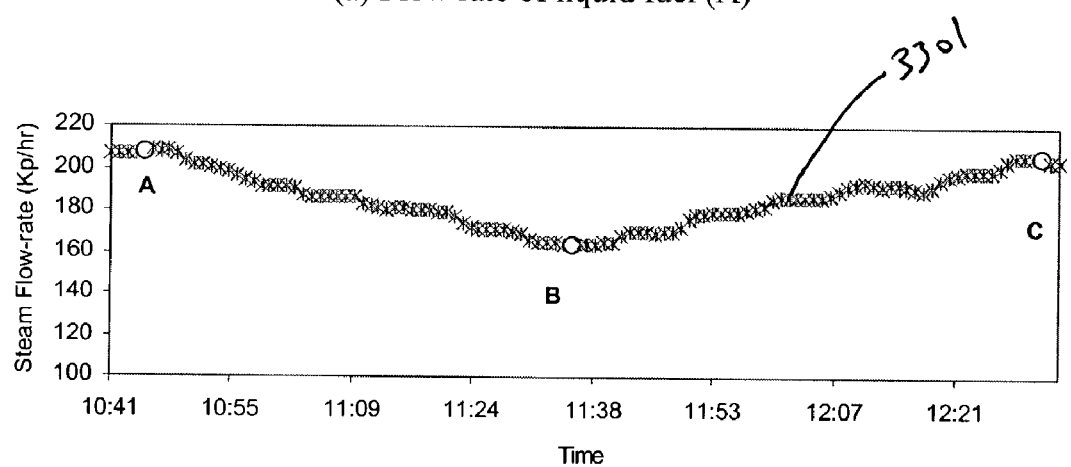
(b) Flow rate of steam generated
FIGURE 33

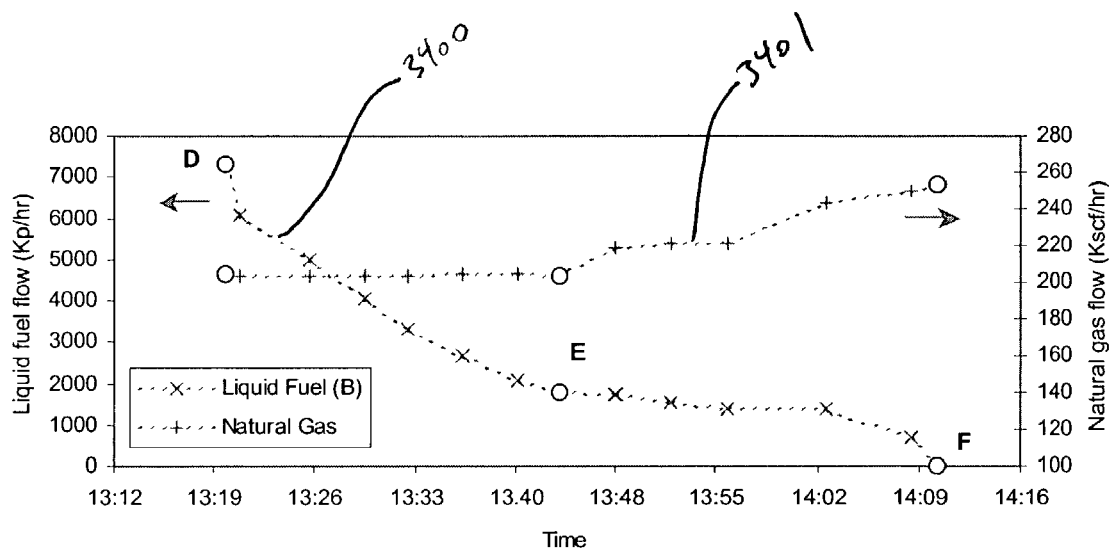
(a) Flow rate of liquid fuel (B) and Natural gas
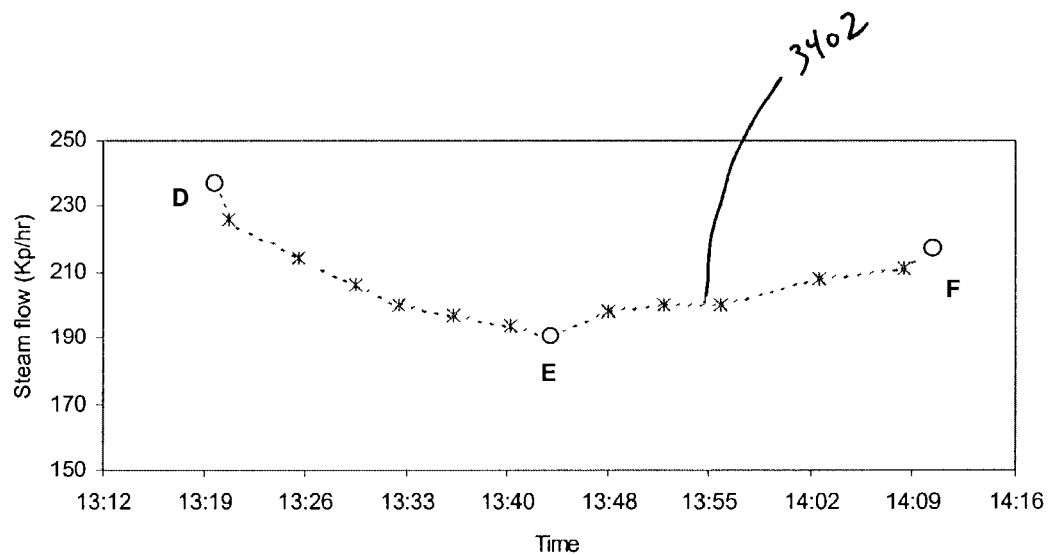
(b) Flow rate of steam generated
FIGURE 34

| Case | Point | Combustion Conditions | Sample Images | |
|---|---|---|---|---|
| I | A | Fuel (A): 12100 Kp/hr<br>Steam: 206.4 Kp/hr | 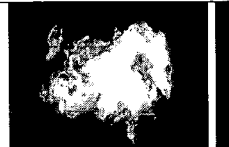 | 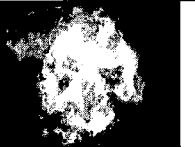 |
| I | B | Fuel (A): 6000 Kp/hr<br>Steam: 163.7 Kp/hr |  | 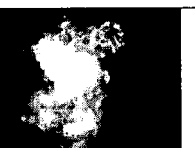 |
| I | C | Fuel (A): 12000 Kp/hr<br>Steam: 205.9 Kp/hr | 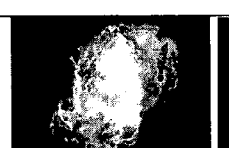 |  |
| II | D | Fuel (B): 7320 Kp/hr<br>Natural Gas: 204 Kscf/hr<br>Steam: 237 Kp/hr |  |  |
| II | E | Fuel (B): 1780 Kp/hr<br>Natural Gas: 203 Kscf/hr<br>Steam: 191 Kp/hr |  |  |
| II | F | Fuel (B): 0 Kp/hr<br>Natural Gas: 253 Kp/hr<br>Steam: 217 Kp/hr | 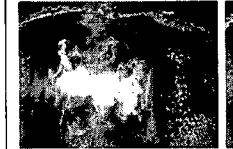 | 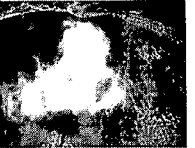 |
Figure 35-a

3600

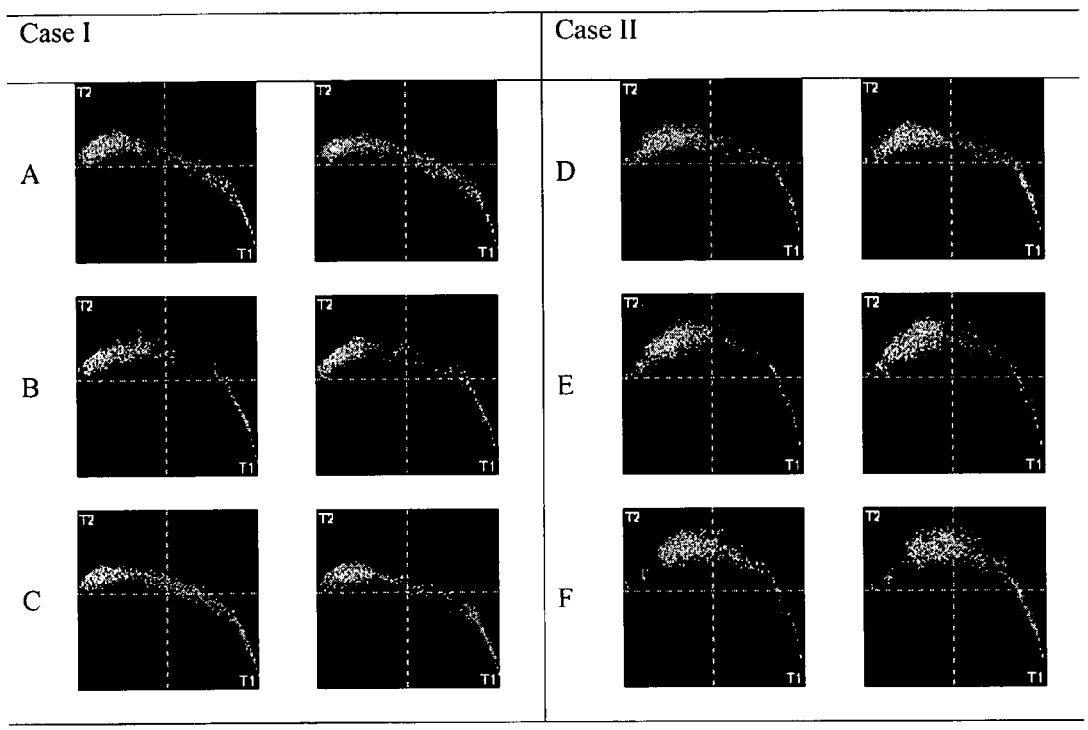
Figure 36-a (b) Score plot and mask  
(a) One sample image  
(c) The flame region decided by the mask

FIGURE 38
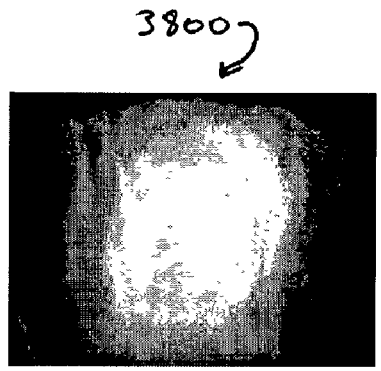
(a) An example averaged image (over 60 consecutive images)
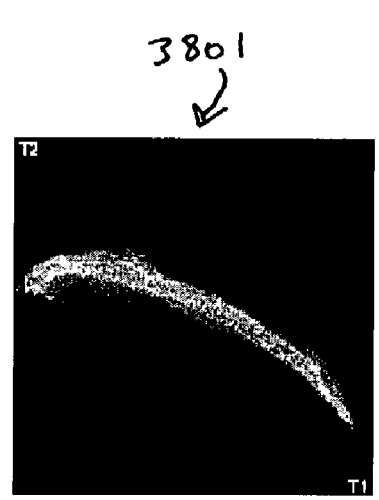
(b) The corresponding score plot

FIGURE 39
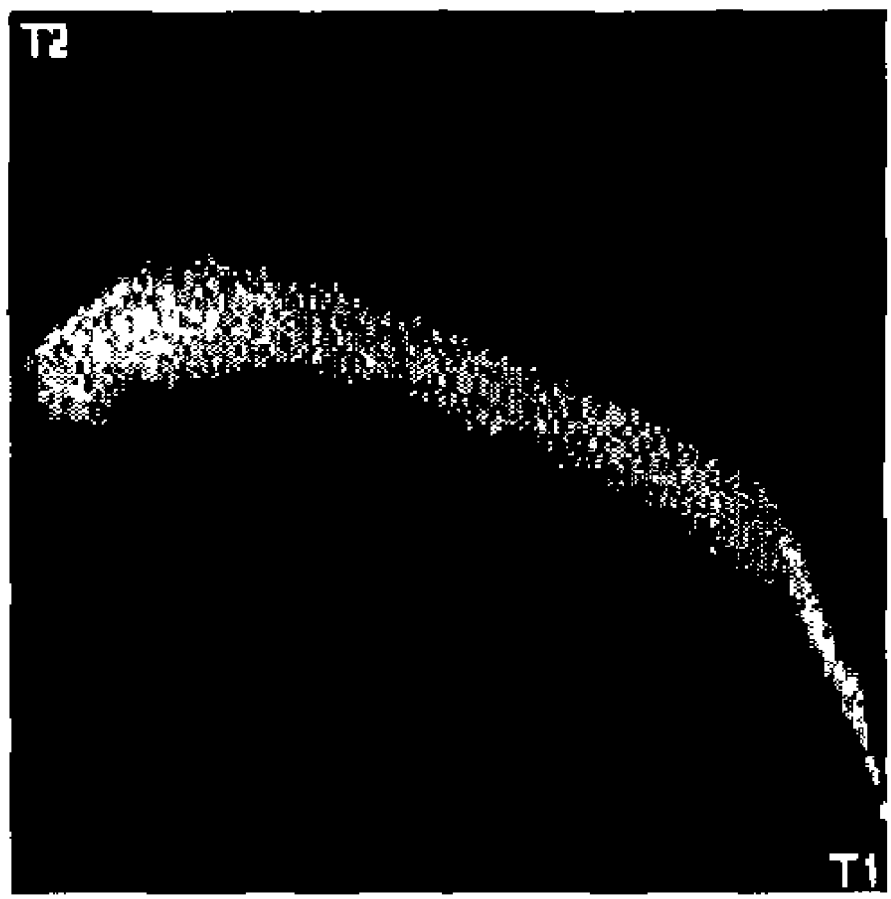
3900

(i) Total color number of flame region (i) Total color number of flame region

Figure 42 prediction power of PCA model for case I

Figure 43 loading plot of 1$^{st}$ component of PCA model for case I

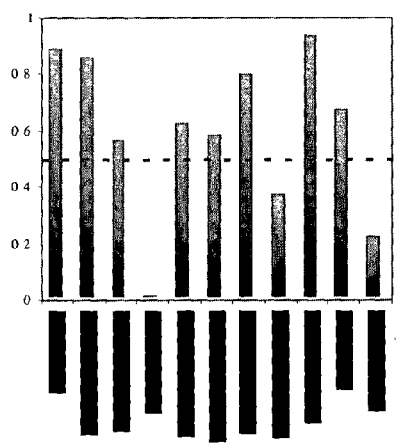 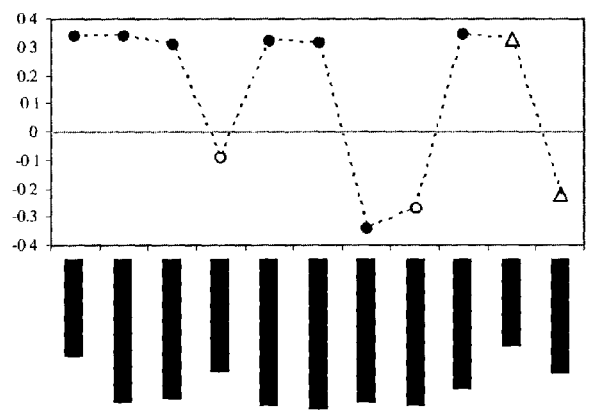
Figure 44 prediction power of PCA model for the first half data of case II
Figure 45 loading plot of $1^{st}$ component of PCA model for the first half data of case II
FIGURE 44
FIGURE 45

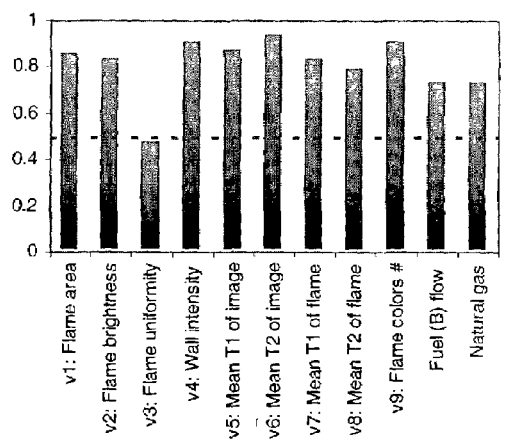 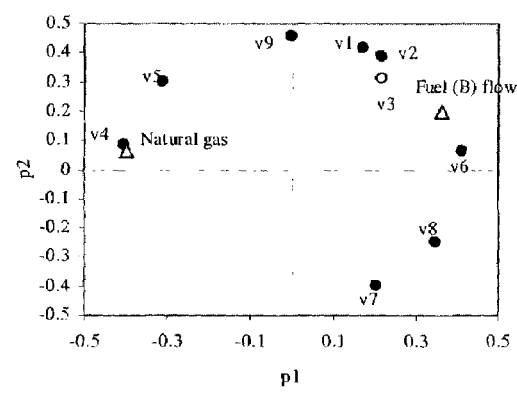
Figure 46 prediction power of PCA model for the whole data of case II
Figure 47 $p_1$-$p_2$ loading plot of PCA model for the whole data of case II
FIGURE 46
FIGURE 47

Figure 48 $t_1$-$t_2$ score plot of PCA model for both Case I and Case II

METHOD FOR ON-LINE MACHINE VISION MEASUREMENT, MONITORING AND CONTROL OF PRODUCT FEATURES DURING ON-LINE MANUFACTURING PROCESSES

BACKGROUND OF THE INVENTION

1. Technical Field

The present invention relates in part to a method for ascertaining the quantity or characteristic of a product attribute in process manufacturing, and more specifically, to determining the quality or a characteristic of a food product in the food manufacturing industry. The inventive method disclosed herein utilizes on-line machine vision technology to image a foodstuff coating and through statistical analysis predict the coating coverage based on the imaged coating concentration of the foodstuff. The methodology could be applied to the on-line measurement of any product attribute through any imaging or sensing medium where a single or multiple correlating signals can be derived.

2. Description of Related Art

The availability of inexpensive and reliable sensors for detecting product attributes while a product is moving along an assembly line or conveyor is a very important factor for successful monitoring and control in process manufacturing environments. For example, the petrochemical industry has made innovative advances in process manufacturing using multivariable modeling, in conjunction with predictive controls, due to readily available, inexpensive sensor equipment such as pressure transducers, thermocouples, and flowmeters which are easily applied to the product streams of the petrochemical industry that mainly consist of gases and liquids during the production phase.

In the past, the solids manufacturing industry encountered greater difficulty in implementing reliable sensor technology during the manufacturing phase. In its most basic form, the solids manufacturing industry used human observers to manually collate, count and determine defective products as they moved along the assembly line. Using human observers was quite expensive, prone to human error and somewhat unreliable. With the advent of digital imaging technology or "machine vision" systems, the solids manufacturing industry now has a reliable, relatively inexpensive, sensor system for monitoring and predicting selected characteristics during the production phase.

In the snack foodstuff industry, the problem of process control and quality is of great concern. Although physical observation techniques have proven somewhat effective, the problem of controlling the amount of coating applied to a foodstuff still exists in the industry. The term coatings, as used herein, may include but is not limited to, seasoning, product ingredients, or other components which are applied to the foodstuff during the manufacturing process. Product coatings may also be applied to the foodstuff in other phases of production, transportation, or distribution.

For example, topical coatings are applied to snack foods to enhance or influence their taste, colour, size, texture and nutritional content. Topical coatings are primarily applied to the foodstuff by several mechanical methods, including dusting, dry coating, spraying oil on baked goods and then dusting a coating on same thereafter. It is known in the art of coating application that the consistency of the flow of coating material to the applicator and the degree of coating adhesion to the foodstuff profoundly affect the consistency of the coatings applied to the foodstuff.

As one might imagine, reliable and consistent quality control is of paramount importance in the foodstuff, and particularly, the snack food industry. The most common prior art method of quality control is to periodically sample the product and analyze the concentration of coating in a laboratory. Unfortunately, there is usually a large time delay in between taking the sample and obtaining the concentration results. Likewise, the sample analysis procedure tends to be slow and has proven destructive to the sample itself. Moreover, the coating concentration is often not obtained directly, but determined by measuring the salt concentration of the sample operating on the assumption that the coating concentration and salt concentration remain constant, which is not always the case.

As such, a need in the art exists for a method of comparing product coatings to a desired product characteristic template and reliably predicting the characteristics of the actual product during the production phase in real-time or near real-time. Further, a need exists for a reliable and inexpensive method for assuring quality control of products manufactured on-line as the product moves from one phase of assembly to another that provides almost instantaneous monitoring and feedback control in an on-line manufacturing environment.

SUMMARY OF THE INVENTION

In accordance with one aspect of the invention there is provided a method of monitoring a process producing a characterizing product such as a snack food or a flame. The method includes the steps of sequentially capturing multivariate images of the characterizing product, each image consisting of an image array of pixel elements of measured intensity values in at least three wavelength ranges defining the dimensions for the image array. Conveniently, the wavelengths are in the visible spectrum and the pixel elements of the image array have varying intensities of the colours red, green and blue. A feature vector is created from the image array using a variety of techniques according to the nature of the process and the variables affecting the operating conditions of the process. A regression method is performed on the feature vector to correlate the feature vector with a characterizing feature of the product. The characterizing feature is displayed for continuous monitoring of the process and may define an output for feedback control of the process.

Most preferably, a multivariate statistical projection method is applied to the image array to reduce the dimensions of the array to a low dimensional score image data defined by a small number of score vectors and the feature vector is created from the low dimensional score space image data. The nature of the multivariate statistical projection used is process dependent.

In a preferred embodiment given, a multivariate statistical projection method is applied to an image array for a control process to reduce the dimensions to a low dimensional score space having a significant loading vector. The dimensions of the score space image data may also be reduced by appropriate masking of the data to exclude contributions to a score plot from background data in the images of the products of the process.

Another preferred embodiment of the present invention comprises a method for extracting specific product attribute information from a foodstuff, then predicting the quantity or characteristic of the foodstuff either directly or indirectly through additional correlation factors in an on-line environment comprising; pre-processing the foodstuff image by removing background and manufacturing apparatus features from the digital image; predicting the coating concentration of the imaged foodstuff utilizing advanced statistical regression models that relate the images to a desired product characteristic; and using the same model locally to construct a histogram of coating concentrations, a graphical image related directly to coating coverage, and provide an estimate of the spatial variance of the coating concentration. The present invention extends to using the constructed model and real-time image data to predict the quantity, characteristic, and variance of the measured food product attribute and to generate a measurement signal; using the measurement signal to adjust the manufacturing process and control the process to deliver the desired product quality consistently; and furthermore, using the measurement signal in conjunction with other process measurements to predict additional product attribute characteristics not measured directly by a sensor.

The above, as well as additional features and advantages of the invention will become apparent in the following written detailed description.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

FIG. 1-a is a table setting forth sample images of products with various seasoning coating concentrations;

FIGS. 16-a through 16-d are graphical depictions of the estimated coating concentration for each histogram bin calculated according to methods 3, 4, 5 and 6 according to one embodiment of the inventive method disclosed herein;

FIGS. 26-a and 26-b is a depiction of the open-loop response of the seasoning level caused by changing seasoning level bias according to one embodiment of the inventive method disclosed herein;

FIGS. 33-a and 33-b graphically depict the flow rate of liquid fuel (A) and steam flow rate over time for case I;

FIGS. 34-a and 34-b are graphical depictions of the flow rate of liquid fuel (B) and steam flow rate over time for case II;

FIG. 35-a is a series of sample images corresponding to the points (A~F) as shown in FIG. 33 and FIG. 34;

FIG. 36-a depicts the corresponding score plots for the sample images shown in FIG. 35-a;

FIGS. 38-a and 38-b show an averaged image (over 60 consecutive images) and the corresponding score plot;

FIG. 39 is an averaged score plot of the flame image in FIG. 38-a in a $t_1$ $t_2$ score space;

FIG. 44 is a bar graph showing the prediction power of the PCA model for the first half of the data for case II;

FIG. 45 is a loading plot of the 1$^{st}$ component of the PCA model for the first half of the data for case II;

FIG. 46 is a bar graph showing the prediction power of the PCA model all the data for case II;

FIG. 47 is a loading plot of the 1$^{st}$ component of the PCA model for all the data for case II;

DETAILED DESCRIPTION OF THE INVENTION

Food Coating Analysis Embodiment

One embodiment of the inventive method disclosed herein consists of utilizing known digital imaging technology to image and process digital images of coatings on foodstuffs, as the foodstuffs are moving on-line extract desired features from the image, then constructing a model that predicts the characteristic level on the imaged product by relating the pre-processed product images to a desired product characteristic via MultiVariate Image Analysis (MIA) or other statistical regression regimes, and locally constructing a histogram that depicts the correlation of coating concentration to coating coverage. In a preferred embodiment, the inventive method disclosed herein is applied to quality and control processes in the food manufacturing industry and, more specifically, to determine the seasoning coating applied to snack foods in the food processing industry.

Traditional image analysis methods are known in the art with respect to a variety of applications in the food industry, such as fruit and vegetable sorting, automatic partitioning, inspection for foreign matter or objects, and general packaging applications. However, digital imaging applications pertaining to coating on food items are virtually nonexistent. With regard to the digital imaging component of the inventive method disclosed herein, much of the literature on digital imaging processing involves methods for altering the visual image in some way to make the image more visually appealing or to extract information on the shapes, boundaries or location of various observable features. In this vein, traditional image processes serve as automated, machine vision systems performing operations many times faster and far more precisely than human observers or operators.

Most foods typically are produced by coating the base product with flavored coatings. Coatings plays an important role in both the flavor and the appearance of a food or snack, and greatly influences their acceptability. The usual procedure of taking infrequent samples and analyzing for the coatings concentration in the laboratory yields very little information, except long term trends and with no information on the food coating distribution. Furthermore, laboratory analysis is a time-consuming and expensive procedure. Clearly there is a tremendous opportunity for an on-line imaging system.

Figure 1:
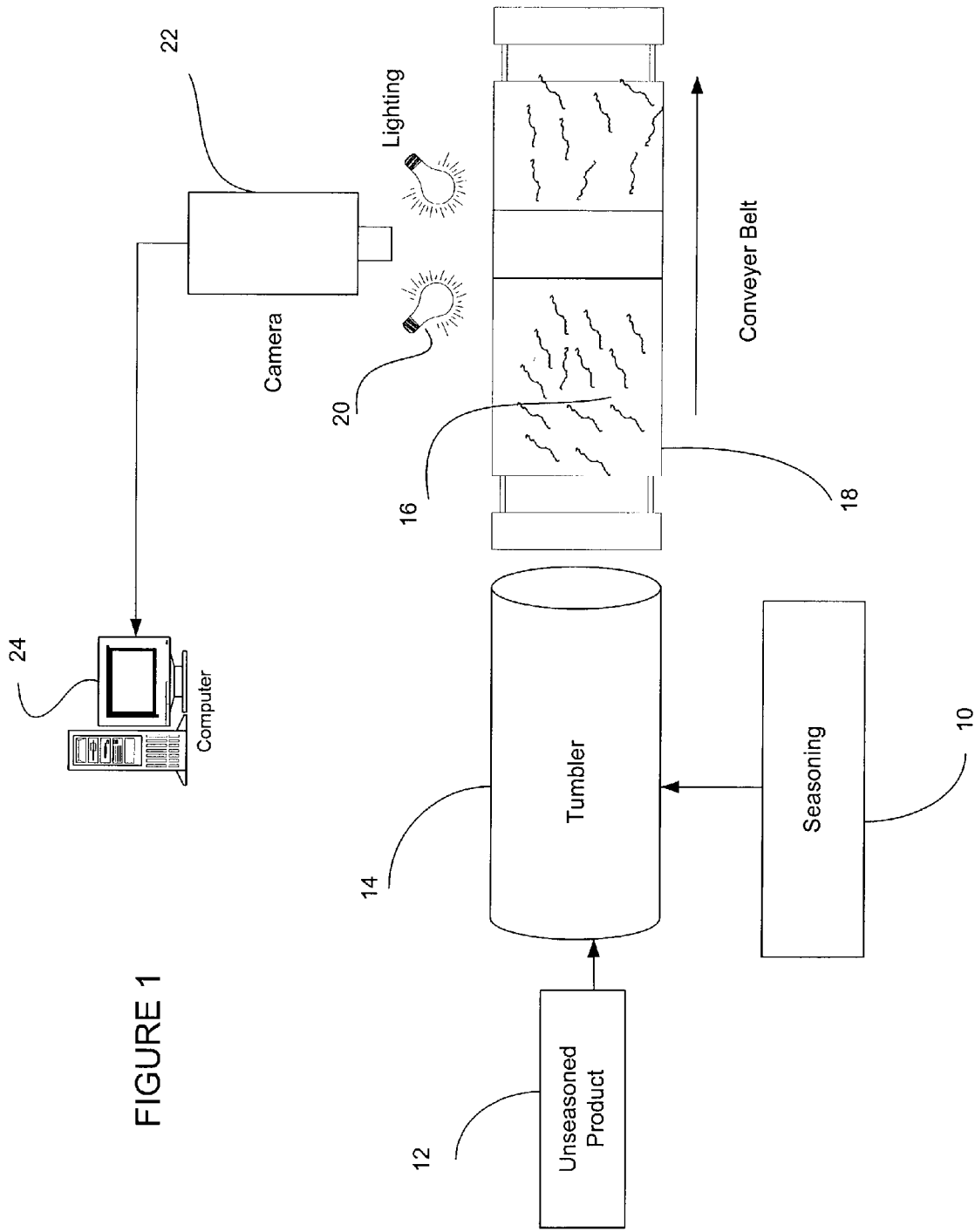
FIG. 1 is a schematic diagram depicting a preferred embodiment of the present invention integrated into an on-line food manufacturing environment according to one embodiment of the inventive method disclosed herein.

A typical setup for using imaging technology in a food manufacturing environment is shown in FIG. 1. Coatings 10, in this example "seasoning," and unseasoned food product 12 are mixed in a tumbler 14 and then the coated food product 16 is conveyed via a moving belt 18 to subsequent operations such as packaging or baking. An electromagnetic radiation source, in this example a visible spectrum lighting system 20, and RGB camera system 22 are mounted above the moving belt 18 and images of the products 16 are sent to a computer 24 for analysis by the methods disclosed herein. The electromagnetic radiation source 20 could also be configured to emit radiation from the various bands of the electromagnetic spectrum, including but not limited to, the infrared spectrum and ultraviolet spectrum and be configured to emit single and multiple wavelengths of electromagnetic radiation in the desired spectrum. The choice of sampling interval depends upon the objectives for each process. The time required for processing one image of product 16 was less than a second.

The inventive method disclosed herein could also find application in determining other foodstuff qualities such as the number of toast points located on the product, the texture of the product, and/or the number of blisters on the product. Likewise, it will be appreciated that the inventive method disclosed herein will find applications in various other industries as will be exemplified. Another embodiment applying the inventive principles of multivariate image analysis with application toward flame study is also discussed herein. Thus, the specification, claims and drawings set forth herein are to be construed as acknowledging and non-exclusionary as to these other applications and embodiments.

The RGB (red-green-blue) space is the most commonly used colour space in electronic cameras, in which the colour of each pixel is characterized by the numerical values (normally integers from 0 to 255) of its R, G and B channels. A colour image can be expressed as a 3-way matrix. Two dimensions represent the x-y spatial coordinates and the third dimension is the colour channel. Without considering the spatial coordinates of pixels, we can unfold the image matrix and express it as a 2-way matrix.

$$I_{N_{row} \times N_{col} \times 3} \xrightarrow{unfold} I_{N \times 3} = \begin{bmatrix} c_{1,r} & c_{1,g} & c_{1,b} \\ M & M & M \\ c_{i,r} & c_{i,g} & c_{i,b} \\ M & M & M \\ c_{N,r} & c_{N,g} & c_{N,b} \end{bmatrix} = \begin{bmatrix} c_1 \\ M \\ c_i \\ M \\ c_N \end{bmatrix}$$

$\underline{I}$ is three-way image matrix with image size $N_{row} \times N_{col}$. I is the unfolded two-way image matrix. N is the number of pixels in the image, $N=N_{row} \times N_{col}$. $c_{i,r}$, $c_{i,g}$, $c_{i,b}$ (i=1, ... ,N) are the intensity values of the R, G and B channels for pixel i. $c_i$ (i=1, ... ,N) is the i-th row vector of I, which represents the colour values of pixel i. In the following text, we always use the two-way matrix I to represent an image.

It is known that several factors may influence the colour of a pixel-size seasoned foodstuff. The colour of a pixel would be decided by the colour of the non-seasoned part, the colour of the coatings particles, the concentration of coatings and the lighting condition of this piece of product. If these factors, other than coating concentration, are lumped together into one factor $\phi$, which we shall refer to as the imaging condition, the colour of one pixel $c_i$ can be expressed as function of the local imaging condition $\phi_i$ and local coatings concentration $y_i$.

$$c_i = f(y_i, \phi_i) \qquad (1)$$

Figure 2:
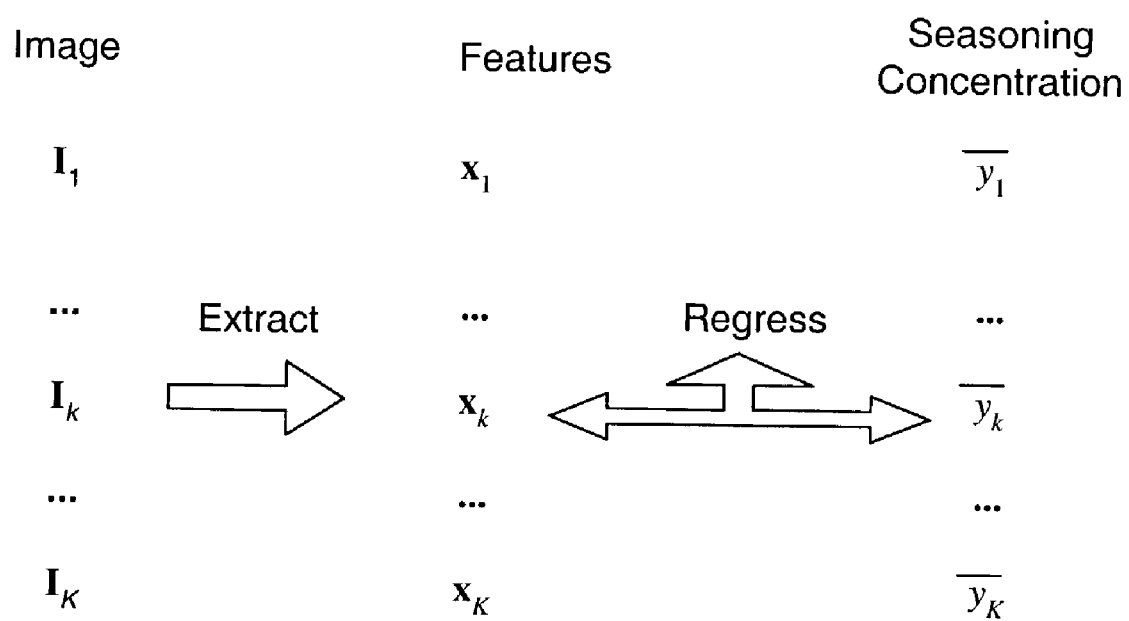
FIG. 2 is a schematic diagram which depicts the fundamental model for imaging a food product, extracting image features, and performing a statistical regression to determine the coating concentration according to one embodiment of the inventive method disclosed herein.

FIG. 2 represents the schematic model depicting the determination of coating on a foodstuff via regression analysis. For example, consider a data set of K colour images $I_k$ and their corresponding laboratory analyzed average coatings concentration $\bar{y}_k$ (k=1, ... ,K). A model to predict coatings concentration can be obtained by regressing the coatings concentrations against the features extracted from image. Feature extraction converts the image into a feature vector that contains information most related to coatings concentration, and is therefore, a critical step to achieve desired prediction results. After feature extraction, a model is developed by regressing feature variables and coatings concentration. Different regression methods may be used, including Principal Component Regression (PCR), Multivariate Linear Regression (MLR) and Artificial Neural Networks (ANN). In the preferred embodiment, Partial Least Squares (PLS) regression is employed because of the high correlation among the feature variables.

MPCA (Multi-way Principal Component Analysis)

A colour image is a multivariate image composed of three variables (R, G and B channels). The inventive herein method is developed using Multivariate Image Analysis (MIA) techniques, which are based on multi-way Principle Component Analysis (PCA). Multi-way PCA is equivalent to performing PCA on the unfolded image matrix I.

$$I = \sum_{a=1}^{A} t_a p_a^T$$

where A is the number of principal components, the $t_a$'s are score vectors and the corresponding $p_a$'s are loading vectors.

Since the row dimension of the I matrix is very large (equal to 307,200 for a 480*640 image space) and the column dimension is much smaller (equal to 3 for an RGB colour image), a kernel algorithm is used to compute the loading and score vectors. In this algorithm, the kernel matrix ($I^T I$) is first formed (for a set of images, kernel matrix is calculated as $$\sum_k I_k^T I_k),$$

and then singular value decomposition (SVD) is performed on this very low dimension matrix (3*3 for colour image) to obtain loading vectors $p_a$ (a=1, ... A).

After obtaining loading vectors, the corresponding score vectors $t_a$ are then computed via $t_a = I p_a$. Since the first two components normally explain most of the variance, instead of working in original 3-dimensional RGB space, working in the 2-dimensional orthogonal $t_1$–$t_2$ score space allows the images to be more easily interpreted.

Datasets

When building the model of the embodiment discussed below, the first step is to collect an adequate set of datasets. A successful model requires a set of sample images including both non-seasoned and seasoned product samples with varied coatings levels. For each seasoned product image, the corresponding average coating is obtained by laboratory analysis. All the images are collected from the on-line camera system and grab samples corresponding to those images are taken to the lab for analysis. The images are all 480×640 RGB colour images, with 256 intensity levels in each channel. Some sample images are shown in FIG. 1-a, together with details on the size of the training and test datasets for each product. The datasets include both non-seasoned and seasoned product samples (coatings levels are varied) which are initially imaged by digital imaging equipment. For each seasoned product image, the corresponding average coating is obtained by laboratory analysis.

To illustrate a preferred embodiment of the method disclosed herein, three samples of snack chips (products A, B and C) were collected, imaged and their seasoning concentrations obtained in laboratory analysis. Samples of product A were collected off of the manufacturing line (off-line), while samples of product B and product C were collected while located on the manufacturing line (on-line). All imaged samples were taken with digital imaging equipment and were 480×640 RGB colour images, with 256 intensity levels in each channel. Half of the samples were used as the training set and the other half as a test set. Sample images and additional information about the product samples is found in FIG. 1-a.

Feature Extraction Methods

Table 1 contains six image feature extraction methods that can be utilized by the inventive method disclosed herein. These methods can be further classified into two categories: overall feature methods and distribution feature methods. In following explanation, product C is used as the example to illustrate the six feature extraction methods.

TABLE 1

Methods of Feature Extraction

| | Method # | Feature variables |
|---|---|---|
| Overall Feature Methods | 1 | Average colour |
| | 2 | Loading vector of 1st principle component |
| Distribution Feature Methods | 3 | Two-dimensional histogram in t1–t2 score space |
| | 4 | Histogram based on linear projection in t1–t2 space |
| | 5 | Cumulative histogram based on linear projection in t1–t2 space |
| | 6 | Cumulative histogram based on correlation property segmentation |

Overall Feature Methods

In these types of methods, information from all pixels is used to obtain some overall colour feature. Two methods are presented: method 1 (average colour) and method 2 (1st loading vector from PCA). In both methods, the dimension of the feature vector is three, one element for each of the three colour channels. Since colour is a function of coatings concentration, the overall colour features will be correlated with the average coatings concentration. Models can be further built based on this correlation relationship.

Method 1: Average Colour

Average colour is a straightforward way to extract features. In this method, the feature variables are just the average values for each channel taken over the whole image.

Method 2: Loading Vector of 1st Principal Component

When performing a PCA (without mean-centering) on an image, the $1^{st}$ loading vector represents the direction of greatest variability of the pixel intensities in the RGB colour space. As can be verified in the examples, the $1^{st}$ principal component of PCA (without mean-center) explains most of the variance (over 97%). Therefore, it is also a good overall descriptor of the image colour and can be used as a feature variable.

Figure 3:
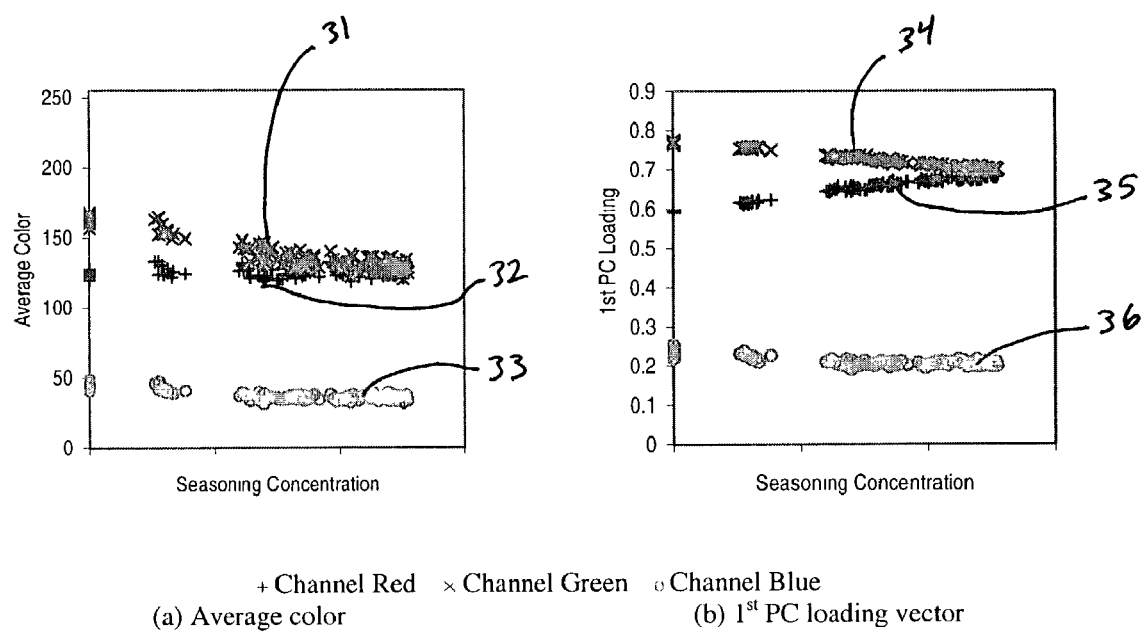
FIGS. 3-a and 3-b are graphical depictions of the relation between product seasoning concentration versus average colour of the product and the first principal component loading vector, respectively.

FIG. 3 demonstrates the relation between average colour, first principal component loading vector and the seasoning coating concentration features. Green channel data points 31, red channel data points 32, and blue channel data points 33 are shown in the FIG. 3-a plotted as seasoning concentration versus average colour. Green channel data points 34, red channel data points 35, and blue channel data points 36 are shown in FIG. 3-b plotted as seasoning concentration versus first principal loading component (PC) loading vector. Regression models using these features may then be developed based on feature versus concentration data.

As shown in equation (1), the colour of a pixel is a function of both the local coating concentration and other imaging conditions. Although pixels containing the same amount of coating concentration may exhibit variations in colours, it is reasonable to assume that pixels having the same colour contain the same amount of coating. For an image, the number of pixels, whose colour is [r g b] (r, g and b are integer from 0 to 255), can be counted as $n_{[r,g,b]}$. If the coatings concentration for each of these pixels is $y_{[r,g,b]}$, then the average coatings concentration for the whole image can be calculated as:

$$\bar{y} = \sum_r \sum_g \sum_b y_{[r,g,b]} \frac{n_{[r,g,b]}}{N} \quad r, g, b = 0, 1, \ldots, 255 \quad (2)$$

Notice that equation (2) has a linear model structure. For each image, $n_{r,g,b}/N$, which is a 256×256×256 three dimensional relative histogram, can be used as feature variable. Estimation of $y_{[r,g,b]}$ can be obtained through a linear regression between the observed values of $n_{r,g,b}/N$ from the images and average coating concentration from laboratory analysis. However, this model is neither robust nor practical because to obtain such a 3-D histogram for each image is time consuming and even if the three dimensional histogram is computed, the large number ($256^3$=16,777,216) of feature variables are extremely highly correlated and generally have a very low signal-to-noise ratio. This leads to a very ill-conditioned and poor model for predicting the average coatings level.

To reduce the number of feature variables, we can divide the colour space into L classes, such that pixels falling in a class contain a similar amount of coatings. In this form, each class becomes a new histogram bin and the average coatings concentration for an image can be obtained by:

$$\bar{y} \approx \sum_{j=1}^{L} y_j \frac{n_j}{N} \quad (3)$$

where $n_j$ and $y_j$ are the pixels and average coating concentration belonging to class j. The model structure remains linear as long as the assumption that pixels in the same class represent a similar amount of coating is not flagrantly violated.

There is a strong relationship between the average colour and the 1st loading vector of MPCA as used in the overall method 1 and 2 respectively. In method 2, a non-mean-centered PCA is performed on each image and $1^{st}$ principal component explains most of the variation. In this situation, the direction of average colour $\bar{c}$ is approximately equal to the direction of $1^{st}$ loading vector $p_1$.

$$\overline{c} \cdot p_1 \approx \|\overline{c}\| \Rightarrow p_1^T \approx \frac{\overline{c}}{\|\overline{c}\|}$$

Therefore, the $1^{st}$ loading vector is approximately equal to normalized average colour and instead of $1^{st}$ loading vector or MPCA, the normalized average colour could be used as feature variables and should give a similar performance as method 2.

Lighting variations will have an influence on the overall feature methods. Lighting variation comes from a non-uniformly distributed light source, a non-flat orientation of the product, or overlapping among the pieces of product. Suppose that the lighting condition and colour has the following linear relationship for each pixel location:

$$c_i = L_i R_i, i = 1, \Lambda, N$$

in which, $c_i$, $L_i$, $R_i$ are colour, local lighting condition and colour under an ideal reference lighting condition for pixel i.

Assume the light source and the image scene are independent. The average colour of an image is equal to $$\overline{c} = \overline{L} * \overline{R}$$

Any variation in lighting will directly influence the value of average colour. Since the $1^{st}$ loading vector is approximately the normalized colour, then $$p_1^T \approx \frac{\overline{c}}{\|\overline{c}\|} = \frac{\overline{L} \cdot \overline{R}}{\|\overline{L} \cdot \overline{R}\|} = \frac{\overline{R}}{\|\overline{R}\|}$$

Therefore, this lighting effect is canceled when using the $1^{st}$ loading vector or normalized average colour. In section 3.1, test set images have similar overall lighting conditions as the training set images, and so both method 1 and method 2 obtain good prediction results. But when using small image windows as test images as in section 3.2, lighting conditions vary from window to window. Since method 2 is less sensitive to lighting variation, it more often than not will have a smaller prediction error than method 1. However, the deduction above is based on a linear effect of lighting, which may not always exist in reality. Therefore, method 2 is still influenced by lighting condition variation and shows increasing prediction error when window number increases.

Distribution Methods

Models based on distribution features have an advantage over the overall feature models, in that information from every class is taken into account rather than using only a global description of the image. Distribution feature models are pixel-level models. This means that in distribution feature models, regression coefficients are the estimates of the coatings concentration for each bin.

$$y = \hat{y}_{Bin_1} x_1 + \hat{y}_{Bin_2} x_2 + \Lambda + \hat{y}_{Bin_B} x_B$$

For one pixel with colour value c, if it is determined that this pixel is falling into $i^{th}$ bin, the coating concentration for this pixel can be estimated as $\hat{y}_{Bin_i}$. Therefore, distribution feature models can be seen as pixel-level models because we can estimate the coating concentration for each pixel.

Three different methods are now presented to divide the colour space pursuant to the distribution models discussed below. In each method, MPCA is first performed to reduce the dimension and all the operations are then carried out in the t1–t2 score space. As discussed in further detail below, method 3 uses a simple 32×32 two-dimensional histogram in t1–t2 score space. Methods 4 and 5 are based on a one-dimensional histogram and a cumulative histogram, respectively, obtained by a further linear projection in t1–t2 score space. Method 6 begins with a fine 256×256 two-dimensional histogram in t1–t2 space, then combines the histogram bins having similar coatings based on covariance properties and a new one-dimensional cumulative histogram is eventually used as the feature vector.

Method 3: Two-Dimensional Histogram in t1–t2 Score Space

Figure 4:
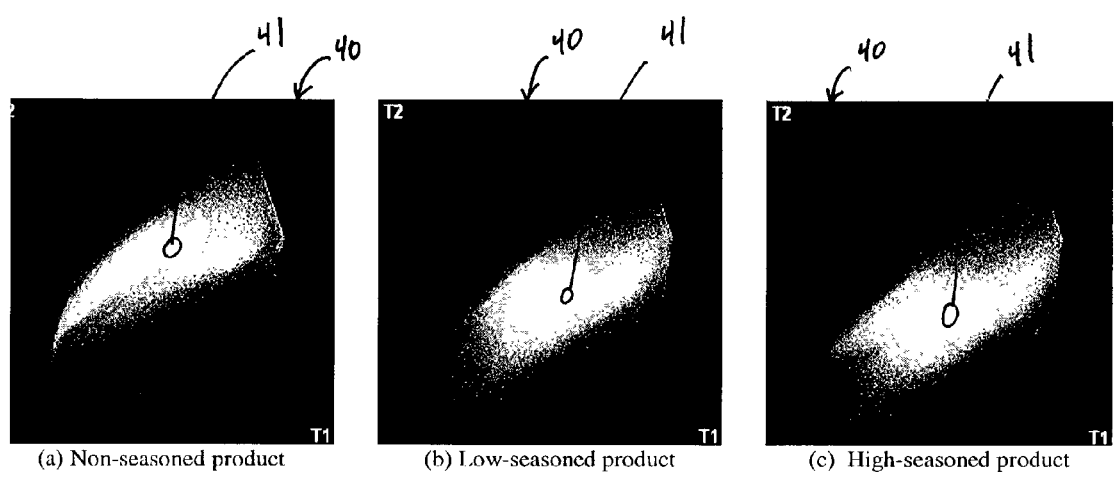
FIGS. 4-a, 4-b and 4-c are image score plots for three separate images of a non-coated, low-coated, and high-coated foodstuff according to one embodiment of the inventive method disclosed herein.

One effective way to reduce the number of histogram bins is to perform MPCA on training images and find a t1–t2 plane that contains most of the information. The images are corrected by subtracting the average colour of non-seasoned product images in order to obtain a plane that captures most of the difference between coated and non-coated product. Three scatter score plots (t2 vs. t1) of three sample images of product C (Non-, low- and high-coated product as shown in Table 1) are illustrated in FIGS. 4-*a*, 4-*b*, and 4-*c*. Since similar colours in the original image will yield almost identical (t1,t2) score combinations, many points overlap in this scatter plot. Following Geladi et. al. ("*Multivariate Image Analysis*" 1996, Wiley, New York, 1996), the score plots (t1 vs. t2) are constructed as two dimensional histograms with a grid of 256×256 bins. This two dimensional histogram is then colour-coded depending upon the number of pixels in each bin using a colour scheme ranging from dark colours 40 (e.g. black) representing bins with a low number of pixels to light colours 41 (e.g. white) representing bins having the highest pixel density. From these plots, it is observed that the position of pixels in the score space strongly correlates with coating concentration.

Figure 5:
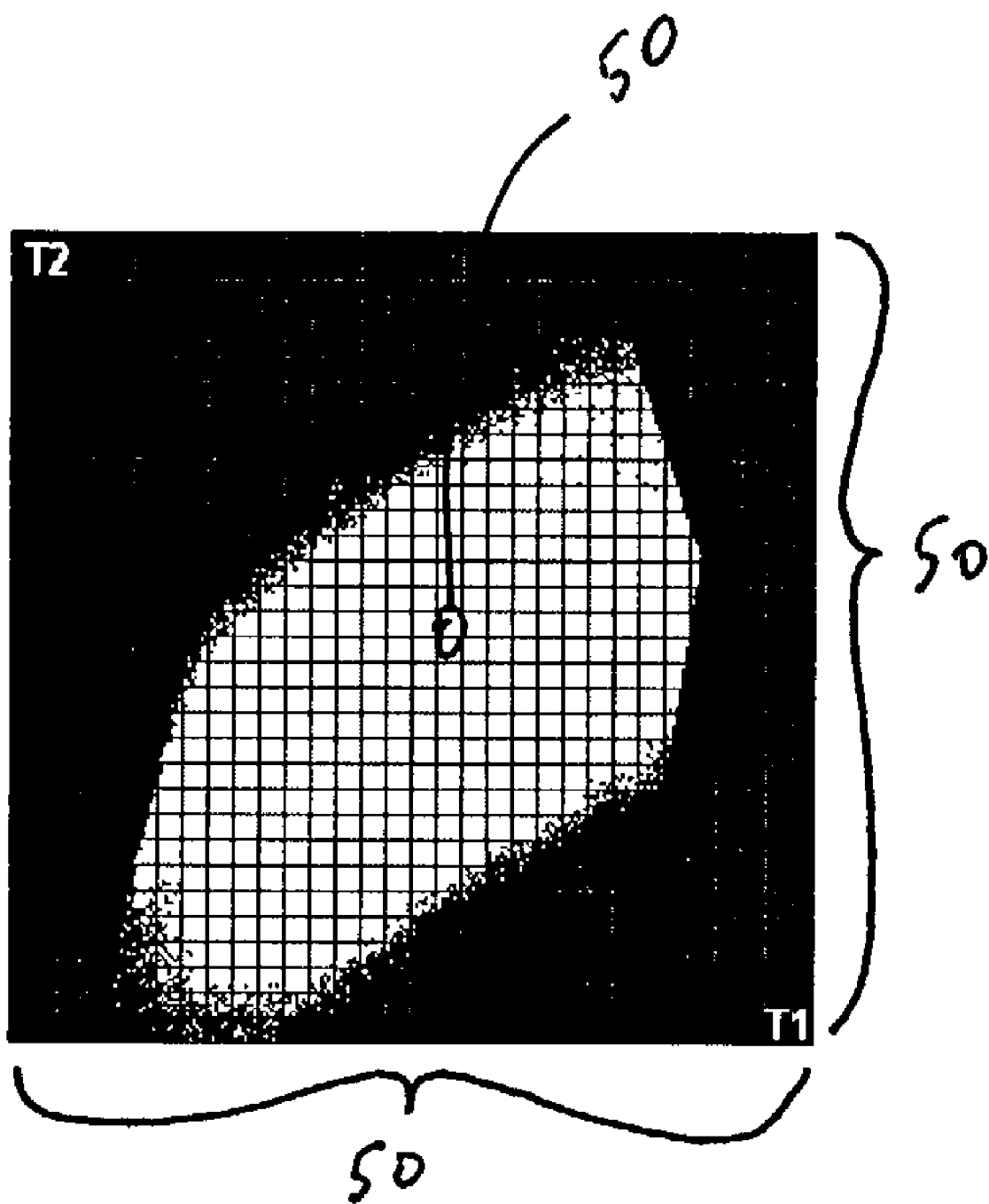
FIG. 5 represents a one dimensional histogram constructed by taking an image score plot and dividing it into 32×32 blocks for use in developing a feature vector for each image according to one embodiment of the inventive method disclosed herein.

In the t1–t2 space, if we divide each score variable into only 32 bins, the number of final bins would be reduced to $32^2 = 1,024$. Though it is still a large number, it is much less than in three-dimensional space ($32^3 = 32,768$) or directly using the score plot ($256^2 = 65,536$). The number of bins can be further reduced by simply dividing the score variables into fewer bins and enlarging the bin size; however, at some point, the precision may begin to degrade. The 32×32 two-dimensional histogram can be unfolded into a row vector and used as feature vector for each image. This method is equivalent to dividing t1–t2 score plots into 32×32 blocks and summing the intensity values within each block as illustrated in FIG. 5. The white pixels 50 indicate the location of pixels for all the training images.

Method 4 and 5: One-Dimensional Histogram/Cumulative Histogram Based on a Linear Projection in t1–t2 Plane The (32×32) two-dimensional histograms still have many bins which may lead to an ill-conditioned regression. Furthermore, not all shifts of the histogram in the t1–t2 space will be related to coating concentration changes.

Figures 6, 7:
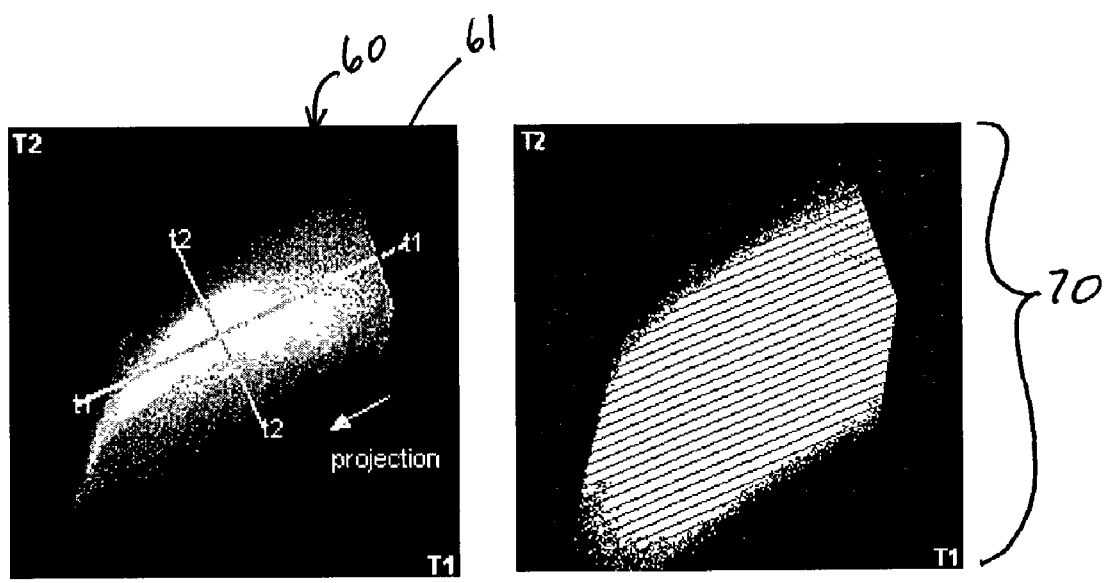
FIGS. 6 and 7 illustrate an alternative approach to divide an image score plot by creating a cumulative histogram based on vector projection according to one embodiment of the inventive method disclosed herein.

The dimension can be reduced to one by finding a projection direction in the t1–t2 space, along which the variation of colour is caused mainly by imaging condition changes rather than coating concentration changes. One approach to find such a direction is to perform another PCA on only non-coated product images (i.e. a control process) in the t1–t2 space. In non-coated product images, all the colours represent equivalent coating concentration and the 1$^{st}$ component of this PCA would indicate the direction that has most variation caused by changing imaging conditions and changing base product colour. The first component is therefore the significant loading vector $t_s$. Projection of all the histogram bins along this direction will cancel out most of the influential imaging condition variations if the PCA model has been built on a training set of non-coated product images which is representative of the variations one normally would encounter. After projection, a one dimensional histogram can be obtained (Method 4). A cumulative histogram can also be used as feature variables to describe the distribution that will normally have a better signal to noise ratio than the one-dimensional histogram alone (Method 5). FIGS. 4-a, 4-b and 4-c are examples of score plot one-dimensional histograms based on a linear projection in the t1–t2 plane acquired from three sample images of product C. FIG. 5 depicts the division of the score plot into 32×32 histogram bins 51. FIGS. 6 and 7 illustrate this projection approach.

Figure 8:
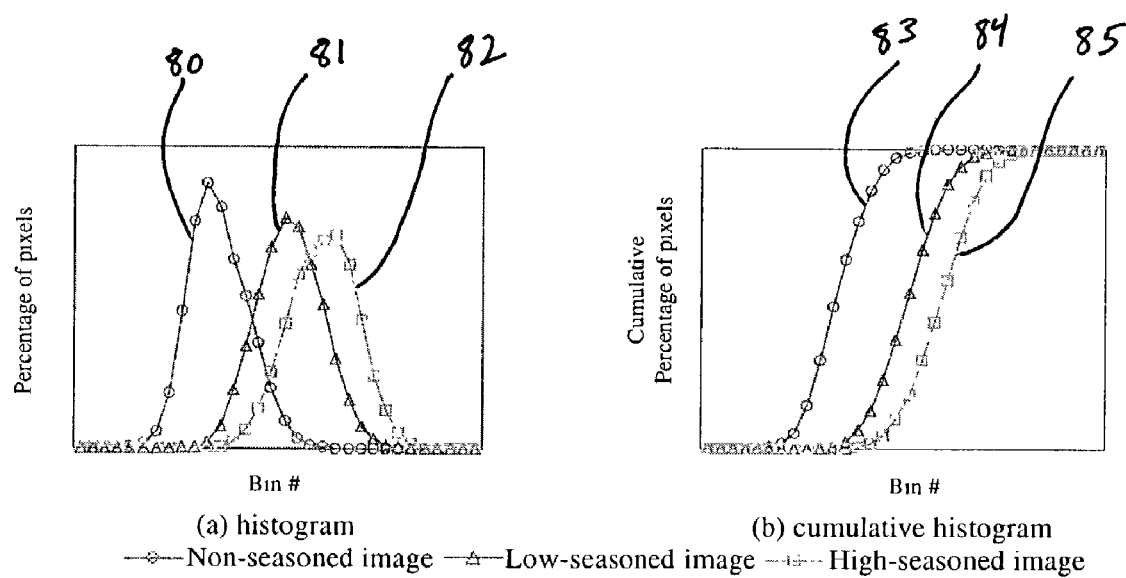
FIGS. 8-a and 8-b are graphical representations of the one dimensional histogram and cumulative histogram points, respectively, obtained for each analyzed non-seasoned image, low-seasoned image and high-seasoned image according to one embodiment of the inventive method disclosed herein.

To find the parallel line direction for the bins 51, another PCA (mean-centered) is performed on the t1–t2 score data of the non-coated product images 60 as shown in FIG. 6. In FIG. 7, contrary to method 3 previously discussed, the t1–t2 space is divided into long parallel bins 70. The first component direction in this space ($t_1$—$t_1$ line 61 in FIG. 6) indicates the direction of largest variance which is due mainly to imaging condition changes. For each training image, the pixels are first projected onto the t1–t2 plane using the MPCA model for the training images. Then the scores are projected along the first component direction obtained from the PCA performed on the non-coated image score plot. In this way, the original three-dimensional RGB space is simplified to only one dimension. The one-dimensional histogram for non-seasoned images 80, low seasoned images 81, and high seasoned images 82 (according to method 4) and cumulative histogram for non seasoned images 83, low seasoned images 84 and high seasoned images 85 (according to method 5) can be computed and plotted as shown in FIGS. 8-a and 8b where 32 bins are used. The 32 histogram and cumulative histogram points obtained for each image are then used as features to regress against the average coating content for these images.

Method 6: Cumulative Histogram Based on Correlation Property Segmentation

In methods 4 and 5, a linear projection is used to convert the two-dimensional histogram into a more robust one-dimensional histogram. However, linear projection may not achieve very reliable results because imaging conditions often have a nonlinear influence on pixel colour.

In method 6, a 256×256 histogram in t1–t2 space is created, in methods 4 & 5, and then combine histogram bins that are expected to contain similar amount of coating concentration into a class by calculating the covariance properties between the histogram elements and coating concentration.

For image I, we can express its relative histogram as:

$$P_I = [P_I(B_1) P_I(B_2) \wedge P_I(B_M)]$$

M is the total number of histogram bins. For a 256×256 histogram in t1–t2 space M equals to $256^2 = 65,536$. $P_I(B_i)$ is the pixel counts for bin $B_i$ divided by the total number of image pixels, which is an estimation of probability of pixels falling into the $i^{th}$ bin.

A matrix $\Gamma$ can be constructed by stacking relative histograms for all the training images together:

$$\Gamma = \begin{bmatrix} P_{I_1} \\ P_{I_2} \\ M \\ P_{I_K} \end{bmatrix} = \begin{bmatrix} P_{I_1}(B_1) & P_{I_1}(B_2) & \wedge & P_{I_1}(B_M) \\ P_{I_2}(B_1) & P_{I_1}(B_2) & \wedge & P_{I_2}(B_M) \\ M & M & O & M \\ P_{I_K}(B_1) & P_{I_1}(B_2) & \wedge & P_{I_K}(B_M) \end{bmatrix} =$$

$$[P(B_1) \; P(B_2) \wedge P(B_M)]$$

$P(B_i)$ is the $i^{th}$ column vector of matrix $\Gamma$ for each bin $B_i$.

The 256×256 histogram in t1–t2 space is preferred, which equates each histogram bin as representing pixels with similar colour and similar coating content. To combine histogram bins with similar coating content together, a common property among them must be acquired as set forth below.

From equation (1), it is known that colour is a function of coating level and imaging condition and that these two factors are independent. Considering two histogram bins having similar coating content y, which are denoted as $B_j$ and $B_k$, for image I it is calculated by:

$$P_I(B_j) = P_I(y) P_I(\phi_j), \; P_I(B_k) = P_I(y) P_I(\phi_k)$$

that $\phi_j$ and $\phi_k$ are the local average imaging conditions. For all the training images collected over a short period of time, often the only factor changing from image to image is the coating concentration distribution while overall imaging conditions (such as lighting distribution) remain the same. Therefore, $$P_{I_1}(\phi_j) = P_{I_2}(\phi_j) = \wedge = P_{I_K}(\phi_j) = s_j, \; P_{I_1}(\phi_k) = P_{I_2} = \wedge = P_{I_K}(\phi_k)$$
$$= s_k \quad (5)$$

in which $s_j$ and $s_k$ are two scalars. So, $$P(B_j) = P(y) \cdot s_j, \; P(B_k) = P(y) \cdot s_k$$

Therefore, for two histogram bins $B_j$ and $B_k$, which correspond to the same amount of local coatings concentration y, $P(B_j)$ and $P(B_k)$ will have same direction but different magnitude. The covariance between $P(B_j)$ and any other K-element vectors $z_1$, $z_2$ is computed by:

$$cov_1 = cov[P(B_j), z_1] = cov[P(y), z_1] \cdot s_j,$$

$$cov_2 = cov[P(B_j), z_2] = cov[P(y), z_2] \cdot s_j$$

The scalar can be canceled by computing the phase angle of the observed point in the space of $cov_1$ vs. $cov_2$.

$$\arg(cov_1, cov_2) = \theta(y)$$

If $\theta(y)$ and y have a one-to-one mapping relationship, $\theta$ can be segmented into several bins and each bin should represent a different coating concentration.

The choice for $z_1$ and $z_2$ is not unique. Obviously, setting $z_1$ as the average coating level is a natural choice. $z_2$ is chosen as a function of average coating level, but in such a way that $\theta(y)$ and y can achieve a one-to-one mapping relationship. $z_1$ and $z_2$ are chosen as following:

$$z_1 = \begin{bmatrix} \bar{y}_{l_1} \\ \bar{y}_{l_2} \\ M \\ \bar{y}_{l_K} \end{bmatrix}, z_2 = |z_1 - y^*| = \begin{bmatrix} |\bar{y}_{l_1} - y^*| \\ |\bar{y}_{l_2} - y^*| \\ M \\ |\bar{y}_{l_K} - y^*| \end{bmatrix}, y^* = \frac{\max(\bar{y}) + \min(\bar{y})}{2}$$

For each column of the matrix Γ, the covariance computation is applied.

$cov_1 = [cov_1(B_1) cov_1(B_2) \Lambda cov_1(B_M)]$, where $cov_1(B_i)$
    $= cov[P(B_i), z_1]$ $cov_2 = [cov_2(B_1) cov_2(B_2) \Lambda cov_2(B_M)]$, where $cov_2(B_i)$
    $= cov[P(B_i), z_2]$ An angle vector can be then computed:

$\theta = [\arg\{cov_1(B_1), cov_2(B_1)\} \Lambda \arg\{cov_1(B_M), cov_2(B_M)\}]$ The histogram bins that have similar angle values can be combined into one class. Notice that the two covariance vectors and the angle vector all have the same dimension as the histogram, therefore they can be further shown as 256×256 image as shown in the following examples.

Figure 9:
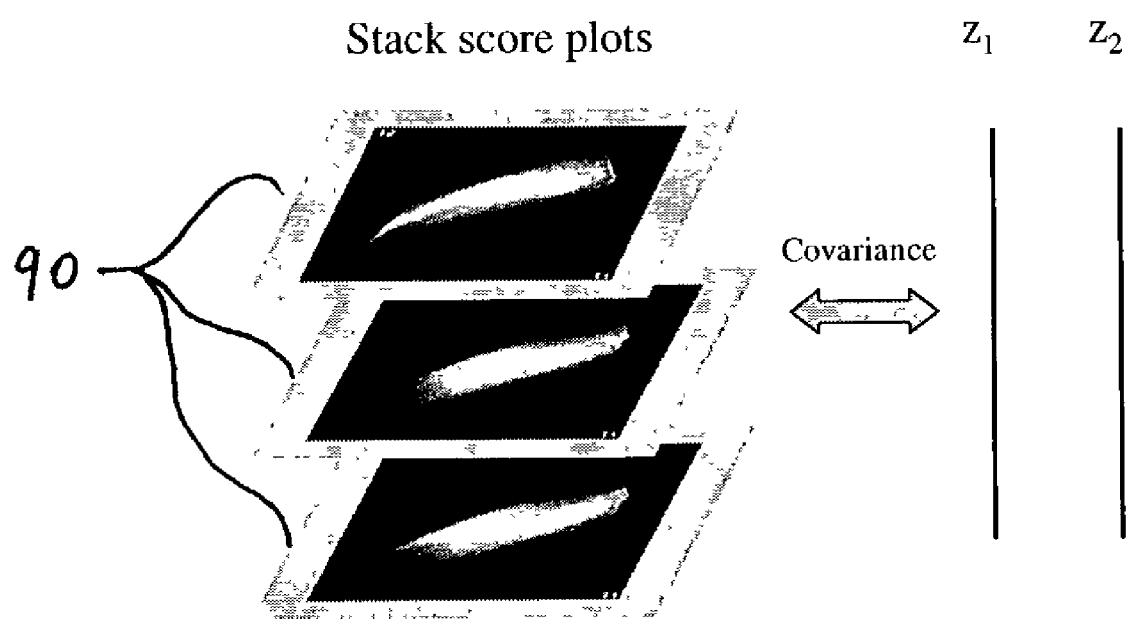
FIG. 9 represents the score plots of the imaged data stacked in order to determine the covariance according to one embodiment of the inventive method disclosed herein.
Figure 10:
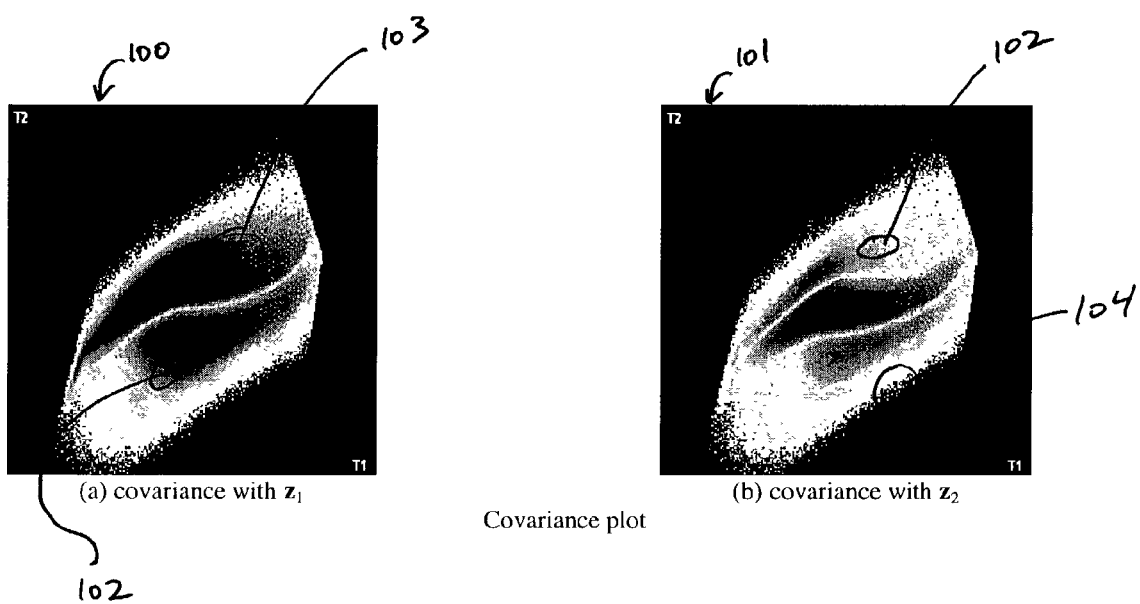
FIGS. 10-a and 10-b represent two graphical covariance plots obtained from the sample image training datasets and corresponding lab coating concentrations according to one embodiment of the inventive method disclosed herein.
Figure 11:
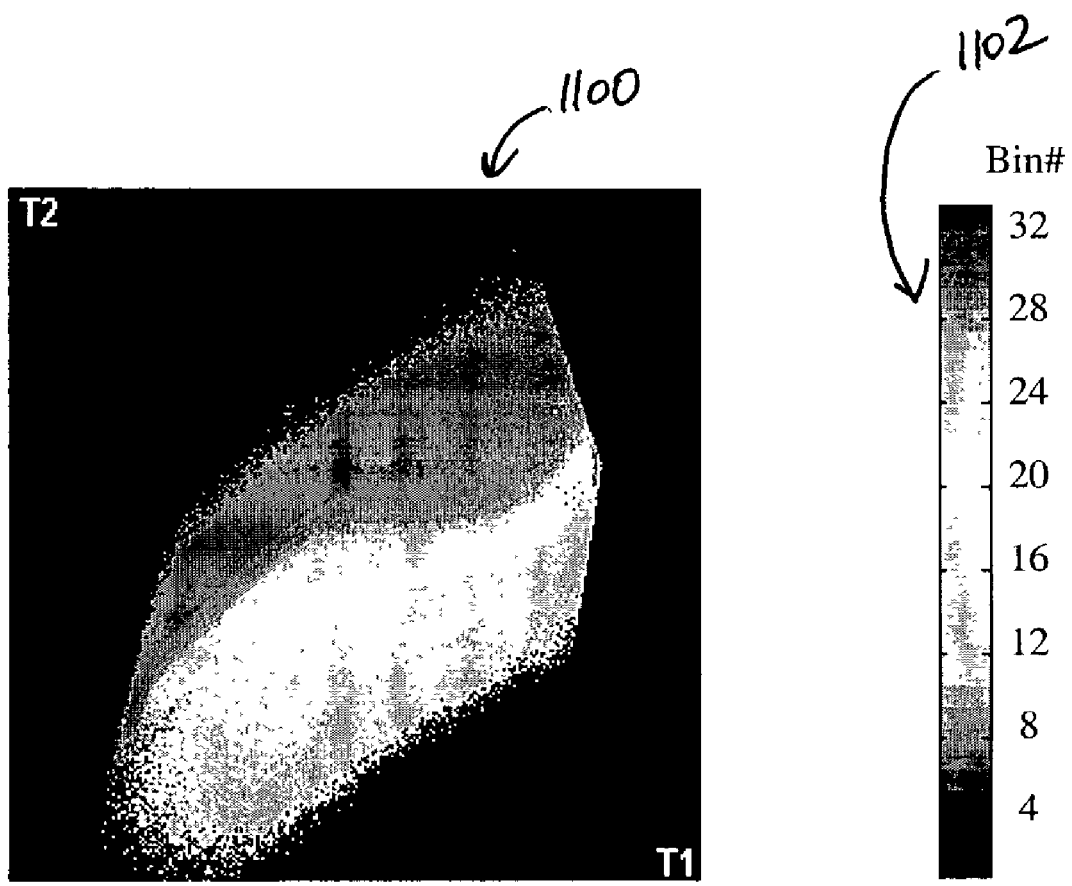
FIG. 11 is a graphical colour coded angle plot with 32 bins based on angle values which is used in the construction of a cumulative histogram based on the correlation of property segmentation in the imaged product according to one embodiment of the inventive method disclosed herein.

Method 6 is illustrated with FIGS. 9, 10 and 11. In FIG. 10, two covariance plots 100 and 101 are obtained by stacking up the 256×256 t1–t2 score plots 90 of the training set and computing the covariance of the number of pixels at each t1–t2 bin with the corresponding laboratory coating concentration as shown in FIG. 9. In the covariance plots of FIGS. 10-a and 10-b, warm colours (red) 102 indicate positive covariance values and cold colours (blue) 103 indicate negative covariance value. Darker shades 104 indicate large absolute covariance values as shown in FIG. 10-a and 10-b. From the two covariance plots (100, 101), an angle plot can be calculated as explained above.

Figure 12:
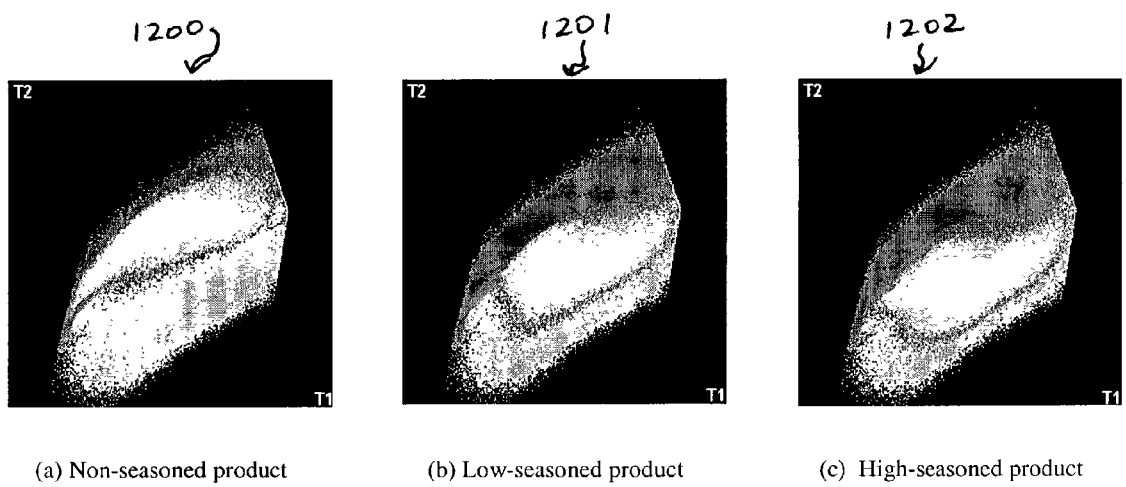
FIGS. 12-a, 12-b and 12-c depict image score plots on top of a colour coded angle plot divided into 32 bins and for non-seasoned, low-seasoned and high-seasoned products, respectively, according to one embodiment of the inventive method disclosed herein.
Figure 13:
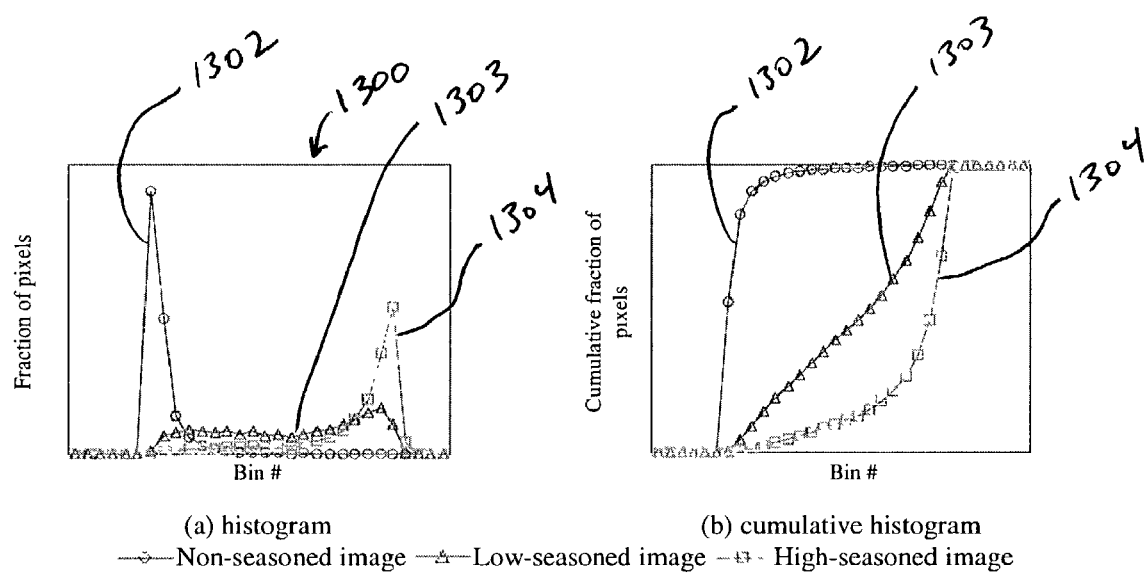
FIGS. 13-a and 13-b depict the resulting histogram and cumulative histogram, respectively, for the three product sample images score plots shown in FIGS. 12-a, 12-b and 12-c according to one embodiment of the inventive method disclosed herein.

FIG. 11 depicts the colour-coded angle plot 1100 divided into 32 bins 1102 based on angle values. The score plot for any image can be superimposed on top of this plot and the number of pixels falling into each of these 32 angle bins recorded to form a one-dimensional histogram, as illustrated in FIGS. 12-a, 12-b and 12-c for non-seasoned product 1200, low-seasoned product 1201 and high-seasoned product 1202, respectively. Resulting histogram and cumulative histogram for three sample images 1200, 1201, 1202 are shown in FIGS. 13-a and 13-b. Non-seasoned image 1302, low-seasoned image 1303, and high-seasoned image 1304, are shown plotted as the bin number versus fraction of pixels in FIG. 13-a and bin number versus cumulative fraction of pixels in FIG. 13-b, respectively. It is noted that when building the regression model, only the cumulative histogram is used as the feature vector.

Foreground/Background Segmentation

Figure 15:
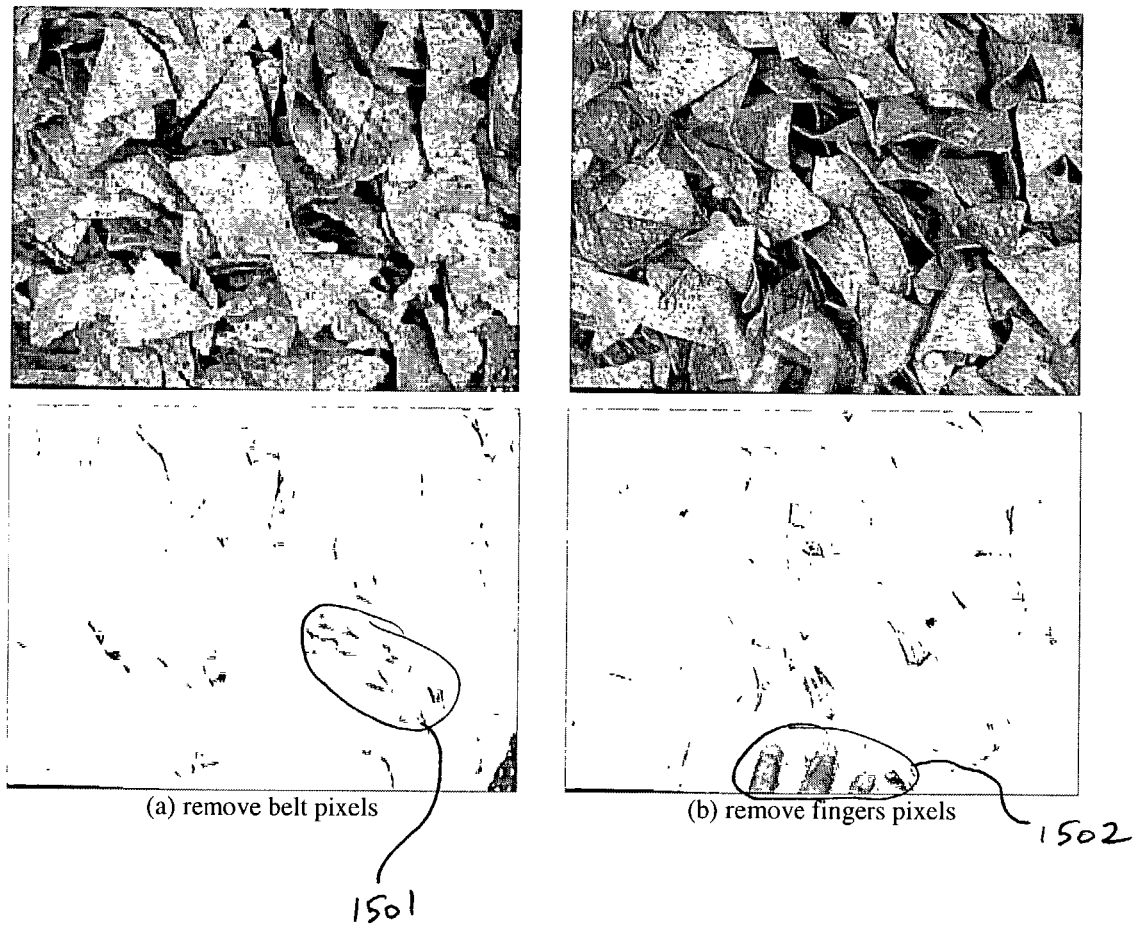
FIGS. 15-a and 15-b depict the background and foreign object pixels representing the conveyor belt and operator fingers which are removed during the segmentation step according to one embodiment of the inventive method disclosed herein.

One important step that must be performed before feature extraction is determined. This step of segmentation is the removal of pixels associated with background in the imaged product 1500. In the foodstuff manufacturing environment, background arises from exposed areas of the table or pan on which the product is placed (off-line) or from exposed conveyor belt (on-line). FIG. 15-a depicts dark pixels 1501 that that represent the conveyor belt on which products 1500 are transported, while FIG. 15-b shows a technicians fingers 1502 resting on the conveyor belt along with product.

One approach based on spectral feature difference between the food product and the background uses product C above as the example. Since visual interpretation is not straightforward in three-dimensional colour space, a PCA is first performed to reduce the dimension. In this approach, PCA (without mean-center) loading vectors are computed using all the training images and a pure belt image or control process. As in traditional MIA techniques (Geladi et. al.), masks are chosen in the t1–t2 score space to separate different features. However, masks can not be chosen by a trial-and-error process as has been traditionally performed in MIA, because: 1) in some images, belt pixels can easily be overlooked because of dark lighting conditions and misclassified as snack product pixels; 2) there is not only one image to be studied but a set of images and manual trial-and-error approaches on each image is too time consuming. To solve these two problems, a new procedure for segmentation of the undesired image background is presented below.

Figure 17:
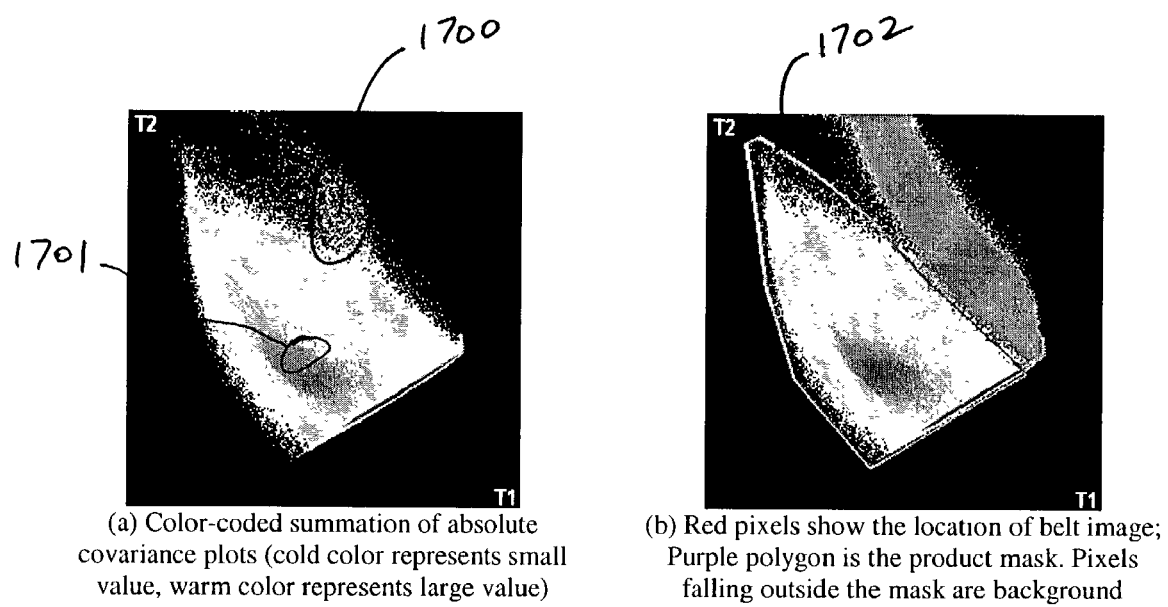
FIGS. 17-a and 17-b is a graphical image depicting the calculated product mask which removes undesired pixels containing background and foreign objects according to one embodiment of the inventive method disclosed herein.

After a t1–t2 plane is obtained by PCA, t1–t2 score plots are stacked together for all training images; then two covariance plots $COV_3$ and $COV_4$ (with $z_1$ and $z_2$) can be computed as shown in method 6 discussed above. Since the background is independent of coatings concentration, histogram counts of a background colour should have low values in both covariance plots. Therefore, the absolute values of these two covariance plots are added together which, in turn, locates the pixels that have low total covariance values. Such a summation of the covariance plots is shown in FIG. 17-a (cold colours 1700 denote small covariance values and warm colours 1701 denote large covariance values). Moreover, the projection of the belt image into this (t1–t2) space can also help to locate belt pixels (shown as medium gray pixels in FIG. 17-b). A product mask 1702 (the area within outlined polygon in FIG. 17-b) can be then created based on the covariance information and location of belt image. For the new images, score pixels falling outside the product mask 1702 are considered as belonging to undesired background. The advantages of this method are manifested when calculating covariance plots that were considered in collecting information from all the training images. As such, this approach is not influenced by dark lighting condition that could influence human visual judgment. It is interesting to note that this technique is able to remove not only the background expected (e.g. Belt 1501 in FIG. 15-a) but also the background unexpected (e.g. Fingers 1502 in FIG. 15-b).

Prediction of Coating Concentration

Once feature variables have been obtained by any of the six methods, one can build inferential models by regressing these feature variables with the observed laboratory coatings concentration for the training set. In the preferred embodiment of the invention, PLS regression is desired to perform the regression analysis. In all PLS models, the feature variables are mean-centered and scaled to unit-variance. Transformations are used for the overall features (methods 1 and 2) to correct the nonlinearity. For the average colour features, a logarithmic transformation was used:

$x_i' = \log(x_i), I = R, G, B$

Since the loading values have the range between 0 and 1, a logistic transformation is used for the $1^{st}$ loading vector features (method 2):

$$x'_l = \log\left(\frac{x_l}{1-x_l}\right), l = R, G, B$$

Figure 14:
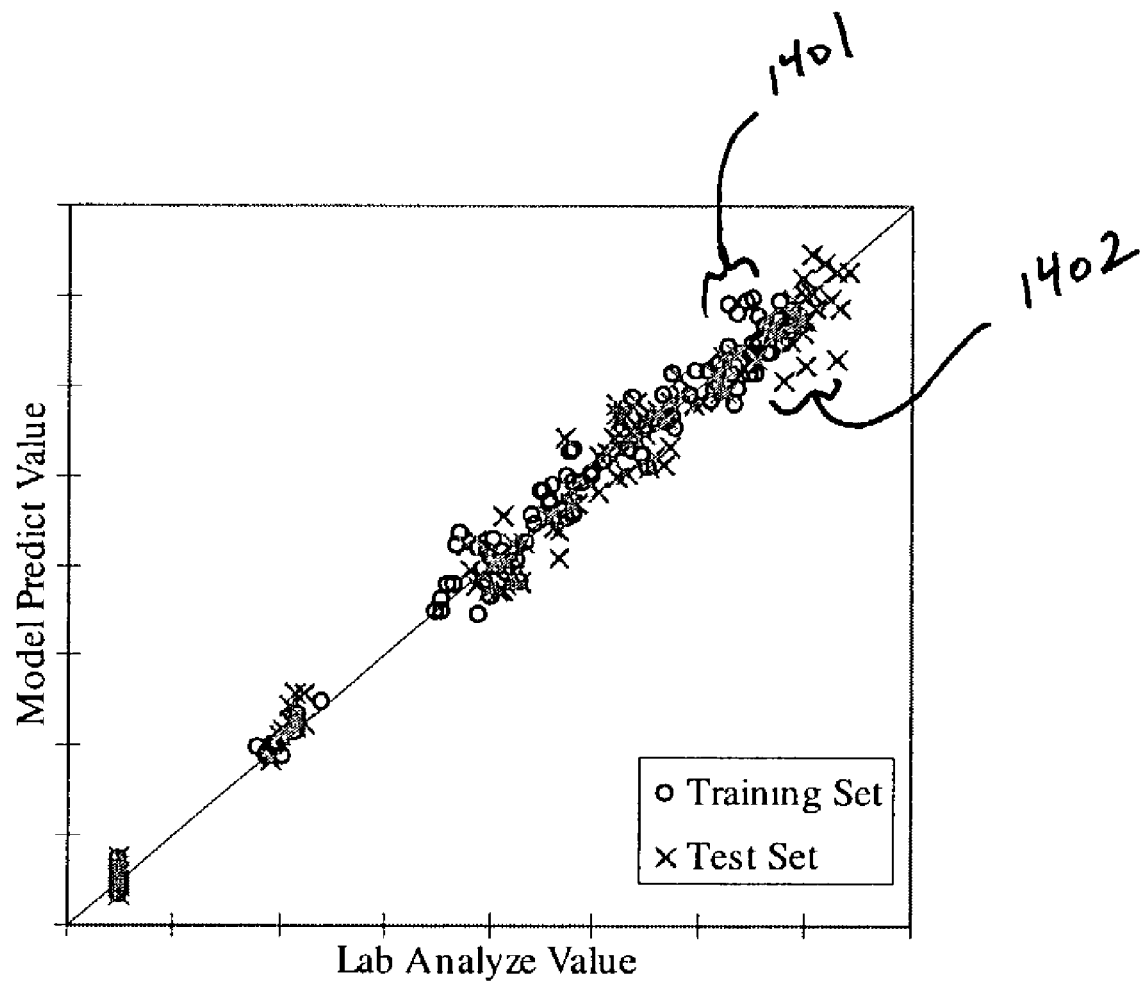
FIG. 14 is a graphical representation of the model predicted coating concentration versus laboratory analysis of the coating concentration on the food product training dataset and test dataset sampled and modeled according to one embodiment of the inventive method disclosed herein.

The performance of the PLS models are depicted in FIG. 14 and Table 2.

FIG. 14 plots the predicted average coating level versus laboratory analysis data for example product C using method 6 with training dataset data points 1401 and test dataset data points 1402. Similar plots can be obtained by using other methods or for other products. One can see that both the fit of the training dataset and the prediction of the test dataset are excellent.

Test results using all 6 feature extraction methods for Products A, B and C for both the training and testing image sets are shown in Tables 2-a, b, c below. In these tables, the original number of feature variables, the number of components used in PLS regression, the sum of square prediction error (SSE) and R-square statistic (the ratio of the regression sum of squares to the total sum of squares) are given. From the results, it is clear that each method works well and all have almost the same performance in all the cases. Moreover, it seems that the simple overall feature variable methods (methods 1 and 2) perform as well as the more complex distribution feature (methods 3, 4, 5, and 6) models.

TABLE 2

Model Prediction Results

| | | Feature variable # | Latent variable # | Variance Analysis $SS_E$ | $R^2 = 1 - SS_E/SS_T$ |
|---|---|---|---|---|---|
| (a) Product A; $SS_T$ = 377.44 (Training set); $SS_T$ 385.13 (Test set) | | | | | |
| Model 1 | Training set | 3 | 2 | 1.13 | 0.997 |
| | Test set | | | 1.60 | 0.996 |
| Model 2 | Training set | 3 | 2 | 2.25 | 0.994 |
| | Test set | | | 1.59 | 0.996 |
| Model 3 | Training set | 424 | 3 | 1.59 | 0.996 |
| | Test set | | | 3.60 | 0.991 |
| Model 4 | Training set | 32 | 3 | 0.95 | 0.997 |
| | Test set | | | 1.83 | 0.995 |
| Model 5 | Training set | 25 | 3 | 1.34 | 0.996 |
| | Test set | | | 1.18 | 0.997 |
| Model 6 | Training set | 19 | 2 | 0.74 | 0.998 |
| | Test set | | | 0.89 | 0.998 |
| (b) Product B; $SS_T$ = 869.83 (Training set); $SS_T$ = 845.41 (Test set) | | | | | |
| Model 1 | Training set | 3 | 2 | 7.96 | 0.991 |
| | Test set | | | 8.64 | 0.990 |
| Model 2 | Training set | 3 | 2 | 4.58 | 0.995 |
| | Test set | | | 5.42 | 0.994 |
| Model 3 | Training set | 329 | 5 | 2.21 | 0.997 |
| | Test set | | | 5.13 | 0.994 |
| Model 4 | Training set | 32 | 3 | 3.58 | 0.996 |
| | Test set | | | 7.14 | 0.992 |
| Model 5 | Training set | 24 | 2 | 5.11 | 0.994 |
| | Test set | | | 8.72 | 0.990 |
| Model 6 | Training set | 18 | 2 | 5.82 | 0.993 |
| | Test set | | | 5.83 | 0.993 |
| (c) Product C; $SS_T$ = 817.19 (Training set); $SS_T$ = 751.63 (Test set) | | | | | |
| Model 1 | Training set | 3 | 3 | 19.81 | 0.976 |
| | Test set | | | 13.12 | 0.983 |
| Model 2 | Training set | 3 | 2 | 20.09 | 0.975 |
| | Test set | | | 14.50 | 0.981 |
| Model 3 | Training set | 427 | 3 | 12.67 | 0.984 |
| | Test set | | | 18.56 | 0.975 |
| Model 4 | Training set | 32 | 3 | 17.75 | 0.978 |
| | Test set | | | 17.49 | 0.977 |
| Model 5 | Training set | 15 | 3 | 16.29 | 0.980 |
| | Test set | | | 13.66 | 0.982 |
| Model 6 | Training set | 19 | 2 | 20.56 | 0.975 |
| | Test set | | | 13.87 | 0.982 |

Figure 18:
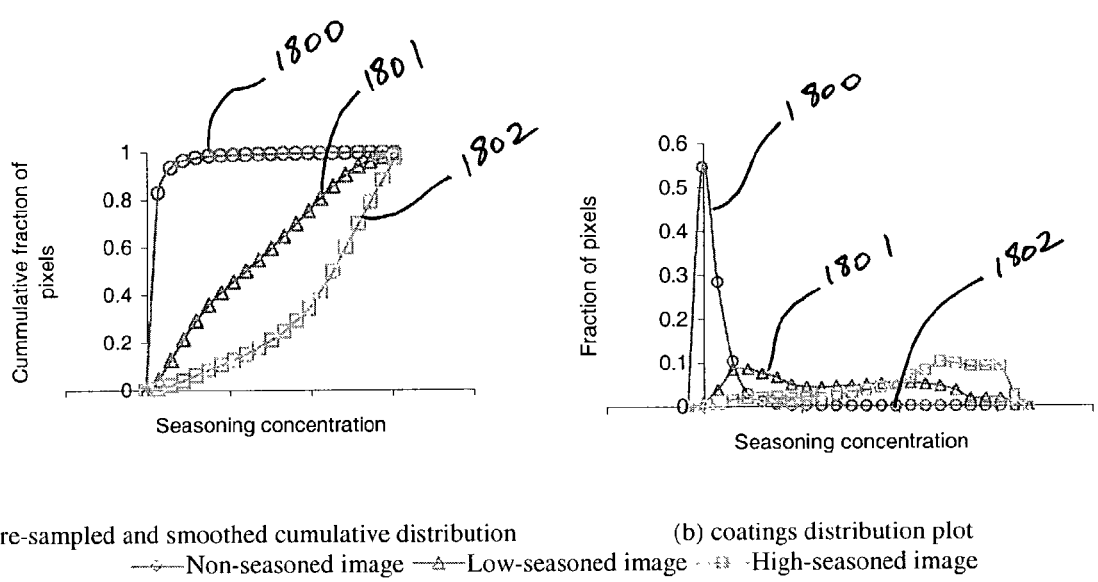
FIGS. 18-a and 18-b are graphical representations of the re-sampled and smoothed cumulative seasoning concentrations, respectively, for non-seasoned, low-seasoned, and high-seasoned products obtained by utilization of method 6 according to one embodiment of the inventive method disclosed herein.

An estimation of the coating concentration can now be obtained directly, in this example by using method 6, by combining the cumulative angle histogram shown in FIG. 13-b and the estimated coating concentration for each bin shown in FIGS. 16-b, 16-c and 16-d. The resulting 32 bin cumulative coating distribution is then equally resampled and smoothed by a central moving-average smoother as shown in FIG. 18-a for the three sample images of product C, non-seasoned product 1800, low-seasoned product 1801 and high-seasoned product 1803 as referenced in Table 1. From these operations, the coating distribution is obtained as shown in FIG. 18-b.

Figure 19:
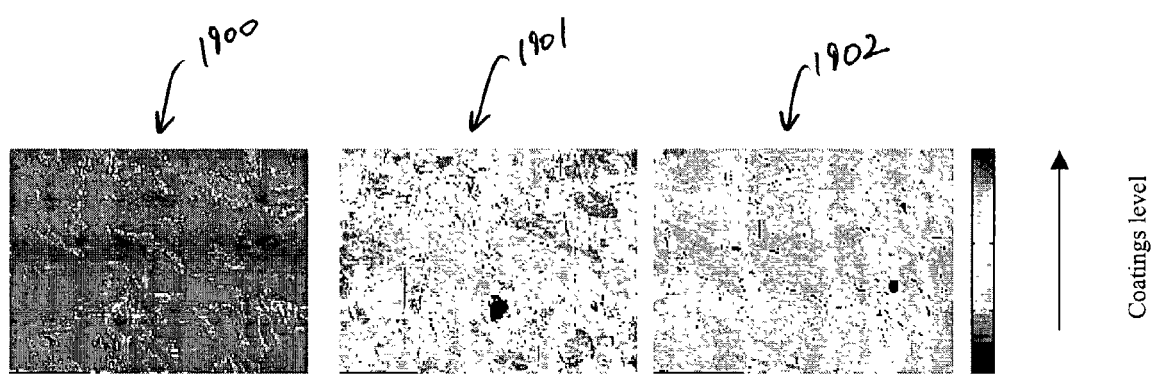
FIG. 19 is a colour-coded graphic display of the showing the calculated seasoning concentration on food products according to one embodiment of the inventive method disclosed herein.
Figure 20:
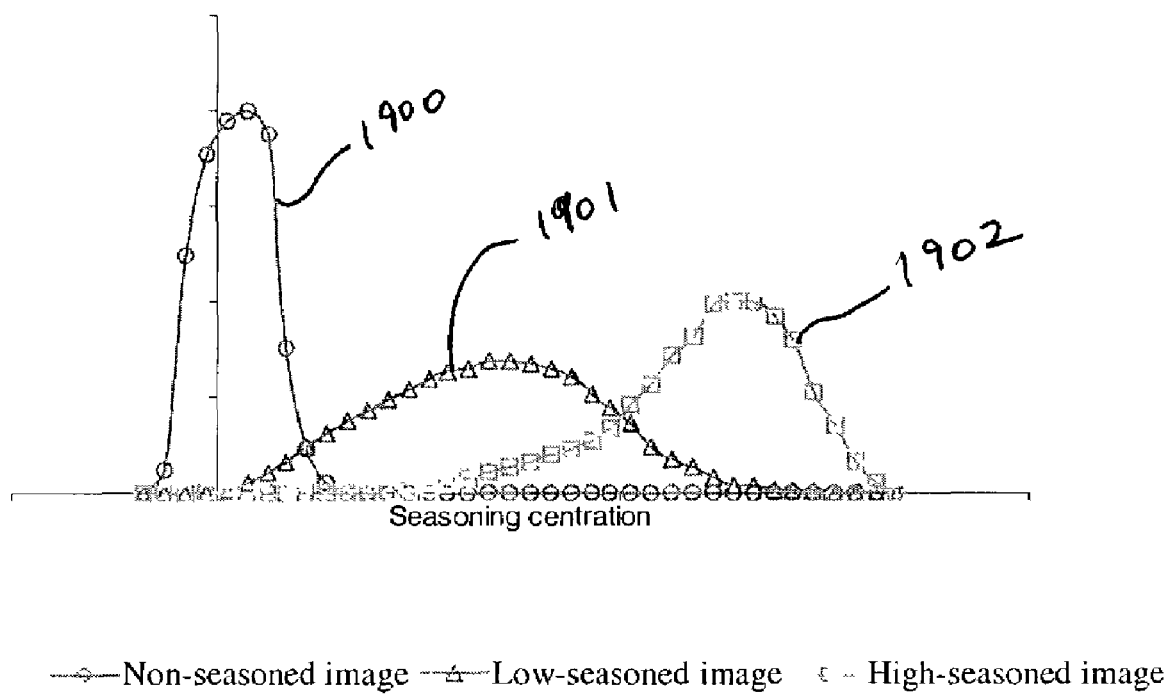
FIG. 20 is a graphical representation of the resulting coating distribution for the 3 sample images of product C using the small window strategy according to one embodiment of the inventive method disclosed herein.

Since method 6 can predict the coating concentration for each pixel, a colour-coded image can be generated on the coating concentration of each pixel for graphical display. FIG. 19 shows the colour-coded sample images for the product C samples. Image 1900 represent under seasoned products, image 1901 represents moderately seasoned products and image 1902 represents highly seasoned products. These graphical display images are excellent for a quality control observer to visually monitor and control the manufacturing processes. FIG. 20 is a graph representation depicting the resulting seasoning concentrations for imaged product in FIG. 19 for non-seasoned product 1900, low-seasoned product 1901 and high seasoned product 1902.

Small Window Strategy

An alternative method of estimating the coating coverage distribution can be obtained by using larger areas of the imaged product, which is referred to as "small window" strategy. In this regime, each image is divided into many small windows and the coating concentration can be obtained by calculating average coating concentration for each window. Method 6 is preferred for small window prediction as it is the only method disclosed herein which is not image size sensitive. In small window strategy, it is important to choose a proper window size. If this window size is too large, the spatial distribution information may be lost. On the other hand, if the window size is too small, the computation time may increase and the variance of the estimates will increase. An example of the small window procedure is discussed below.

Figure 21:
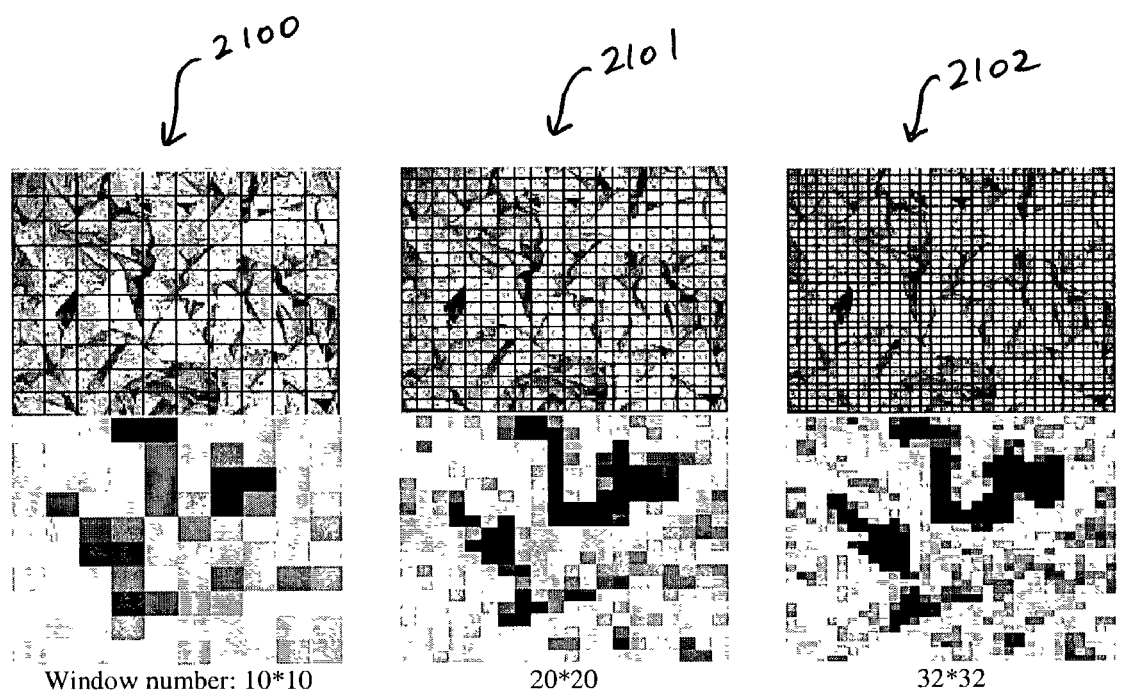
FIG. 21 represents the different divisions of product images for a 10×10, 20×20 and 32×32 small window size calculation according to one embodiment of the inventive method disclosed herein.
Figure 22:
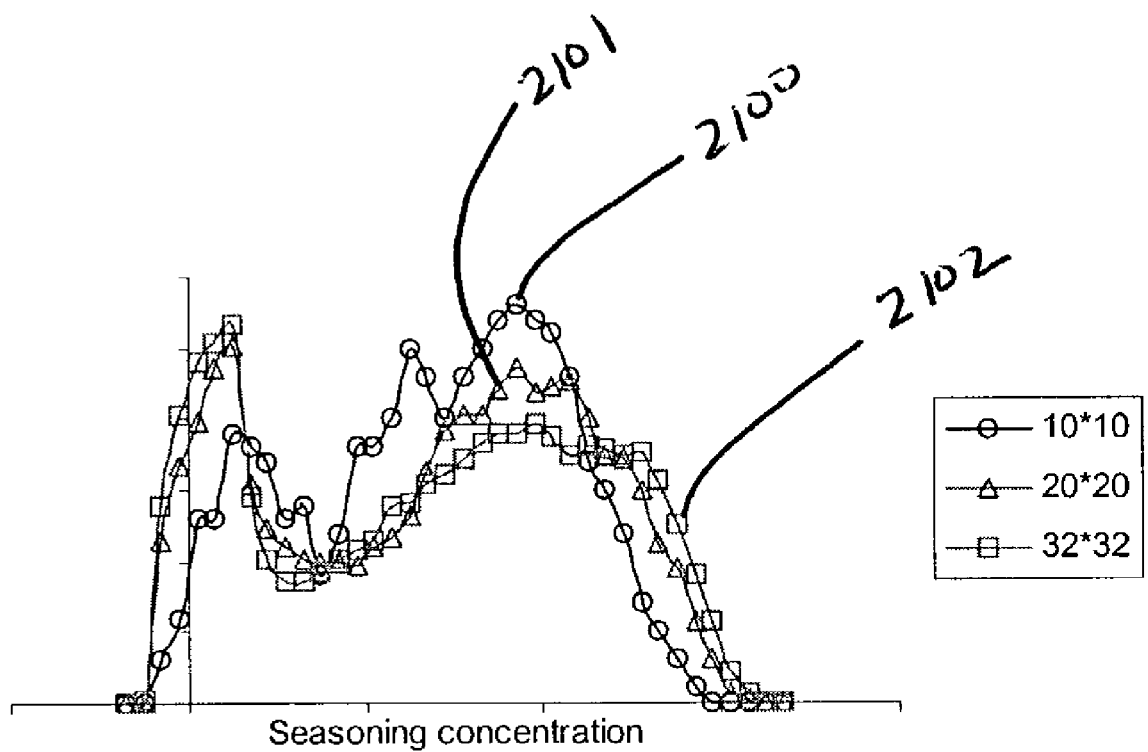
FIG. 22 is a graphical representation of the coating distribution obtained by using the 10×10, 20×20 and 32×32 small window sizes according to one embodiment of the inventive method disclosed herein.
Figure 23:
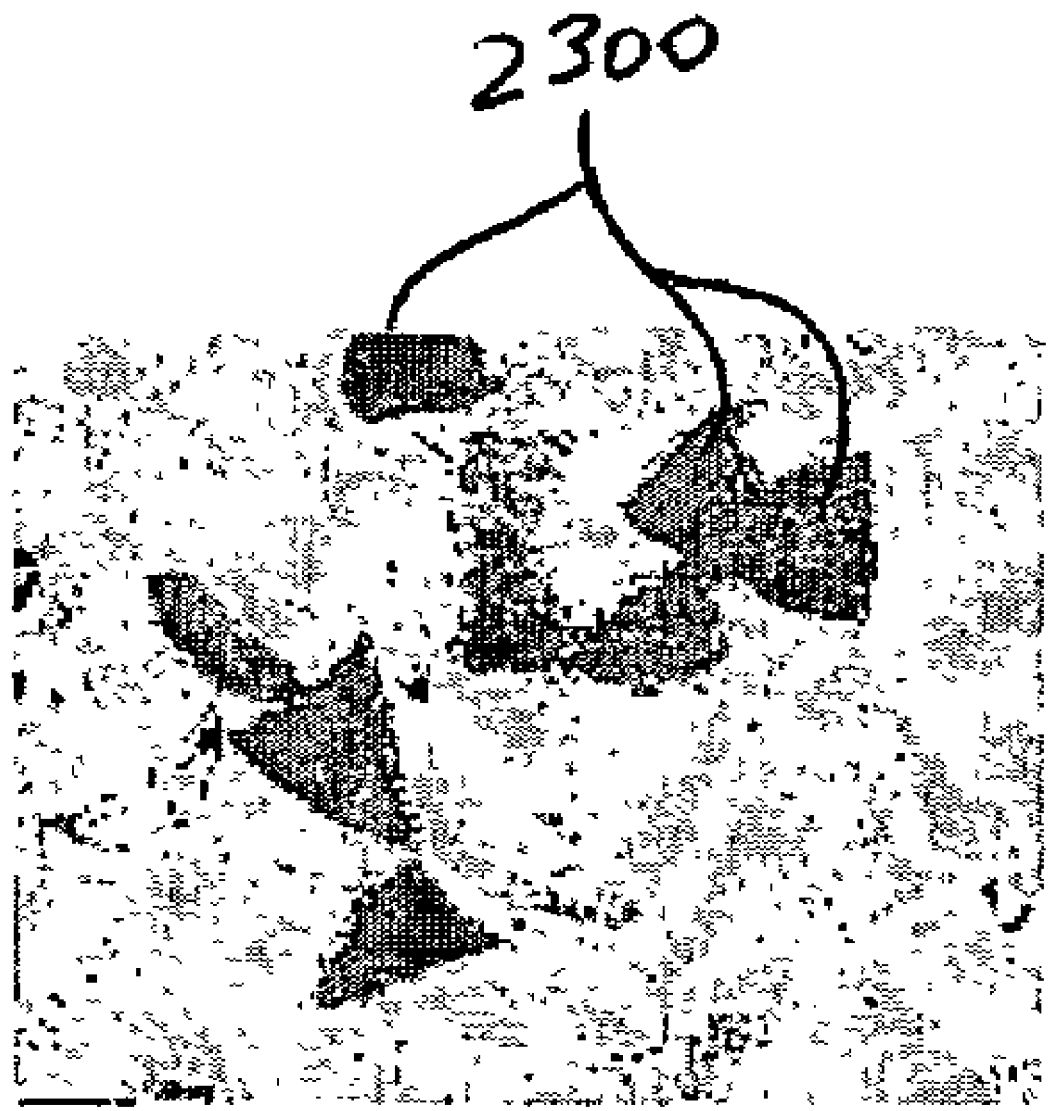
FIG. 23 is a colour-coded product image demonstrating the coated and non-coated seasoning portions on the food product according to one embodiment of the inventive method disclosed herein.

An image with mixed products (non-seasoned product and high-seasoned product) is used to demonstrate the effect of different image window sizes. The product image in FIG. 21 is divided into 10×10, 20×20 and 32×32 windows 2100, 2101, 2102, respectively. The estimated local coating concentration is shown by colour-coded images (same colour map is used as in FIG. 19). The resulting coating distribution estimates are shown in FIG. 22. When using 10×10 windows 2100, the two maxima are not as clear as the maxima found in using 20×20 windows 2101 and 32×32 windows 2102. The difference between the 20×20 and 32×32 samples 2101, 2102 is very small, since a 20×20 window 2101 size can capture an adequate amount of the coating distribution features, it can be chosen as minimal practical window size for the small window application. FIG. 23 is a pixel by pixel representation of a colour-coded image obtained by the utilization of small windows strategy. As compared to the images in FIG. 19, it can be readily appreciated that the image in FIG. 23 generated by using small window strategy more clearly identifies the location and shape of non-coated product 2300.

Figure 24:
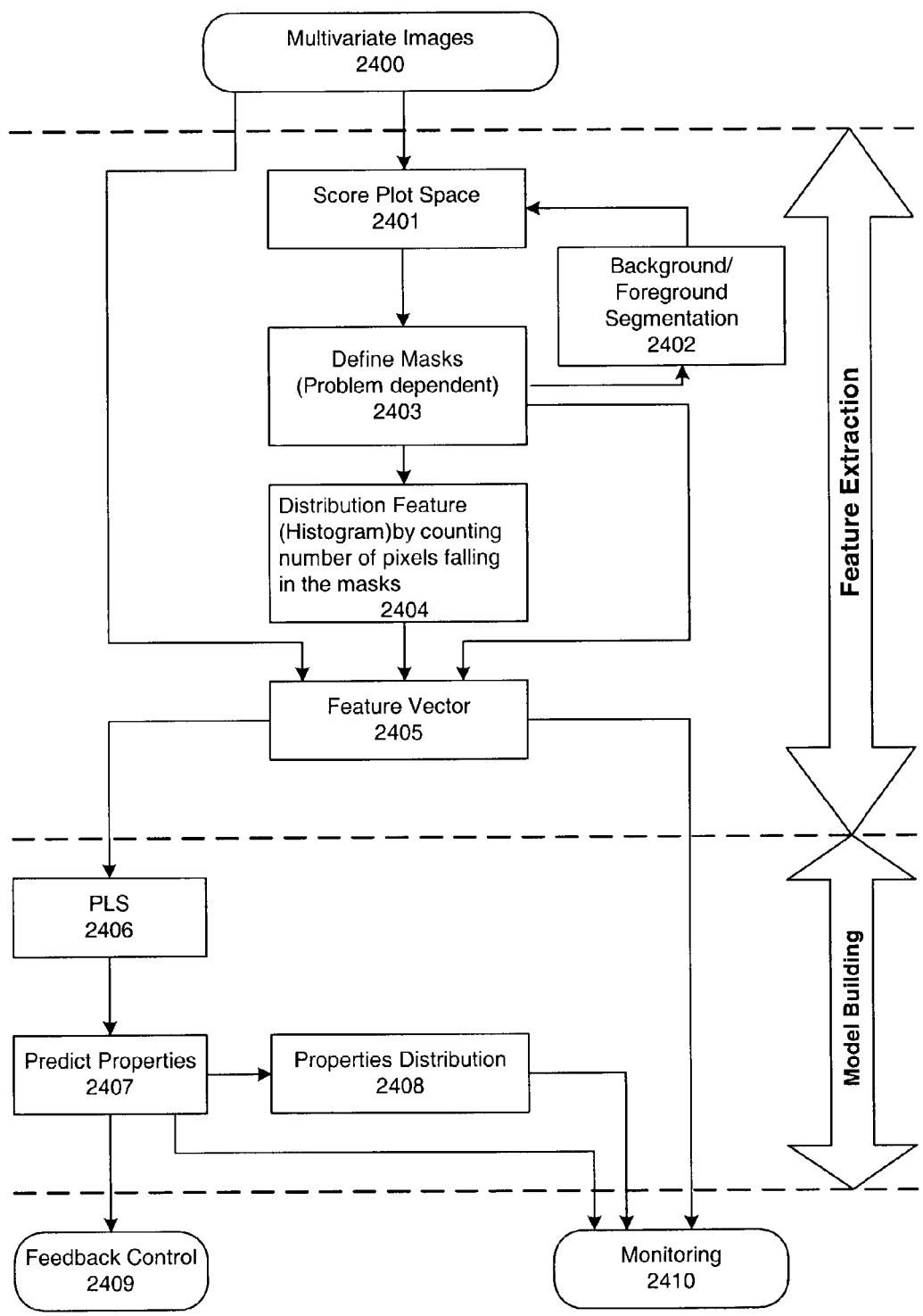
FIG. 24 is a flow chart depiction of the implementation of the product feature determination method disclosed herein.

Turning now to FIG. 24, a flow chart depicting one embodiment of the method disclosed herein is shown as utilized in the quality monitoring and control of foodstuff manufacturing. The method may be initially divided into two phases for identification purposes: (1) the feature extraction phase and (2) the modeling building phase. In the preferred embodiment, the feature extraction phase occurs initially with the acquisition of multivariate images acquired by digital imaging equipment placed in an appropriate position in the on-line manufacturing environment (Step 2400). Next, a score plot space is acquired and an appropriate mask definition is developed (Step 2401) during background/foreground segmentation (Step 2402). After the appropriate mask is calculated (Step 2403), a histogram is created for the desired product feature (e.g. seasoning concentration) is created by implementing the feature extraction by method 6 discussed herein (Step 2404) and the feature vector is calculated (Step 2405).

The model building phase then begins with the implementation of a PLS regression applied to the calculated feature variables, that are described by the feature vector, and the quality or control variables as defined by the training set test samples analyzed in the laboratory (Step 2406). The extracted feature, in this example the seasoning concentration on the foodstuff, is then predicted (Step 2407) and a property distribution may be constructed showing the predicted seasoning distribution on the on-line sample (Step 2408) or presenting an estimate of the spatial variance of the coating concentration. The calculated coating concentration is then supplied to a feedback control device (Step 2409) and/or a monitoring array (Step 2410) which control the operation of the on-line environment and can be instructed to take appropriate action in the event a process or control function is required. In an alternative embodiment, the distribution step (Step 116) may be omitted to streamline the submission of acceptable data to monitor and control operations.

Figure 25:
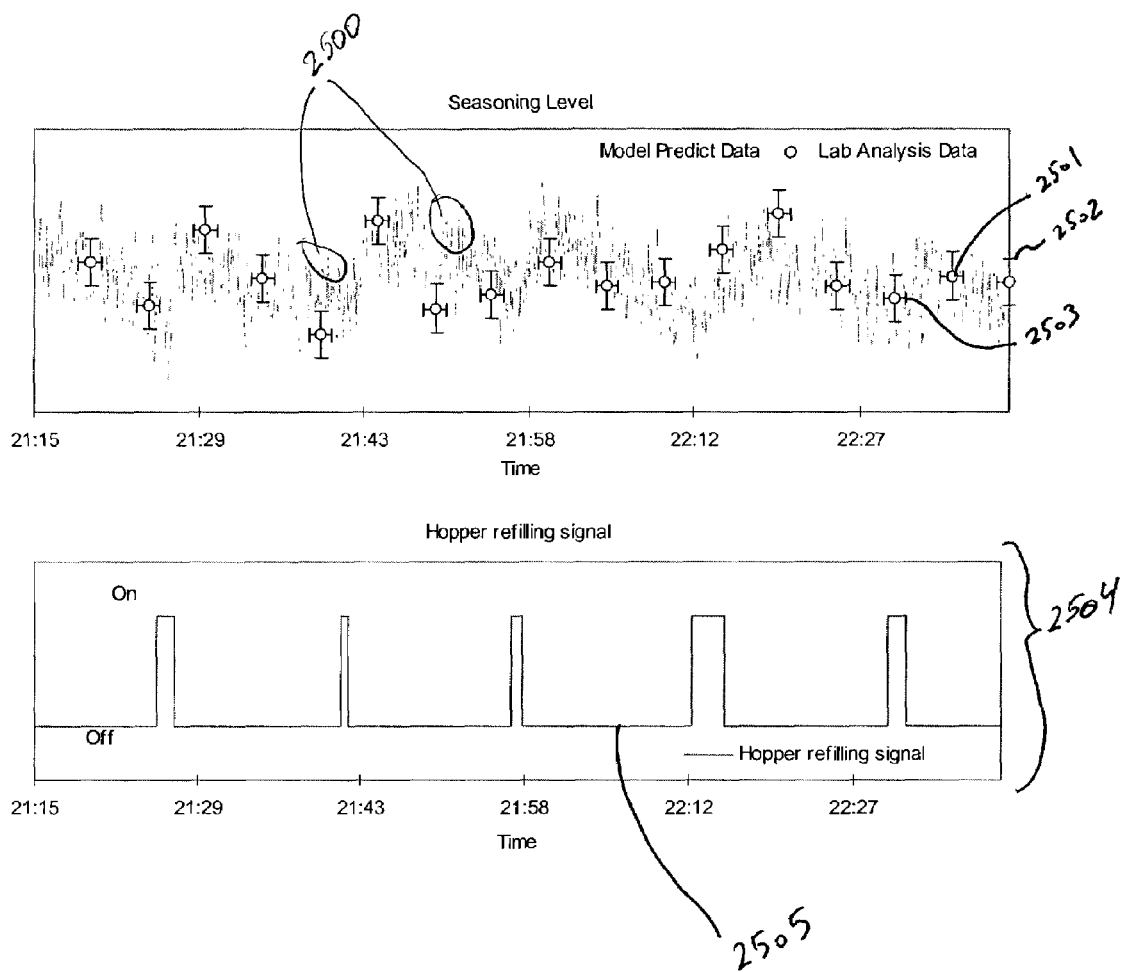
FIG. 25 is a graphical depiction of seasoning concentration level versus time compared with the detection of the seasoning hopper refill signal according to one embodiment of the inventive method disclosed herein.

Sample results which were observed in utilizing the methods discussed in the example above are set forth in the following discussion and referenced figures for snack food coating concentration and coverage in an on-line environment. FIG. 25 depicts initial data collected from the imaging system. The raw coatings predictions are shown by the light gray lines 2500. In this example, frequent grab samples were taken every 5 minutes from the conveyor and analyzed thereafter in the laboratory. The analytical results of the grab samples are shown as black circles 2501 in FIG. 25. For each laboratory measurement, a X-error bar 2502 and an Y-error bar 2503 are also depicted. The Y-error bar 2503 indicates the approximate laboratory measurement error; the value is ±0.5 in FIG. 25. The X-error bar 2502 indicates the possible sample time mismatch between taking the digital images of product moving on the conveyor line and manually grabbing the product samples for laboratory analysis. In this example, the error is estimated as ±1 minute.

One can see that the predicted coatings concentrations from the images match up well with the laboratory analysis. However, the image predictions reveal a clear saw-tooth behavior in the concentration that is not evident only from the lab data even during this fast sampling program. This unexpected result was explained by the coatings hopper refilling operations in the process. The lower plot 2504 in FIG. 25 depicts the signal 2505 of the hopper motor of the tumbler refilling system over a specified time interval. As the level of the coatings powder in the feed tumbler falls to a certain level, the motor is activated to refill the tumbler. The level of food coating inside the tumbler then increases rapidly. Clearly, FIG. 25 reveals that the discharge rate of food coating from the hopper to the coating tumbler is a strong function of the coatings level in the hopper.

Open Loop Results for Product A

In FIGS. 26-*a* and 26-*b*, the open-loop response of food product coating level caused by changing the coating level bias (manipulated variable) is shown. The prediction 2600 and laboratory analysis 2601 coating levels are shown in the upper plot FIG. 26-*a* and, in the lower plot FIG. 26-*b*, the coating level bias signal 2602 is shown. Again, it is observed that the predictions from the image analysis and the laboratory measurements are consistent. The predicted data shows a clear quick response to each coating level bias change.

On-Line Monitoring Sample Results for Products A and B

Figure 27:
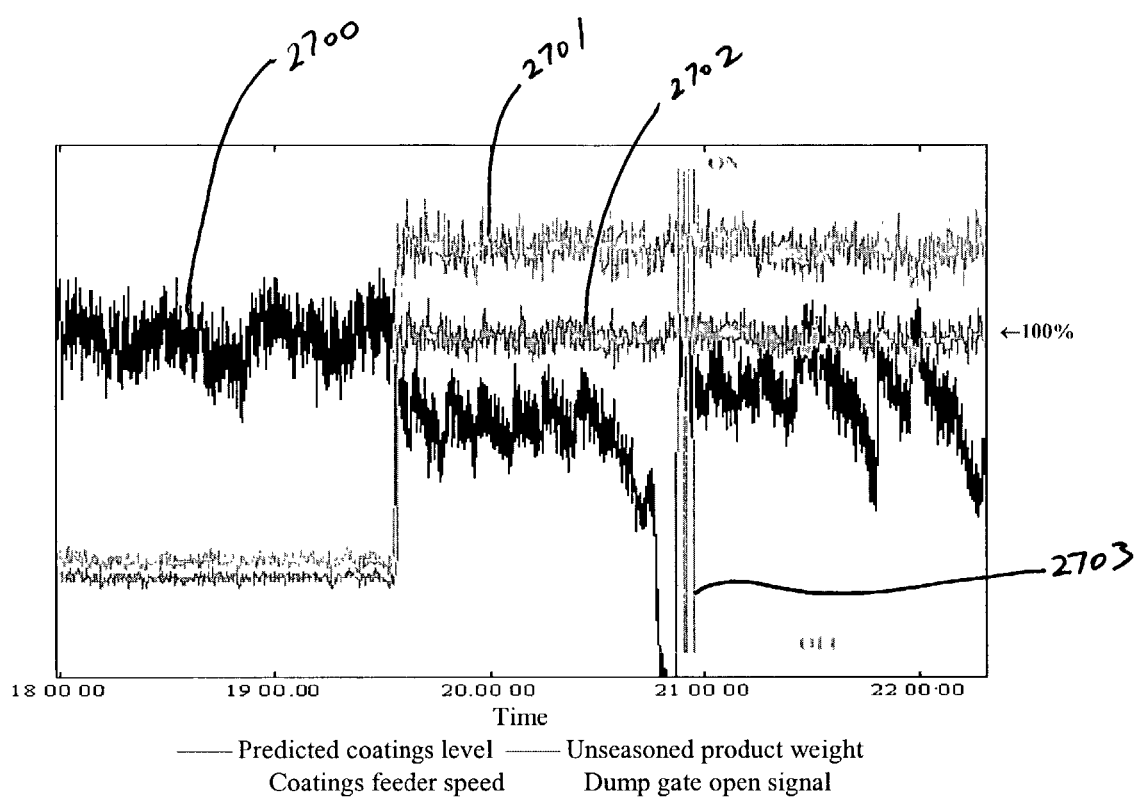
FIG. 27 represents a graphical depiction of the predicted seasoning level, observed unseasoned product weight, the seasoning feeder speed and signal of the dump gate to divert inferior product for product A according to one embodiment of the inventive method disclosed herein.

FIG. 27 depicts a single, four hour on-line monitoring period for product A. Line 2700 indicates the predicted coatings level, line 2701 represents the unseasoned product weight, line 2702 indicates the coating feeder speed and line 2703 indicates the signal of the coating dump gate. During the time period, at about time 19:35, the feed rate of the non-seasoned product to the tumbler suddenly increased and as the result of ratio control, the coating feeder speed also increased. However, the coating feeder speed was limited by its maximum capacity and could not feed coatings fast enough to keep the desired ratio to the unseasoned product. Therefore, the coating level on product was observed to decrease from the desired value. Another concern was identified at time period starting at about time 20:40 where the coating level suddenly started to continuously decrease. This occurred because the coating hopper was not set to automatic refill mode and was therefore being depleted of coating. The result was that eventually no coating was being fed to the tumbler and the product dump gate had to open to remove the unseasoned products from the belt. It should be pointed out that by looking only at process data (non-seasoned product weight and coatings feeder speed) this fault was not detectable.

Figure 28:
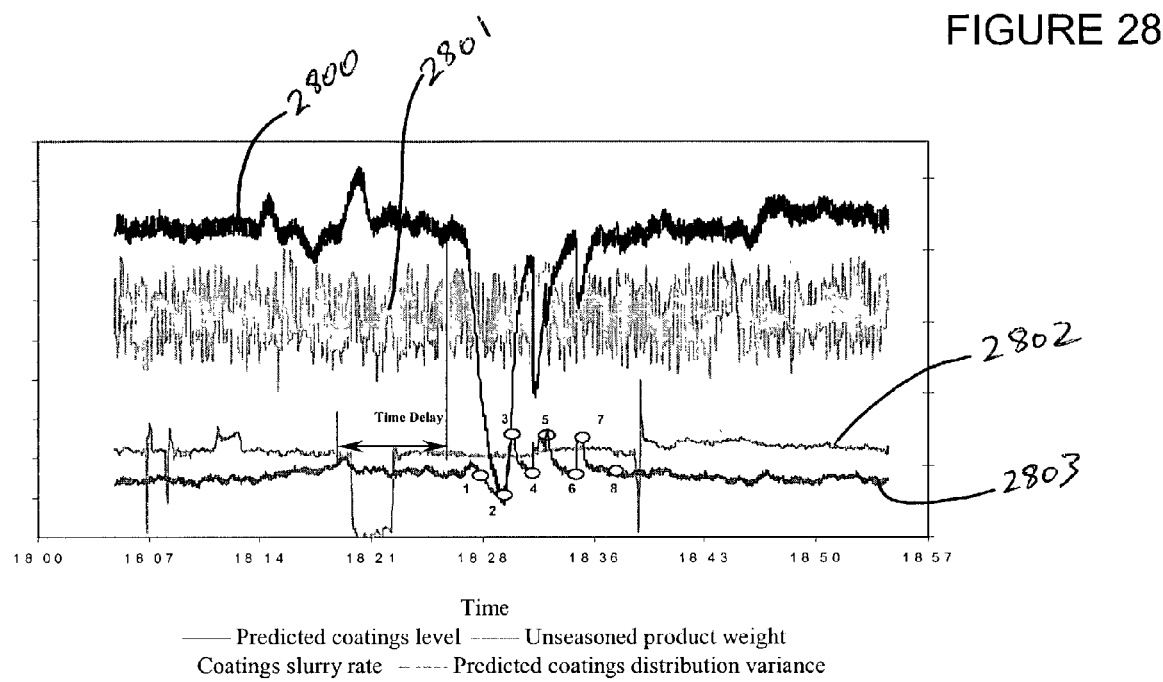
FIG. 28 is a graphical depiction of the predicted seasoning level, observed unseasoned product weight, the seasoning slurry feed rate, and the predicted seasoning distribution variance for product B according to one embodiment of the inventive method disclosed herein.

FIG. 28 shows one example of on-line monitoring for product B. In FIG. 28, line 2800 represents the predicted coating level, line 2801 represents the unseasoned product weight, line 2802 represents the coatings slurry feed rate and line 2803 in the lower portion of the graph represents the predicted coatings distribution variance. The variance of the coatings distribution was calculated from the histogram of the coatings concentrations obtained by applying the small window strategy outlined previously herein.

During this approximate 1 hour period of time, there was no large variation in the feed-rate of unseasoned product. However, it was observed that between time 18:19 and 18:23, the coating slurry feed-rate suddenly dropped to zero. The effect of this disturbance on the seasoned product appeared after about 8 minutes of time delay. At roughly 18:27, both the predicted coatings level and the coatings distribution variance began to show large variation.

Figure 29:
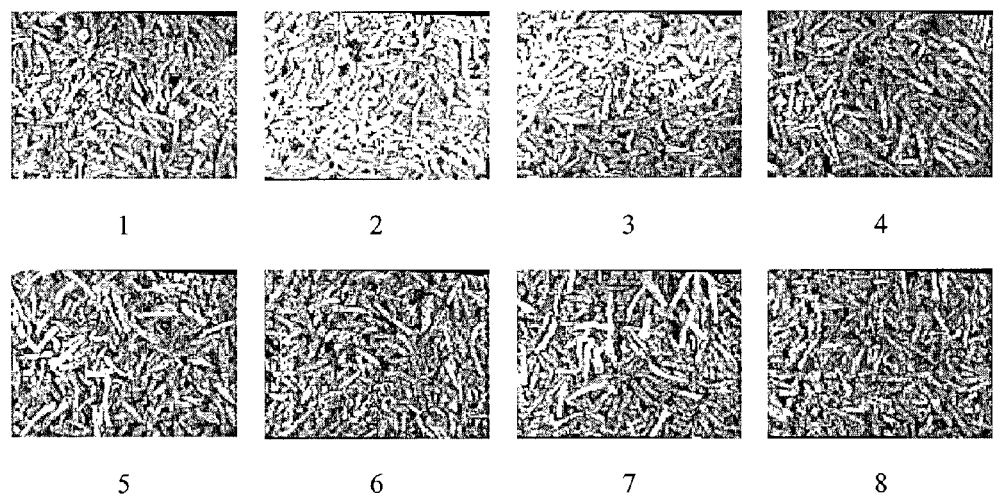
FIG. 29 represents images of product with various seasoning coatings which correspond with the numerals placed on FIG. 28 according to one embodiment of the inventive method disclosed herein.
Figure 30:
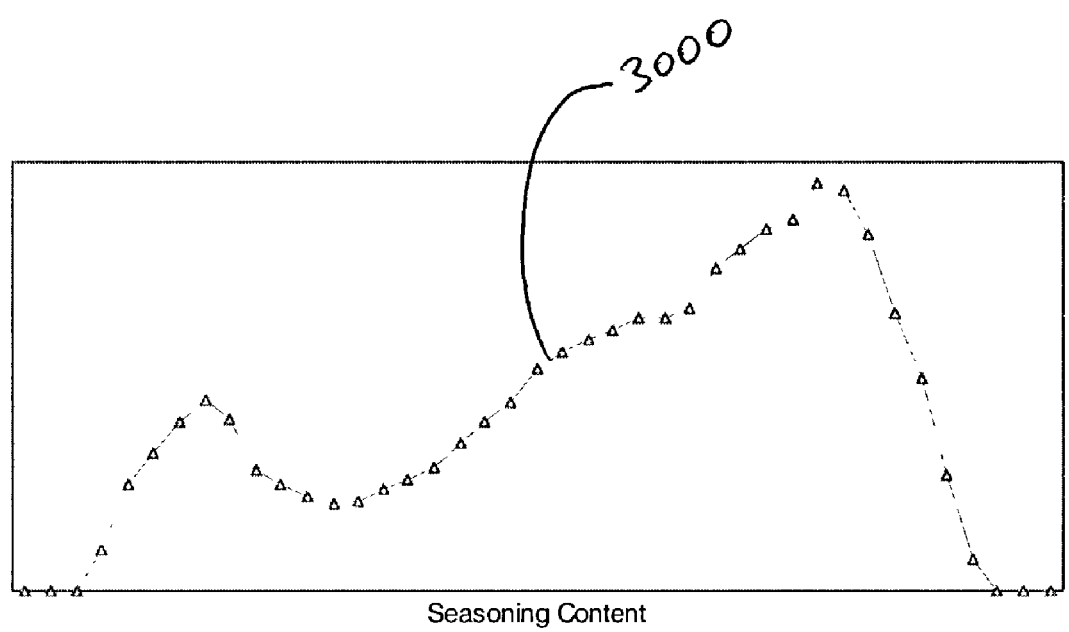
FIG. 30 is a seasoning distribution plot of image #5 in FIG. 29 according to one embodiment of the inventive method disclosed herein.

To understand further what happened in the process during that time period, FIG. 29 shows eight product images, corresponding to the eight numbers (1–8) below each image shown on the graph FIG. 28. By observing these images, it is noted that because of the coating slurry rate dropping to zero, unseasoned product was being fed to the system during this period. This unseasoned product was mixed with seasoned product in the tumbler leading to the mixture of products shown in the images in FIG. 29. The variance of the coatings distribution first decreased (unseasoned product in the image marked as #2 in FIG. 29) and then increased as the images contained mixtures of the two products (the image marked as #3 in FIG. 29). Reviewing the coating distribution plot consisting of data points 3000 (FIG. 30) of the image marked as #5, as estimated from the small window strategy, it shows a bimodal distribution as expected.

Closed Loop Control Results

Figure 31:
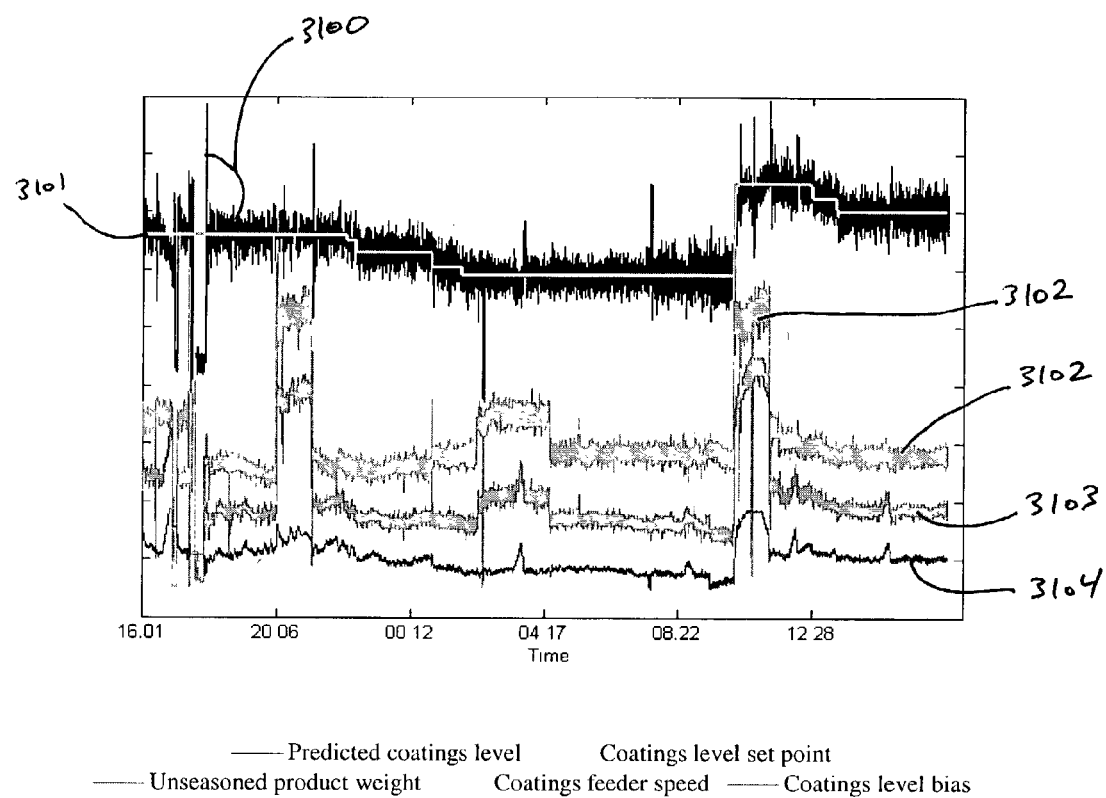
FIG. 31 is a graphical depiction of the seasoning level set point, the predicted seasoning level, the unseasoned product weight and seasoning feeder speed according to one embodiment of the inventive method disclosed herein.

Finally, operating data under closed-loop control covering a period of 24 hours is shown in FIG. 31 for product A. Line 3100 represents the predicted coating level. Line 3101 represents the coating level set point. Line 3104 and line 3103 represent the unseasoned product weight and coatings feeder speed respectively. Line 3102 indicates coatings level bias change, which is used as the manipulated variable. It is observed that the coating level successfully tracked the set point. Another point to note is that the saw-tooth effect of the coating feeder system that was apparent in FIGS. 25, 26 and 27 is no longer as noticeable. This is due to an operational change introduced to eliminate this effect.

In particular, it will be understood that the source data may be an image captured in a range of predetermined wavelengths which is not limited to the visible spectrum. The images of the snack food could, for example, be captured in the near infra-red spectrum. For convenience, the current work is most easily carried out in the visible spectrum using three colour channels, red, blue and green. It will be understood that using the visible spectrum may not be desirable or appropriate in other applications. In the preferred embodiment described above, the food is illuminated with visible light to obtain the image of a product of the process. In other processes, it may not be necessary to illuminate the object.

As described above, lighting variations may influence the overall feature variable values. Under ideal conditions, the product under inspection would remain at a fixed distance from the light-emitting source so as to provide a consistent light reflective surface with a consistent density of light over the surface area of the product. As the distance of the measured product to the light emitting sources changes, the density of light reflecting from the product will change. This will in turn change the feature variable values. By moving the product to different distances from the light and camera and measuring the resultant change in the predicted feature values, then performing a regression method to correlate the feature value to distance between product and sensor, a model can be developed to predict changes in product feature values for changes in product bed depth when the camera and light source is stationary. Conversely, changes in feature values when seasoning concentration or other feature values affecting phenomena are static, can be used to predict the bed depth of the product or change in distance of the product from the stationary sensor.

In a similar manner, the specific density or bulk density of a product can also have an effect on the measurement of a product feature that is dependent on these variables. The measurement of the amount by weight of coating on a product will be affected if the surface area does not change by the same amount as the weight of the product. Therefore, in measurement of surface area product features, the density of the product can be taken into account and modeled so that a prediction of feature concentration by weight or volume can be made. In addition, the specific density or bulk density of the product can be predicted using the measured surface feature coverage values, surface feature application rate, and weight of the base product.

Flame Analysis Embodiment

Another exemplary alternative embodiment of the invention disclosed herein is described below with reference to a process in which a flame product characterizes the underlying process. Because the flame is luminous, no external source of lighting is required. It will also be understood that the radiation emanating from a flame will cover a wide range of wavelengths which are not limited to the visible spectrum.

In many industrial furnace and boiler systems, television systems have been installed. However, they are used mainly for live displays of the flames. Most of the time the only information the flame images provide is whether the flames are burning. Because combustion processes are highly turbulent, the flames appear in a constant movement, and even the most experienced operator often finds it hard to determine the performance of the combustion.

In this situation, a monitoring system based on image analysis can become very helpful. In this alternative embodiment of the invention disclosed herein, an industrial steam boiler is observed. The fuels used for this boiler may a waste liquid stream from other processes and natural gas. Therefore, the composition of the fuel is often variable. An analog colour camera is installed and the flames behavior is recorded onto several videotapes and a video card is used to convert the analog signals into digital images. Alternatively, a flame grabber may be used for on-line analog-digital conversation.

To analyze the colour images, a Multivariate Image Analysis (MIA) technique is utilized. Nine features are extracted from score plot space for each image. Moreover, Multivariate statistical methods, such as Principal Component Analysis (PCA) and Partial Least Square (PLS) may also be performed on the image features and the process measurements to help understanding the relationship between the feature variables and the process variables.

System Setup

Figure 32:
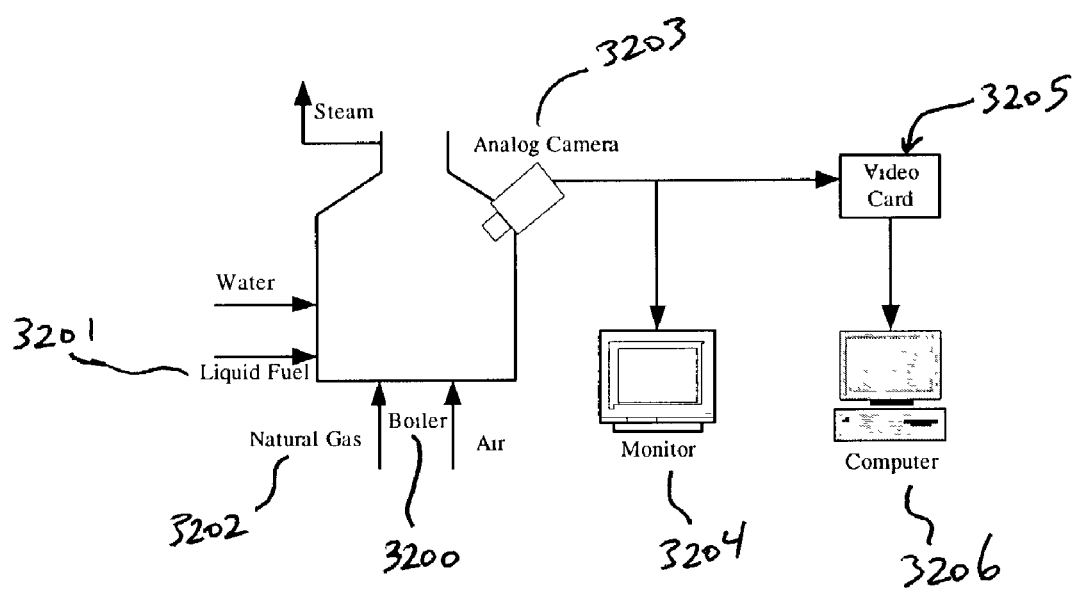
FIG. 32 is a schematic diagram depicting a flame analysis embodiment of the invention integrated into a steam boiler according to the inventive method disclosed herein.

A schematic diagram of the flame monitoring system is shown in FIG. 32. The steam boiler 3200 studied in this paper uses both the waste liquid streams 3201 from other processes and natural gas 3202 as fuels. Therefore, the compositions of the fuels often change dramatically. An analog colour camera 3203 has been installed in the boiler 3200 and is connected with a monitor 3204 for displaying the live images. In this example, the analog signals were recorded and converted into digital images by video card 3205 which were then analyzed by computer 3206 according to the methods disclosed herein. The resulting images are RGB colour images with a 120×160 pixel size. Considering the processing time, the imaging sample time is set as 1 frame per second.

Two cases studies are presented to exemplify the application of the invention. Case I is a 114 minute process (see FIG. 33). In this period of time, a liquid fuel (A) is used. In the first half of this period of time, liquid fuel decreases from 12,000 K pound per hour (kp/hr) to 6,000 kp/hr; in the second half of the time period, it increased back to 12,000 kp/hr as depicted by the data points line 3300. The steam generated followed the same trend as the fuel flow as shown by the data points line 3301.

Case II is a 56 minute process. In this case, both a liquid fuel (B) and natural gas are used.

Since this is a process to shut down liquid fuel, during this period of time the flow rate of liquid fuel represented by data points line 3400 is gradually reduced from 7000 kp/hr to 0 kp/hr and, at the same time, the flow rate of natural gas represented by data points line 3401 increased from 203 kscf/hr to 253 kscf/hr to keep the steam generated at the certain level. The flow rate changes of fuels are shown in FIG. 34-*a* and the consequently change of the steam flow rate is shown by reference to data points line 3402 in FIG. 34-*b*. In both cases, the air/fuel ratio of the boiler is automatically modulated based on a pre-set control scheme. Therefore, only flow rates of the fuels are considered.

Figure 35:
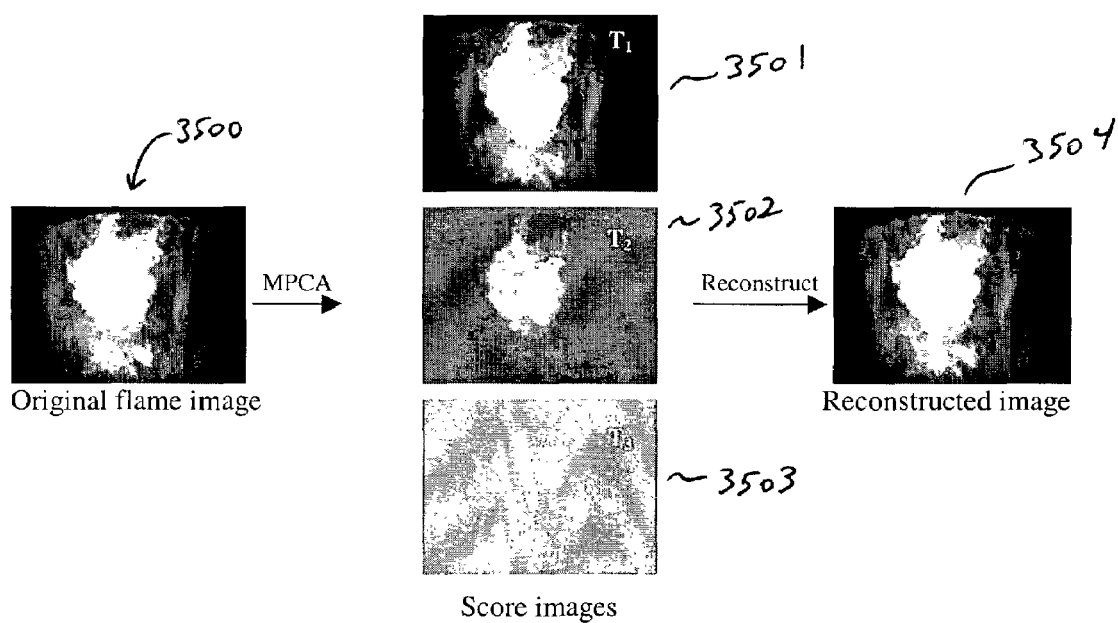
FIG. 35 is a series of flame images showing the transformation of an original flame image to a reconstructed image using principal score images.

For Case I, a total of 6,840 frames are obtained and for Case II 3,360 image frames are obtained. In FIG. 35-*a*, sample images are shown corresponding to the points (A~F) marked in FIG. 33 and FIG. 34. For each point, two consecutive images with a one second time difference are shown. It is reasonable to assume that during this one second, the global combustion condition kept constant. It can be observed that the flames in the boiler appeared highly turbulent, which brings about the difficulty to extract stable and reliable information about the combustion process. It should be noted that the camera positions are not exactly the same for Case I and Case II. However, the outcome of these studies show that this difference in camera location is not a significant influence.

A flame image is captured which results in a RGB colour image. The colour image is expressed as a 3-way matrix. Two dimensions represent the x-y spatial coordinates and the third dimension is the colour channel. Therefore, it is a multivariate image composed of three variables (R, G and B channels). In this embodiment, the feature variables extracted are obtained using Multivariate Image Analysis (MIA) techniques, which are based on multi-way Principle Component Analysis (PCA).

Without considering the spatial coordinates of pixels, we can unfold the image matrix and express it as a 2-way matrix.

$$I_{N_{row} \times N_{col} \times 3} \xrightarrow{unfold} I_{N \times 3} = \begin{bmatrix} c_{1,r} & c_{1,g} & c_{1,b} \\ M & M & M \\ c_{i,r} & c_{i,g} & c_{i,b} \\ M & M & M \\ c_{N,r} & c_{N,g} & c_{N,b} \end{bmatrix} = \begin{bmatrix} c_1 \\ M \\ c_i \\ M \\ c_N \end{bmatrix}$$

I is the three-way image matrix with image size $N_{row} \times N_{col}$. I is the unfolded two-way image matrix. N is the number of pixels in the image, $N = N_{row} \times N_{col}$. $c_{i,r}$, $c_{i,g}$, $c_{i,b}$ (i=1, ... ,N) are the intensity values of the R, G and B channels for pixel i. $c_i$ (i=1, ... , N) is the i-th row vector of I, which represents the colour values of pixel i. Multi-way PCA is equivalent to performing PCA on the unfolded image matrix I.

$$I = \sum_{k=1}^{K} t_k p_k^T + E$$

where K is the number of principal components, the $t_k$'s are score vectors and the corresponding $p_k$'s are loading vectors. For RGB colour image, the maximum number of principal components is three.

Since the row dimension of the I matrix is very large (equal to 19,200 for a 120*160 image space) and the column dimension is much smaller (equal to 3 for an RGB colour image), a kernel algorithm is used to compute the loading and score vectors. In this algorithm the kernel matrix ($I^T I$) is first formed (for a set of images, kernel matrix is calculated as $$\sum_j I_j^T I_j),$$

and then singular value decomposition (SVD) is performed on this very low dimension matrix (3×3 for an RGB colour image) to obtain loading vectors $p_a$ (a=1, . . . A).

After obtaining loading vectors, the corresponding score vectors $t_k$ are then computed via $t_k = I \cdot p_k$. $t_k$ is a long vector with length N. After proper scaling and rounding off, it can be refolded into the original image size and displayed as an image.

$$s_{k,i} = \text{Round}\left(\frac{t_{k,i} - t_{k,\min}}{t_{k,\max} - t_{k,\min}} \times 255\right), i = 1, \ldots, N$$

$$(s_k)_{N \times 1} \xrightarrow{refold} (T_k)_{Nrow \times Ncol}$$

$T_k$ is the score image of component k. The values of $T_k$ are integers from 0 to 255. It should be pointed out that when many images are studied, a common scaling range ($t_{k,min}$ and $t_{k,max}$) should be used for all the images.

One hundred images are used in this example to compute the loading matrix and score scaling range. The first two components explained 99% of the total variance. In FIG. 35, three score images 3501, 3502, 3503 are shown for a sample image 3500. A reconstructed image 3504 from the first two components 3501, 3502 is also shown. It is observed that the $T_3$ score image 3503 contains very little information, which is mainly noise. The reconstructed image 3504 from the first two components 3501, 3502 is almost the same as the original image 3500. Since the first two components 3501, 3502 explain most of the variance, instead of working in the original 3-dimensional RGB space, working in the 2-dimensional orthogonal $t_1$–$t_2$ score space allows us interpret the images 3501, 3502 much more easily.

Inspection on the $t_1$–$t_2$ score plot is a common tool in general PCA analysis to give an overview of the whole system and/or detect clusters or outliers. However, when studied objects are images, because of large number of pixels in $t_1$–$t_2$ score plot many pixels would fall overlap each other. A 256×256 histogram is used to describe the $t_1$–$t_2$ score plot space in this situation and a colour coding scheme is used to indicate the intensity of the pixel locations in the score plot. This two-dimensional histogram, denoted as TT, can be obtained from rounded and scaled $T_1$ $_{and}$ $_{T2}$ score images. TT is a 256×256 matrix and computed as $$TT_{i,j} = \sum_{k,l} 1, \forall (k, l), T_{1k,l} = i - 1 \& T_{2k,l} = j - 1$$

$i, j = 1, \ldots 256, k = 1, \ldots, 120, l = 1, \ldots, 160$

Figure 36:
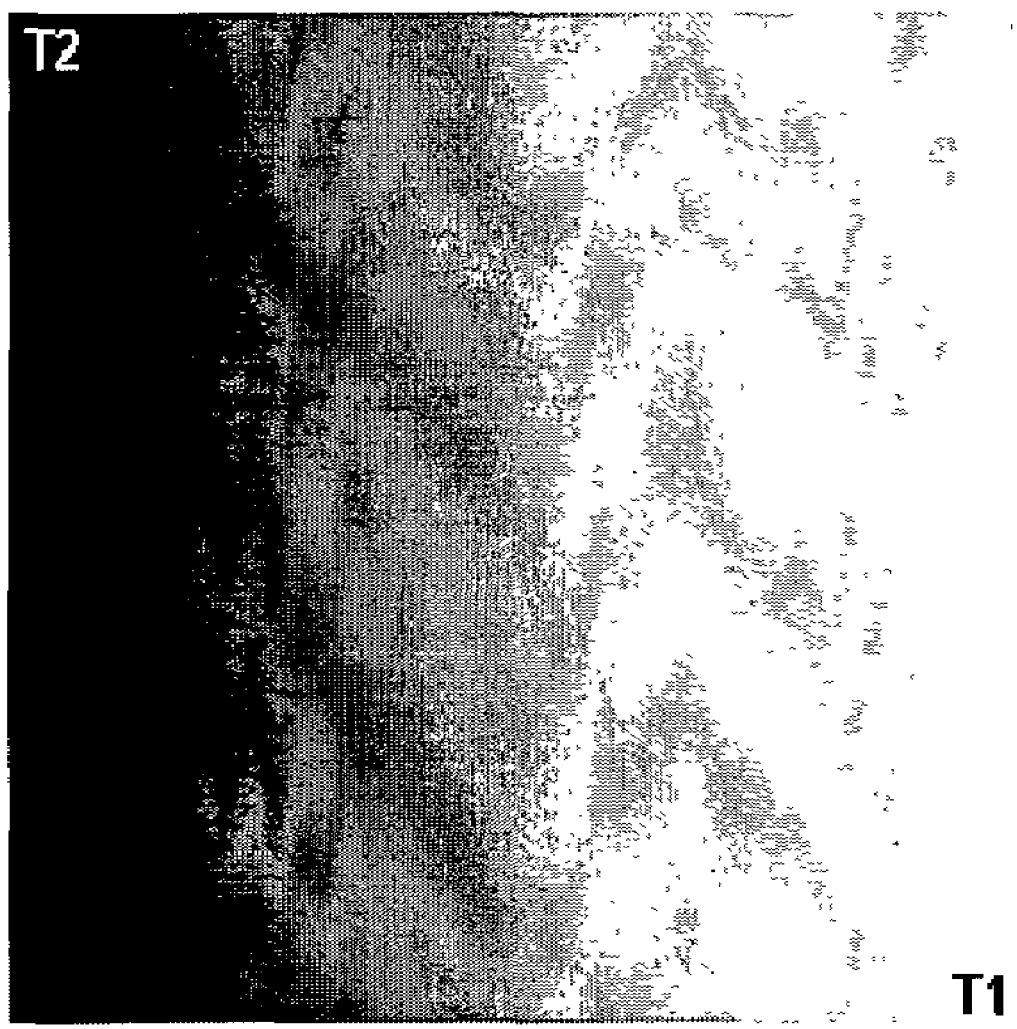
FIG. 36 depicts a colour plane image for a $t_1$ $t_2$ score plot of the reconstructed flame images shown in FIG. 35.

FIG. 36-*a* shows the corresponding score plots for the sample images shown in FIG. 35-*a*. In the colour scheme of the score plots, a darker colour indicates a lower intensity (black indicates no pixel falling) and a brighter colour indicates a higher intensity.

It observed from FIG. 36-a that for the same combustion condition, the locations of pixels in the score plots are similar. As the combustion condition changed, the locations of pixels also changed. Each location in T1–T2 score plot represents certain kind of colour (ignoring the variation in $t_3$). The colour for each location may be computed by $$[R\ G\ B]_{ij} = t_1(i) \cdot p_1^T + t_2(j) \cdot p_2^T, i,j=1, \ldots 256$$

$$t_1(i) = (i-1) \cdot (t_{1,max} - t_{1,min}) + t_{1,min},\ t_2(j) = (j-1) \cdot (t_{2,max} - t_{2,min}) + t_{2,min} \quad (1)$$

A colour plane is then computed for score plot as shown in FIG. 36. The relation between the position in score plot and the colour is observed. Because under different combustion conditions, the colours of the flames are different, we observe the movement in score plot space.

Score plots contain important information about the flame; however, directly monitoring the process based on score plots is not practical. This is due mainly in part to (1) it is difficult for people to monitor a time series process by observing the changes in a two dimensional matrix and (2) even for people able to detect some change occurring in a score plot, it is still quite difficult to relate such changes with the changes in the process variables. Therefore, it is desired to extract features that have more physical meaning to the observer and further relate those features with the process measurements to help one gain a greater understanding of flames and the combustion process.

Basically, the features discussed in this alternative embodiment can be divided into two categories. The first category is called luminous features, including flame luminous region area, flame brightness, flame intensity uniformity and the furnace wall intensity. The second category is called colour features, including average colour of the whole image, average colour of the flame luminous region and the number of colours appeared in the flame region.

Figure 37:
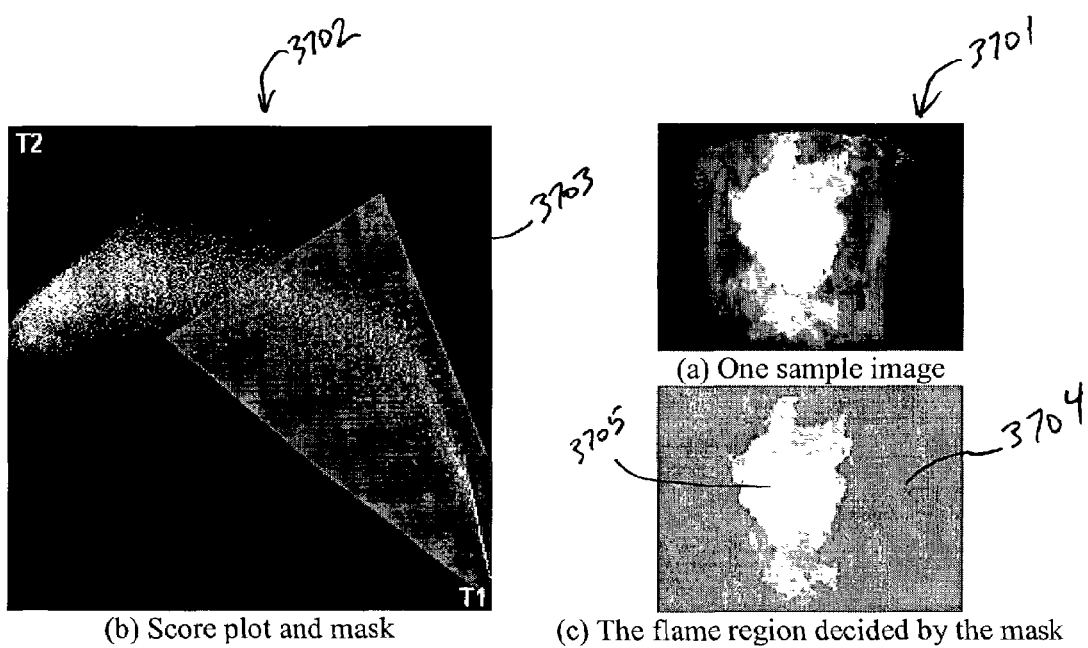
FIGS. 37-a through 37-c show a sample flame image and corresponding flame region after applying a mask shown on the score plot of FIG. 37-b.

The flame luminous region is selected by choosing a flame mask in the score plot space. The mask is a 256×256 binary matrix, denoted by M. A pixel value is equal to 1 if the colour of this location is a flame colour, otherwise is equal to 0. The dimension of the mask is made by trial and error. The final mask for the flame is shown in FIG. 37. Specifically, in FIG. 37-a, a sample image 3701 is shown. The corresponding score plot 3702 is shown in FIG. 37-b. The mask of flame region is shown as the triangular area 3703. If all pixels falling outside this mask are depicted as gray colour 3704, the image shown in FIG. 37-c is obtained. It is then observed that the flame region 3705 is separated from the other parts of the image.

Luminous Region Area

The luminous region area is the area of the flame region defined above. It can be easily computed by counting the number of the pixels falling into the flame mask.

$$A = \sum_{i,j} TT_{i,j},\ \forall\ (i,j),\ M_{i,j} = 1,\ i,j = 1, \ldots 256$$

Flame Brightness

Flame brightness can be obtained by integrating luminous intensity level contributed from all pixels fall inside the luminous region. The luminous intensity level for any location in score plot is computed by converting the colour plane obtained by eq. (1) to a gray scale plane as follows $$L_{i,j} = [R\ G\ B]_{i,j} \cdot \begin{bmatrix} 0.299 \\ 0.587 \\ 0.114 \end{bmatrix},\ (i,j) = 1, \ldots, 256$$

in which $L_{ij}$ is the luminous intensity level for location (i,j) in score plot. Therefore, the flame brightness is calculated as:

$$B = \sum_{i,j} TT_{i,j} \cdot L_{i,j},\ \forall\ (i,j),\ M_{i,j} = 1$$

Flame Luminous Uniformity

Flame luminous uniformity is defined as the standard deviation of luminous intensity of flame region:

$$U = \sqrt{\frac{\sum_{i,j} TT_{i,j} \cdot L_{i,j}^2 - \sum_{i,j} TT_{i,j} \cdot L_{i,j}}{\sum_{i,j} TT_{i,j}}} = \sqrt{\frac{\sum_{i,j} TT_{i,j} \cdot L_{i,j}^2 - B}{A}},$$

$$\forall\ (i,j),\ M_{i,j} = 1$$

Average Brightness of the Boiler Wall

From observation of the sample images shown in FIG. 35-a, the installed camera is facing the flame, which means blocks the ability to see the length of the flame. Moreover, the flame image is a two dimensional projection of a three dimensional field and only part of the flame is captured in the image. The brightness of the boiler wall yields information of the flame length and/or the volume of the flames. The average brightness of the boiler wall is computed by:

$$W = \frac{\sum_{i,j} TT_{i,j} \cdot L_{i,j}}{\sum_{i,j} TT_{i,j}},\ \forall\ (i,j),\ M_{i,j} = 0$$

Average Colour of the Whole Flame Image

The average colour of the whole flame image is expressed as the average location of pixels in score plot.

$$T_{1m} = \frac{\sum_{i,j} TT_{i,j} \cdot (i-1)}{N},\ T_{2m} = \frac{\sum_{i,j} TT_{i,j} \cdot (j-1)}{N},\ i,j = 1, 2, \ldots 256$$

in which N is the total number of pixels in the image.

Average Colour of the Flame Region

The average colour of the flame region is defined as the average location of the pixels belonging to the flame region.

$$T_{1f} = \frac{\sum_{i,j} TT_{i,j} \cdot (i-1)}{A}, T_{2f} = \frac{\sum_{i,j} TT_{i,j} \cdot (j-1)}{A}, \forall (i, j), M_{i,j} = 1$$

Number of Colours Appearing in the Flame Region

The number of the different colours appeared in the flame region is the area of flame region in the score plot space.

$$N_c = \sum_{i,j} 1, \forall (i, j), TT_{i,j} \cdot M_{i,j} \neq 0$$

Because of the high turbulence in the combustive process, the feature variables express large variations making it difficult to see the trend of the process. An effective way to reduce these variations is to filter the raw data.

There are several possible filtering techniques which can be used at the different stages of the calculation. The first one is to perform the filtering operation in the image space. This is the most commonly used method of preprocessing flame studies in the literature. However, in the highly turbulent flame circumstance, as shown in the example averaged image 3800 in FIG. 38-a, averaging in the image space could lead to a loss of flame characteristics. In the score plot space 3801, the shape of the averaged image (see FIG. 38-b) has been 'distorted' compared to the single frame image (the score plots of point A in FIG. 36-a).

The second filtering technique is to perform a filter on the score plot space. FIG. 39 shows an averaged TT score plot 3900. Compared to FIG. 38-b, this averaged score plot 3900 keeps the basic shape of the score plot of the individual image 3801. The feature variables extracted from the averaged score plot 3900 are expected to summarize the characteristics of the flame during the short period of time. However, the values of the features extracted from the filtered score plots may have different numerical amounts from the features extracted from the raw images because the calculation of feature extraction is not linear.

The third filter approach is to apply a filter on the extracted feature variables of the individual frame. This approach has several advantages compared to the other two filtering techniques discussed herein. First, it is much easier to handle the time series data such that at each time point, the data is a vector rather than a matrix. Second, the filtered data points have integrity with the raw feature variables. In this embodiment, we use the function 'filtfilt' in Matlab Signal Processing Toolbox to perform the filtering operation on the raw feature variables. This function performs zero-phase digital filtering by processing the input data in both the forward and reverse directions. After filtering in the forward direction, it reverses the filtered sequence and runs it back through the filter. The resulting sequence has precisely zero-phase distortion. In addition to the forward-reverse filtering, it also attempts to minimize startup and ending transients by adjusting initial conditions. The filter weights used in this example is an averaging filter with window length of 60. In fact, filtered features obtained by these three filters in most cases show similar trends. However, since the third filter is the simplest one and the smoothest results are obtained, it is selected as the filter in the following computation example.

Figure 40:
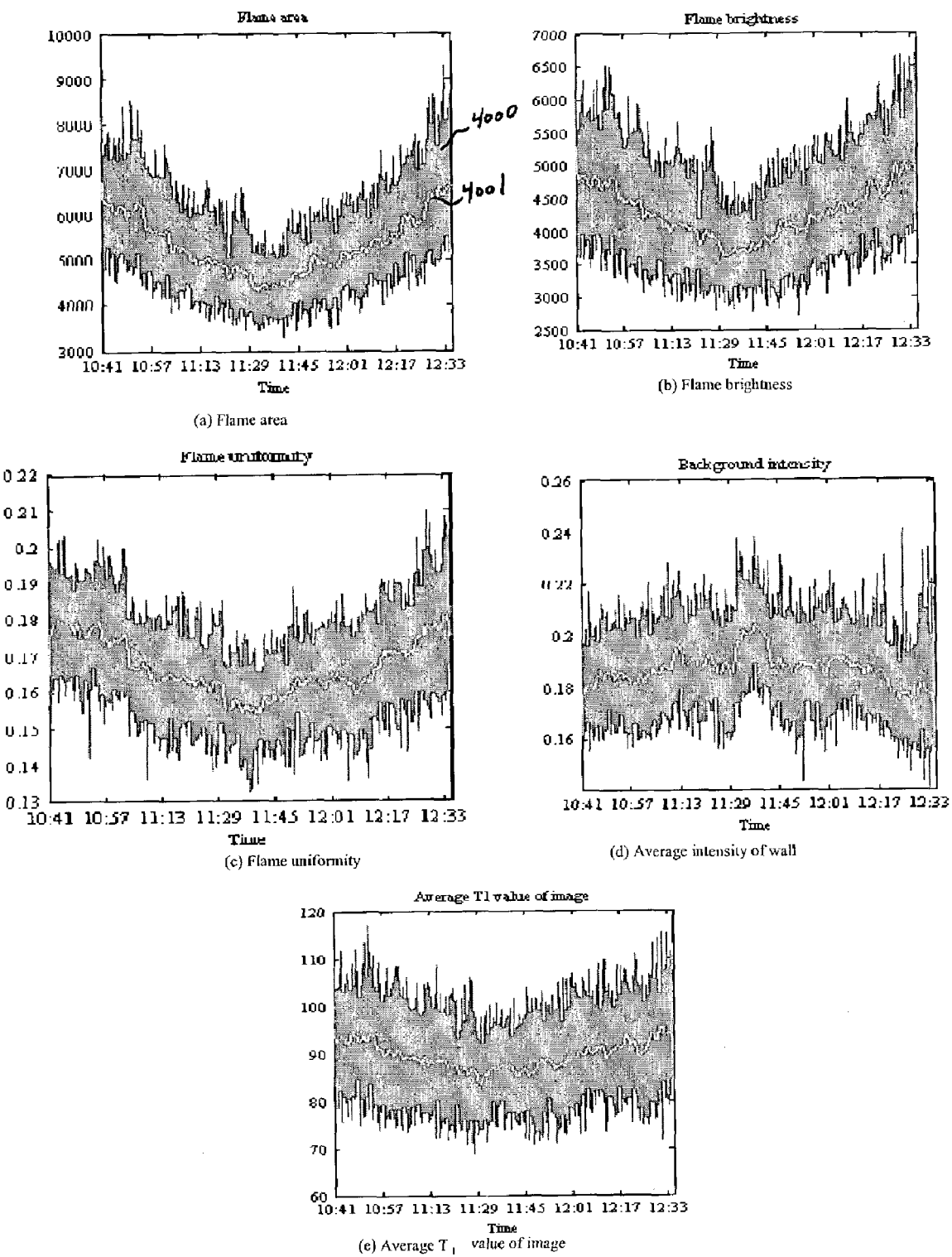
FIGS. 40-a and 40-b is a series of plots of feature variables for case I with light lines representing filtered values and the dark regions representing raw data values.
Figure 40:
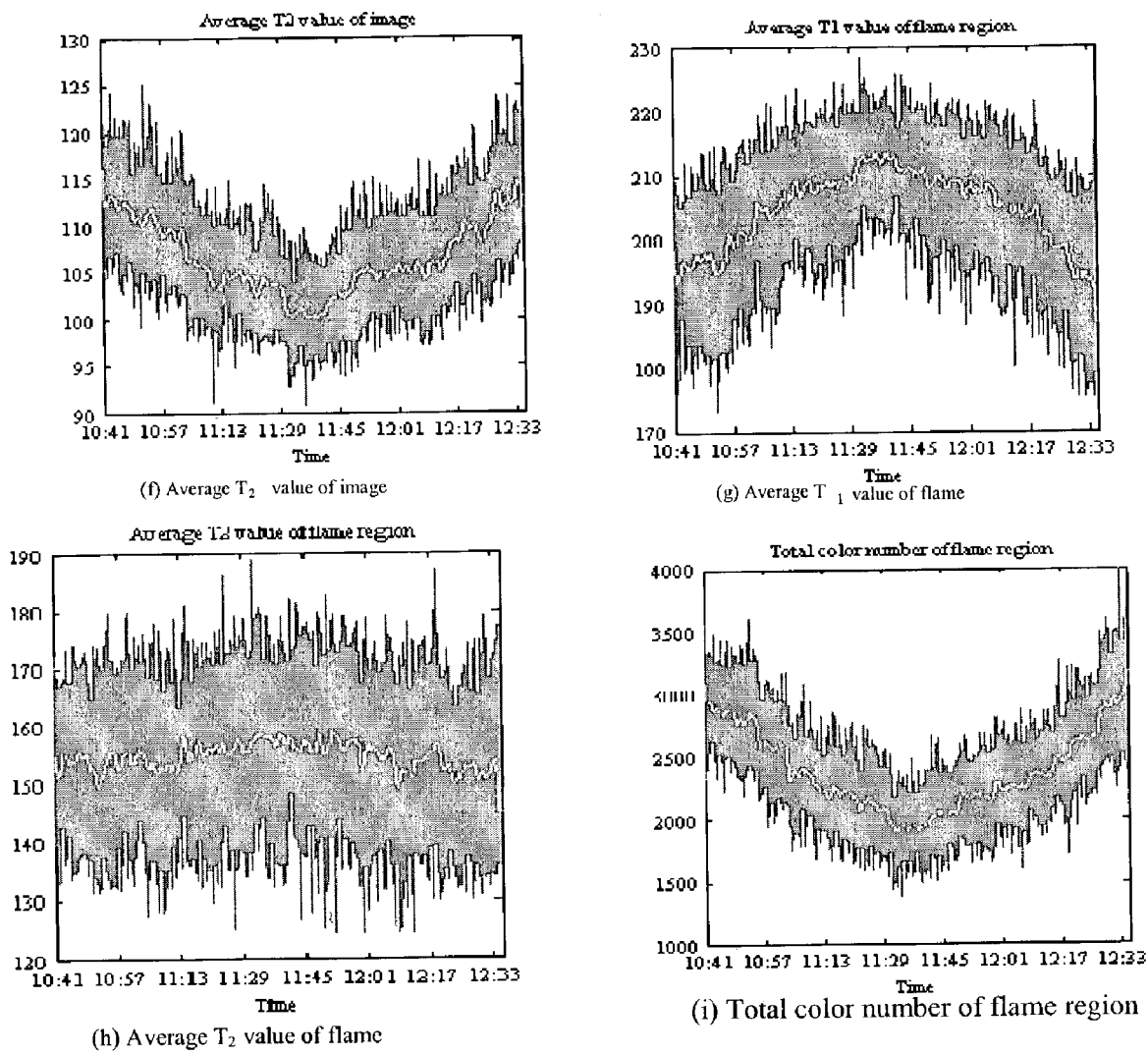
Figure 41:
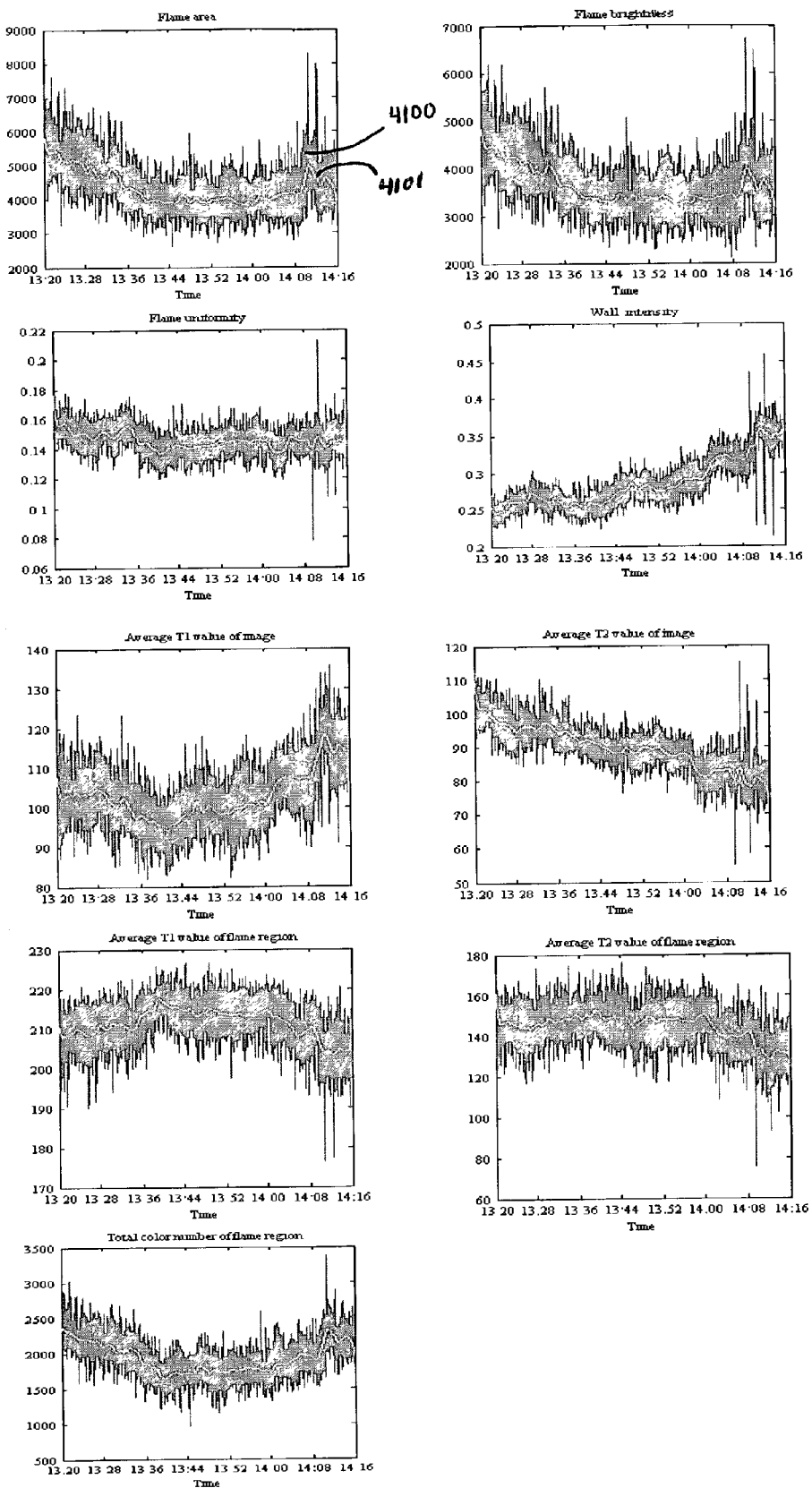
FIGS. 41-a and 41-b is a series of plots of feature variables for case II with light lines representing filtered values and dark regions representing raw data values.
Figure 41A:
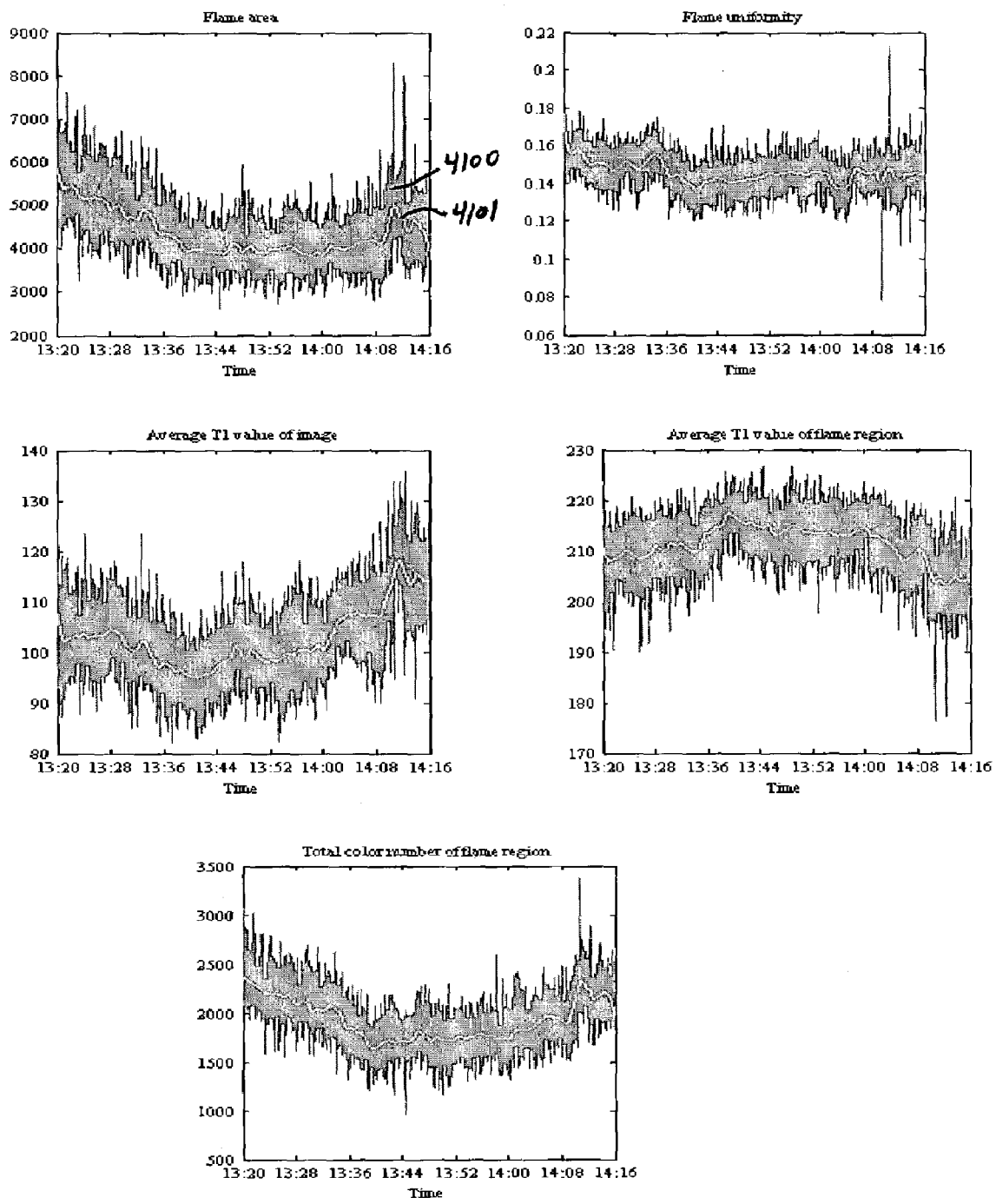
Figure 41:
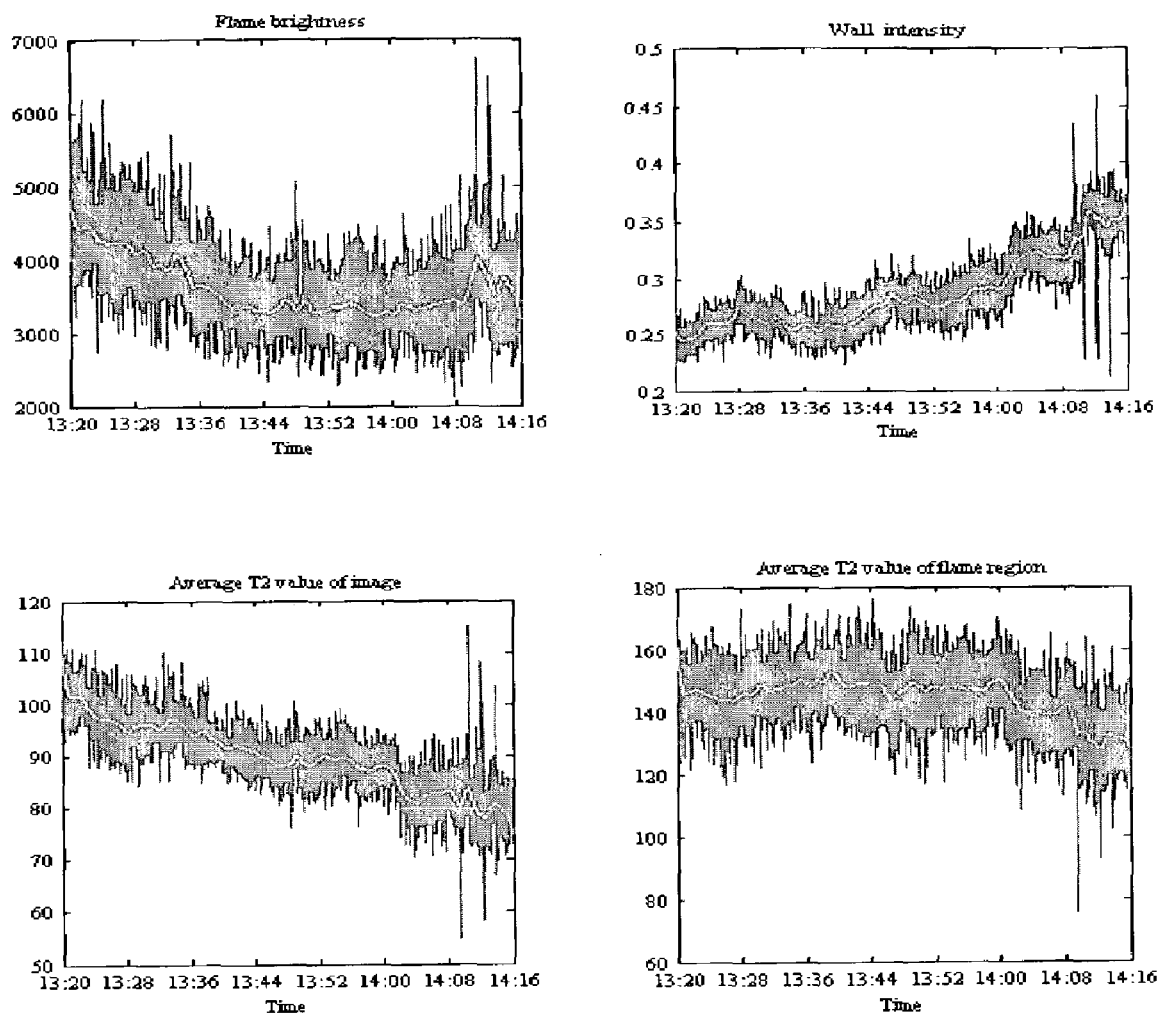

FIG. 40 and FIG. 41 are depictions of the feature variables for the following pair of case examples which include, flame area (FIG. 40-a and FIG. 41-a), flame brightness (FIG. 40-b and FIG. 41-b), flame uniformity (FIG. 40-c and FIG. 41-c), average intensity of the boiler wall (FIG. 40-d and FIG. 41-d), average $T_1$ value of image (FIG. 40-e and FIG. 41-e), average $T_2$ value of image (FIG. 40-f and FIG. 41-f), average $T_1$ value of flame (FIG. 40-g and FIG. 41-g), average $T_2$ value of flame (FIG. 40-h and FIG. 41-h), and the total colour number of the flame region (FIG. 40-i and FIG. 41-i). In Case I, the darker areas of the graphed data points 4000 represent raw data values, while line 4001 represents the filtered values. Liquid fuel (A) flow rate first decreased and then increased back to the original value. We can see from FIG. 40, all the feature variables follow the same trend or the inverse trend as the liquid fuel flow rate changes. Likewise, in case II the darker areas of the graphed data points 4100 in FIGS. 41a-h, represent raw data values, while line 4101 represents the filtered values. In case II, both the liquid fuel (B) and natural gas flow rate were variable. Therefore, in Case II the trends of the feature variables are different. Compared to FIG. 34, it is observed that some of the trends are similar to the liquid fuel flow rate change, such as the average $T_2$ value of the whole image; some of the trends are similar to the natural gas flow rate change, such as average $T_2$ value of the flame region. To have a better understanding of the relation between image feature variables and process measurements, multivariate statistical methods, such as Principal Component Analysis (PCA) and Partial Least Square (PLS), are used to obtain more qualitative and quantitative information about the process changes.

Next, three PCA models are obtained for the Case I data, the first half of Case II data and the whole Case II data, respectively. The purpose is to reveal the relationship between the changes of the fuels and the flame properties. The variables included in the PCA models constitute filtered flame feature variables and fuel(s) flow rate.

Model 1: Case I Data

Figure 42:
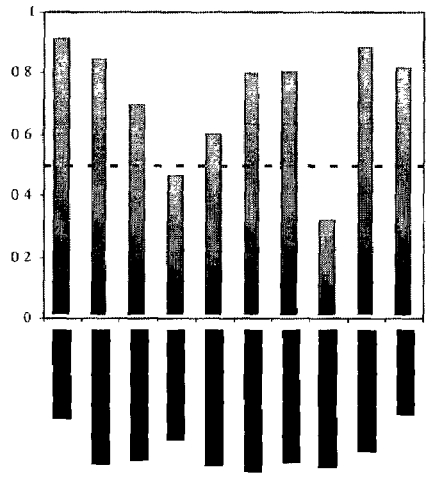
FIG. 42 is a bar graph showing the prediction power of the PCA model for case I.
Figure 43:
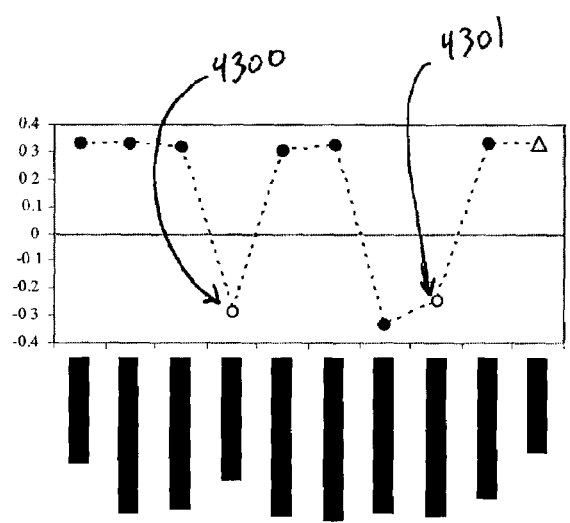
FIG. 43 is a loading plot of the 1$^{st}$ component of the PCA model for case I.

In the PCA model for case I, the $1^{st}$ principal component explained 88.4% of the total variance. This is reasonable since only one factor (flow rate of liquid fuel) is changing in this case. FIG. 42 shows the prediction power for the variables. $v_4$ (wall intensity) and $v_8$ (mean $T_2$ of flame) have low prediction power, which indicates that these two variables contain relatively little information related the variation of other variables. From FIGS. 40-d and 40-h, it is observed that $v_4$ and $v_8$ have a very flat changing trend, which is consistent with the conclusion from the prediction power plot. Therefore, in the loading plot shown in FIG. 43, the values of these two variables (indicated by the unfilled circles 4300 and 4301) were not considered. From the loading plot depicted in FIG. 43, we can see that with the exception of $v_7$, which has a negative correlation, all other variables have a positive correlation relationship.

Model 2: First Half of Case II Data

In the first half period time of Case II, only the flow rate of liquid fuel (B) decreased and flow rate of natural gas almost kept constant. The $1^{st}$ principal component explained 76.7% of the total variance. It is interesting to see from the predict power plot (FIG. 44) and loading plot (FIG. 45) that almost the same relationship between flame image feature variables and liquid fuel flow rate exists although the compositions of the two liquid fuels in these two cases were different.

Model 3: Whole Case II Data

In the PCA model for whole case II, the $1^{st}$ component explained 52.3% and the $2^{nd}$ component explained 42.6% of the total variance. In the prediction power plot (see FIG. 46), we can see that only $V_3$ (flame uniformity) has low prediction power. This is different from Model 1 and Model 2. It is probably because the variation of natural gas has little influence on $V_3$, $v_4$ and $v_8$, which had low prediction power in Model 1 and Model 2, now have high prediction power. This indicates that these two variables have close relationships with natural gas flow rate. From the scatter $p_1$–$p_2$ loading plot (FIG. 47) it is observed that $v_4$ has high positive correlation and $v_8$ has negative correlation with Natural Gas. A PCA model is then performed on both datasets. The variables included are flame image feature variables. In total, only two principal components are significant, explaining 97.4% of the variance.

Figure 48:
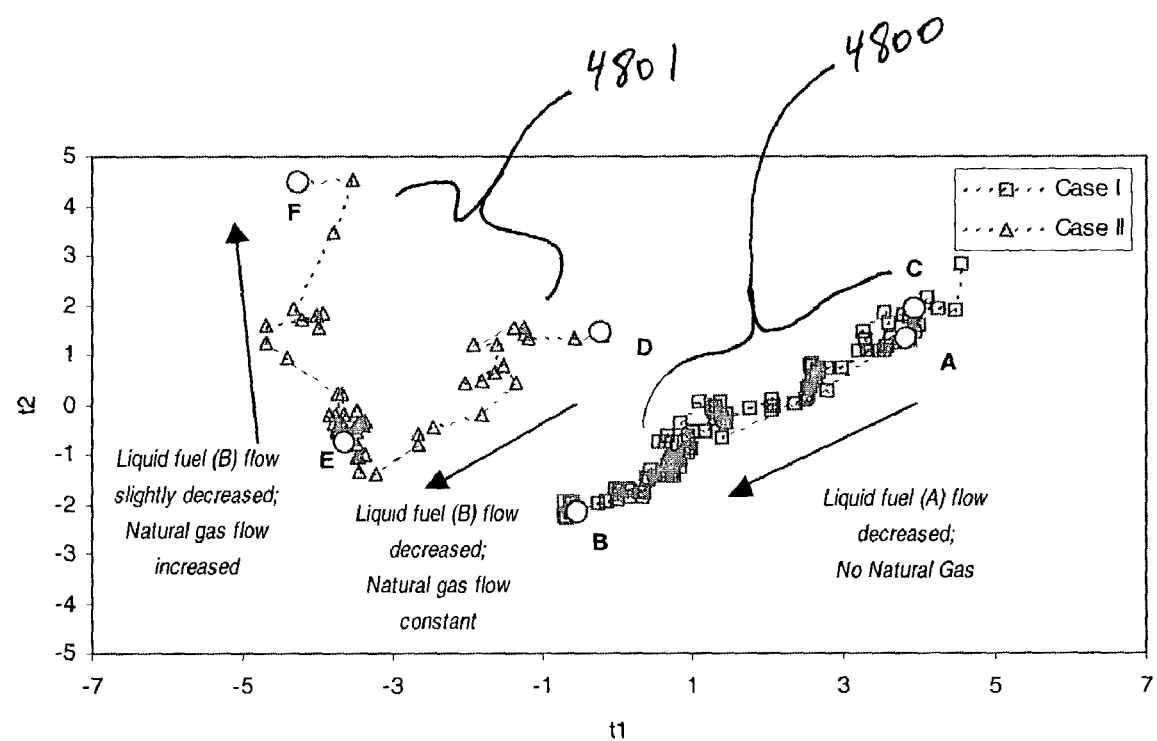
FIG. 48 is a $t_1$ $t_2$ score plot of the PCA model for both cases I and II.

The flame analysis process may be monitored by observing the t1–t2 score plot depicted in FIG. 48. From this score, it may be observed how the process develops as the combustion conditions change. It is interesting to note that both the points belonging to Case I 4800 and the points belonging to the first half of Case II 4801 show that as the liquid fuel decreased the points moved towards a left-bottom direction. As the flow rate of Natural Gas increased, the points moved mainly toward the $t_2$ direction. By studying and correlating properties of a flame, it is expected that predictions may be made to control the process including noxious emissions generated from the process and burning efficiency.

Figure 49:
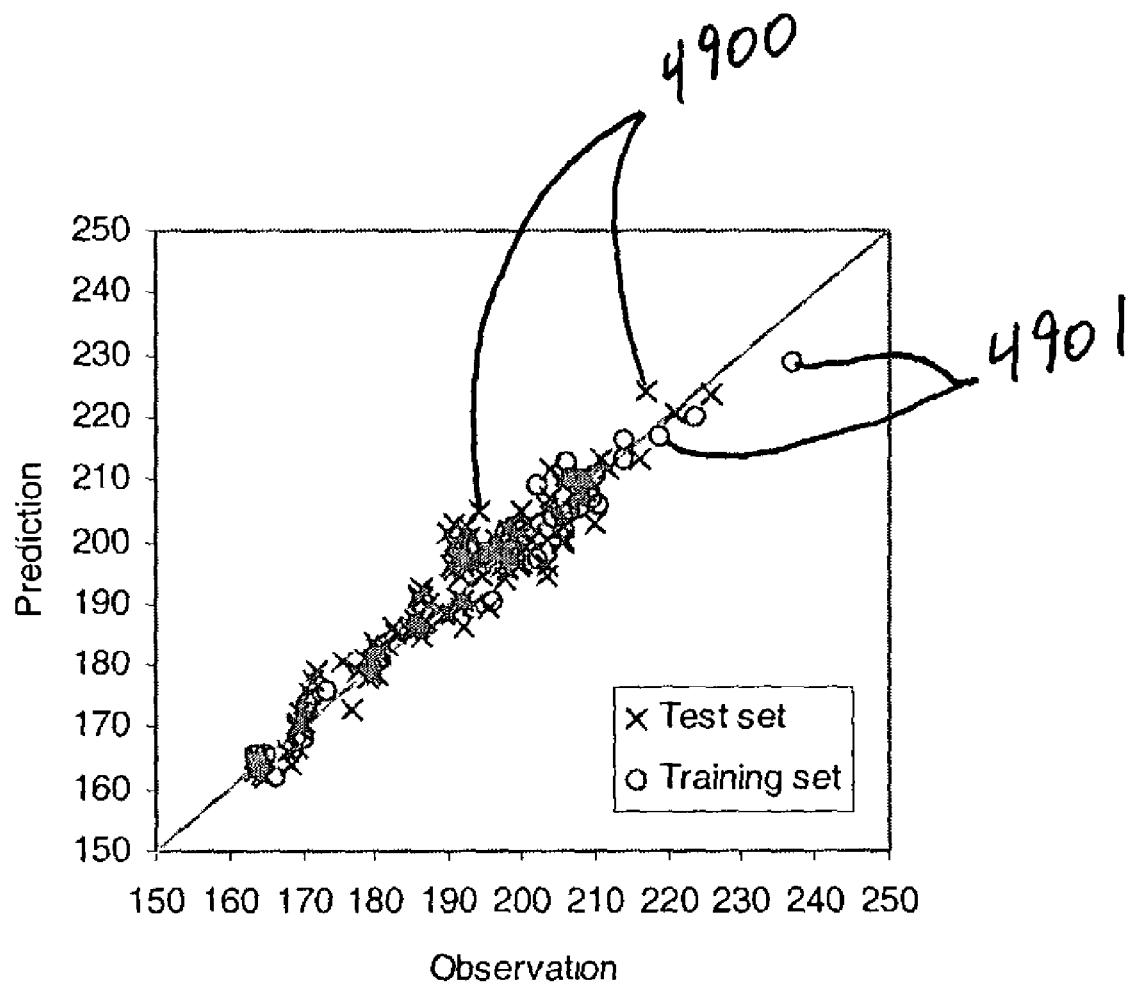
FIG. 49 is a graphical depiction of the predicted steam flow rate versus measured steam flow rate; and, FIGS. 50-a and 50-b show a comparison of steam flow rates over time for predicted values and measured values, for case I and case II, respectively.
Figure 50:
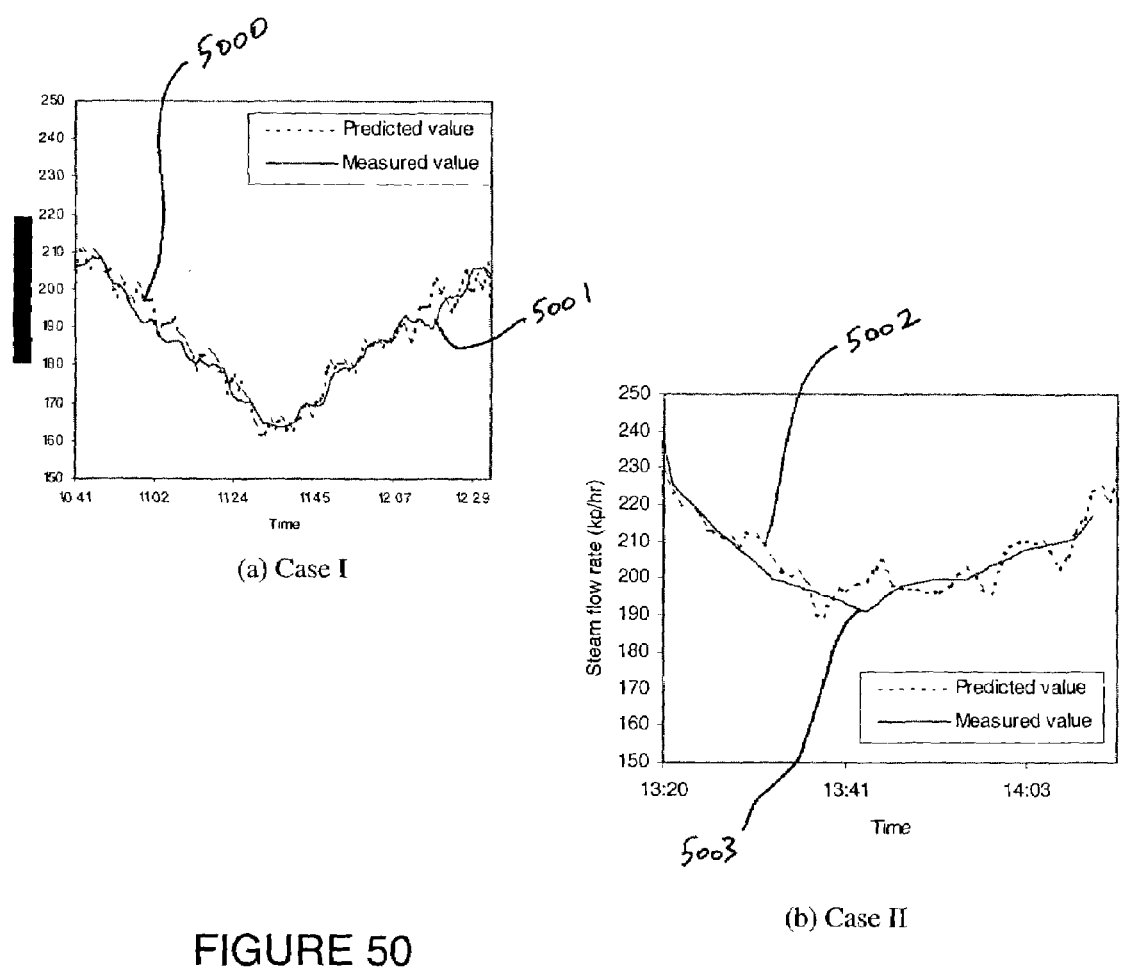

A PLS model may then be constructed to obtain more quantitative information. Feature variables from flame images can be used as predictor to predict flow rate of the generated steam. Six latent variables are used in constructing the PLS model. Thirty three observations are used as a training dataset and 133 observations are used as test dataset. The root mean square error (RMSE) for training set is 3.85 and for test set is 3.93, respectively. The prediction versus observation plot is shown in FIG. 49. FIGS. **50-*a* and 50-*b* are the time series plots for the two cases, respectively. For case I depicted in FIG. 50-*a*, data point line 5000 represents the predicted value of the steam flow rate and data point line 5001 represents the actual measured value of the steam flow rate For case II shown in FIG. 50-*b*, data point line 5002 represents the predicted value of the steam flow rate and data point line 5003** represents the actual measured value of the steam flow rate. It is observed that the predicted data points are consistent with the measured data. It is also expected that by combining the image feature variables and other relevant process variables predictions may be made to control the noxious emissions generated from the process and the burning efficiency While the invention has been particularly shown and described with reference to several embodiments, it will be understood by those skilled in the art that various other approaches and applications to industry may be made without departing from the spirit and scope of the invention disclosed herein.

We claim:

1. A method of monitoring a process producing a characterizing product, the method comprising the steps of:
    sequentially capturing multivariate images of the characterizing product, each image consisting of an image array of pixel elements of measured intensity values in at least three wavelength ranges defining the dimensions for the image array;
    creating a feature vector from said image array;
    performing a regression method to correlate the feature vector with a characterizing feature of the product; and,
    creating an output of said characterizing feature for continuous monitoring of the process.

2. A method according to claim 1 in which the multivariate image of the characterizing product is captured in the visible spectrum.

3. A method according to claim 2 in which the pixel elements of the image array have varying intensities of the colours red, green, and blue.

4. A method according to claim 1 in which the multivariate image of the characterizing product is captured in the near infra-red spectrum.

5. A method according to claim 1 in which the feature vector consists of average values for each of the said at least three wavelength ranges.

6. A method according to claim 1 in which a multivariate statistical projection method is applied to the image array to reduce the dimensions to a low dimensional score space image data defined by a small number of score vectors $t_a$ and said feature vector is created from said low dimensional score space image data.

7. A method according to claim 6 in which the multivariate statistical projection method is selected from the group comprising: multi-way principal component analysis (PCA); multi-way partial least squares (PLS); projection pursuit; independent component analysis.

8. A method according to claim 6 in which the multivariate statistical projection method applied to the image array reduces the dimensions of the image array to a $t_1$–$t_2$ score space.

9. A method according to claim 8 in which the feature vector is a first loading vector $p_1$.

10. A method according to claim 8 in which the feature vector is obtained by dividing the $t_1$–$t_2$ score space into a number of blocks and summing the intensity values within each block.

11. A method according to claim 8 in which the feature vector is created, comprising the steps of:
    applying a multivariate statistical projection method to an image array for a control process to reduce the dimensions to a low dimensional score space having a significant loading vector $t_s$;
    projecting the $t_1$–$t_2$ score space along a direction defined by said significant loading vector $t_s$ to create a projection vector V; and,
    creating a histogram from said projection vector V to define the feature vector.

12. A method according to claim 8 in which the feature vector is created comprising the steps of:
    applying a multivariate statistical projection method to an image array for a control process to reduce the dimensions to a low dimensional score space having a significant loading vector $t_s$;
    projecting the $t_1$–$t_2$ score space along a direction defined by said significant loading vector $t_s$ to create a projection vector V; and,
    creating a cumulative histogram from said projection vector V to define the feature vector.

13. A method according to claim 8 in which said feature vector is created comprising the steps of:
    calculating covariance matrices $COV_1$ and $COV_2$ between at least one histogram elements from the $t_1$–$t_2$ score space image data for two respective features $Z_1$ and $Z_2$;
    calculating an angle matrix $\theta$ from said covariance matrices $COV_1$ and $COV_2$;
    superimposing the $t_1$–$t_2$ score space image data on said angle matrix $\theta$; and,
    calculating a cumulative histogram to define the feature vector.

14. A method according to claim 8 in which said feature vector is created comprising the steps of:
  calculating covariance matrices $COV_3$ and $COV_4$ between at least one histogram elements from a $t_1$–$t_2$ score space image data for two respective features $Z_1$ and $Z_2$ in a control process;
  adding covariance matrices $COV_3$ and $COV_4$ and displaying the sum as a colour coded image sum display in a first $t_1$–$t_2$ score space;
  selecting a mask to inscribe an area A in said sum display in said first $t_1$–$t_2$ space corresponding to a product region;
  projecting the multivariate images to said first $t_1$–$t_2$ score space and removing pixels which lie outside said area A to create pure product images;
  applying a multivariate statistical projection method to the pure product images to reduce the dimensions of the pure product images to a second $t_1$–$t_2$ score space;
  calculating covariance matrices $COV_5$ and $COV_6$ between histogram elements from the second $t_1$–$t_2$ score space for said two respective features $Z_1$ and $Z_2$;
  calculating an angle matrix $\theta$ from said covariance matrices $COV_5$ and $COV_6$;
  superimposing the second $t_1$–$t_2$ score space image data on said angle matrix $\theta$; and,
  calculating a cumulative histogram to define the feature vector.

15. A method according to claim 1 in which the regression method is selected from the group comprising principal component regression (PCR); partial least squares (PLS); multivariate linear regression (MLR); artificial neural networks (ANN).

16. A method according to claim 1 in which the output is displayed as a colour coded image for visual monitoring of the process.

17. A method of monitoring a process in which a seasoning is added to a food product under variable operating conditions, comprising the steps of:
  shining a light onto the food product;
  sequentially capturing multivariate images of the food product in the visible spectrum, each image consisting of an image array having a plurality of pixel elements, each pixel element having intensity values of the colours red, green, and blue defining three dimensions for the image array;
  applying a multi-way principal component analysis to the image array to reduce the dimensions of the image array to a $t_1$–$t_2$ score space;
  creating a feature vector from said $t_1$–$t_2$ score space;
  performing a regression method to correlate the feature vector with a coating property on the food product; and,
  creating an output of the coating property for continuous monitoring and feed back control of the operating conditions of the process.

18. A method of monitoring a process in which a seasoning is added to a snack food product under variable operating conditions, the method comprising the steps of:
  shining a light onto a food product;
  sequentially capturing multivariate images of the food product in the visible spectrum, each image consisting of an image array having a plurality of pixel elements, each pixel element having intensity values of the colours red, green, and blue defining three dimensions for the image array;
  applying a multi-way principal component analysis to the image array to reduce the dimensions of the image array to a first $t_1$–$t_2$ score space;
  selecting a mask to inscribe an area A in said first $t_1$–$t_2$ score space which excludes background from the image array;
  projecting the multivariate images to said first $t_1$–$t_2$ score space and removing pixels which lie outside said area A to create pure product images;
  applying a multi-way principal component analysis to the pure product images to reduce the dimensions of the pure product images to a second $t_1$–$t_2$ score space;
  creating a feature vector from said second $t_1$–$t_2$ score space;
  performing a regression method to correlate the feature vector with a coating property of the food product; and,
  creating an output of the coating property for continuous monitoring and feed back control of the operating conditions of the process.

19. A method according to claim 18 in which the regression method is performed on the feature vector and selected process measurements to create the output of the coating property.

20. A method according to claim 18 in which the coating property is selected from the group comprising predicted seasoning concentration, seasoning distribution plot, seasoning distribution variance and color-coded seasoning concentration image.

21. A method of monitoring a process in which a fuel is consumed to produce a flame under changing operating conditions, comprising the following steps of:
  sequentially capturing multivariate images of the flame in the visible spectrum, each image consisting of an image array having a plurality of pixel elements, each pixel element having intensity values of the colours red, green, and blue defining three dimensions for the image array;
  applying a multi-way principal component analysis to the image array to reduce the dimensions of the image array to a $t_1$–$t_2$ score space;
  selecting a mask to inscribe an area A in said $t_1$–$t_2$ space corresponding to a flame luminous region;
  calculating statistical features of said flame luminous region to create a feature vector;
  performing a regression method to correlate the feature vector and at least one selected process measurements with a characterizing feature of the process; and,
  creating an output of said characterizing feature for continuous monitoring of the operating conditions of the process.

22. A method according to claim 21 in which said statistical feature is selected from the group containing flame area, flame brightness, flame luminous uniformity, average brightness of flame region, number of colours appearing in the flame region.

23. A method according to claim 21 in which said regression method is selected from principal component regression (PCR), partial least squares (PLS), multivariate linear regression (MLR) and artificial neural network (ANN).

24. A method according to claim 21 in which the characterizing feature is selected from the group comprising steam flow, concentration of pollutants and reactants in the process.

25. A method for product feature monitoring and quality control in an on-line environment comprising the steps of:
  exposing a food product to an electromagnetic radiation source;
  imaging at least one product feature of the food product;

extracting background features from the product feature image;

creating an image score space summarizing information in the product feature image;

correlating the product feature image score space to a training sample score space by statistical regression; and, predicting the occurrence of the product feature on the food product.

26. The method of claim 25 wherein the predicted food product feature is at least one of the quantity, characteristic, level, or degree of the product feature on the food product.

27. The method of claim 25 wherein the product feature is the coating coverage on the food product.

28. The method of claim 25 wherein the product feature is one of toast points, seasoning concentration, seasoning coverage, ingredient concentration, surface blisters, surface visual defects, or texture of the food product.

29. The method of claim 25 wherein the prediction of the occurrence of the product feature on the product is calculated within subsections of the product feature image.

30. The method of claim 29 wherein a product feature variance is calculated based on at least one of the values generated from the prediction phase within the subsections of the image of the product feature and the product feature variance across the image is reported for monitoring and controlling online product feature variance.

31. The method of claim 25 wherein the occurrence prediction is for the presence or absence of the product feature.

32. The method of claim 25 wherein the product feature is imaged by at least one of visual light spectrum imaging, infrared spectrum imaging, ultraviolet spectrum imaging, audible sound wave detection, inaudible sound wave detection, mass spectroscopy and chromatography.

33. The method of claim 25 wherein the product feature is a food product or an ingredient of a food product.

34. The method of claim 25 wherein an image acquisition apparatus, a computer processor and computer program for image processing are utilized to reduce the methodology to on-line practice for a product manufacturing process.

35. The method of claim 25 further comprising automatically adjusting an on-line manufacturing process with closed loop control.

36. The method of claim 25 further comprising providing quality control images with visualization software to provide process monitoring, control, alarms and defective product aborting for a product manufacturing process.

37. The method of claim 25 wherein the food product is either bedded or not bedded.

38. The method of claim 25 further comprising the step of:

developing feature correlation models through statistical regression between a predicted value for a product coating coverage, the amount of coating, the product density, surface area, and product depth or distance from the imaging system.

39. The method of claim 38 wherein at least one of the correlation models are used to predict or augment a measurement value of at least one product feature variable using measurements of at least one other feature variable.

40. The method of claim 25 wherein the predicted occurrence of a product feature is the product bulk density and specific bulk density.

41. The method of claim 25 wherein the correlation of the product features includes at least one of product appearance, seasoning concentration, seasoning coverage, product density, bedded product depth and product distance from the imaging apparatus.

42. The method of claim 41 wherein a specific bed depth model is used to predict the bed depth of the product.

43. The method of claim 42 wherein the predicted specific bed depth is used to augment the measurement of other product features which are affected by variable bed depth and distance from the imaging device.

* * * * *